United States Patent
Petrossian et al.

(10) Patent No.: US 11,884,749 B2
(45) Date of Patent: Jan. 30, 2024

(54) COMPOSITIONS AND METHODS FOR TREATING ENDOMETRIOSIS

(71) Applicant: EndoMet Biosciences, Inc., Irvine, CA (US)

(72) Inventors: Tanya Petrossian, Laguna Niguel, CA (US); Stephen Fiacco, Laguna Niguel, CA (US); Tristin Rose, Laguna Niguel, CA (US); Amanda Hardy, Laguna Niguel, CA (US); Keerthi Boddupally, Laguna Niguel, CA (US); Matthew Willmore, Laguna Niguel, CA (US)

(73) Assignee: EndoMet Biosciences, Inc., Irvine, CA (US)

( * ) Notice: Subject to any disclaimer, the term of this patent is extended or adjusted under 35 U.S.C. 154(b) by 387 days.

(21) Appl. No.: 17/295,377

(22) PCT Filed: Nov. 21, 2019

(86) PCT No.: PCT/US2019/062679
§ 371 (c)(1),
(2) Date: May 19, 2021

(87) PCT Pub. No.: WO2020/106995
PCT Pub. Date: May 28, 2020

(65) Prior Publication Data
US 2023/0121738 A1    Apr. 20, 2023

Related U.S. Application Data

(60) Provisional application No. 62/770,601, filed on Nov. 21, 2018.

(51) Int. Cl.
*C07K 7/08* (2006.01)
*A61P 15/02* (2006.01)
*A61K 38/00* (2006.01)

(52) U.S. Cl.
CPC .............. *C07K 7/08* (2013.01); *A61P 15/02* (2018.01); *A61K 38/00* (2013.01)

(58) Field of Classification Search
CPC ............ C07K 7/08; A61P 15/02; A61K 38/00
See application file for complete search history.

(56) References Cited

U.S. PATENT DOCUMENTS

| | | |
|---|---|---|
| 11,198,713 B2 | 12/2021 | Hilinski et al. |
| 2007/0026454 A1 | 2/2007 | Rosen et al. |
| 2009/0311290 A1 | 12/2009 | Hertelendy et al. |
| 2011/0214206 A1 | 9/2011 | La Rosa et al. |
| 2014/0005118 A1 | 1/2014 | Verdine et al. |
| 2015/0284437 A1 | 10/2015 | Verdine et al. |
| 2022/0213154 A1 | 7/2022 | Hilinski et al. |

FOREIGN PATENT DOCUMENTS

| | | |
|---|---|---|
| EP | 1323732 A1 | 7/2003 |
| JP | WO2002024738 A1 | 1/2004 |
| JP | 2013505300 A | 2/2013 |
| JP | 2014515748 A | 7/2014 |
| JP | 2018513187 A | 5/2018 |
| WO | WO-2011038049 A1 | 3/2011 |
| WO | WO-2012142604 A2 | 10/2012 |
| WO | WO-2016172722 A1 | 10/2016 |
| WO | WO-2020106995 A1 | 5/2020 |

OTHER PUBLICATIONS

Aberle et al., beta-catenin is a target for the ubiquitin-proteasome pathway. EMBO J 16(13):3797-3804 (1997).
Amidon et al. Colon-Targeted Oral Drug Delivery Systems: Design Trends and Approaches, AAPS PharmSciTech 16(4):731-741 (2015).
Burns et al., Role of estrogen receptor signaling required for endometriosis-like lesion establishment in a mouse model. Endocrinology 153(8):3960-3971 (2012).
Chourasia et al., Pharmaceutical approaches to colon targeted drug delivery systems. J Pharm Pharm Sci 6(1):33-66 (2003).
Clevers, Wnt/beta-catenin signaling in development and disease. Cell 127(3):469-480 (2006).
Fiacco et al., N-Methyl scanning mutagenesis generates protease-resistant G protein ligands with improved affinity and selectivity. Chembiochem 9(14):2200-2203 (2008).
Giudice et al., Endometriosis. Lancet 364(9447):1789-1799 (2004).
Guan et al., Overexpression of chloride channel-3 is associated with the increased migration and invasion ability of ectopic endometrial cells from patients with endometriosis. Hum Reprod 31(5):986-998 (2016).
Jeong et al., beta-catenin mediates glandular formation and dysregulation of beta-catenin induces hyperplasia formation in the murine uterus. Oncogene 28(1):31-40 (2009).
Jha et al., Profiling of E-cadherin, beta-catenin and Ca(2+) in embryo-uterine interactions at implantation. FEBS Lett 580(24):5653-5660 (2006).
Kouzmenko et al., Wnt/beta-catenin and estrogen signaling converge in vivo. J Biol Chem 279(39):40255-40258 (2004).
Kumar et al. Colon targeted drug delivery systems—an overview. Curr Drug Deliv 5(3):186-198 (2008).
Lee et al., Mouse models of implantation. Trends Endocrinol Metab 18(6):234-239 (2007).
Matsuzaki et al., In vitro effects of a small-molecule antagonist of the Tcf/ß-catenin complex on endometrial and endometriotic cells of patients with endometriosis. PLOS One 8(4):e61690 (2013).
Matsuzaki et al., Targeting the Wnt/β-catenin pathway in endometriosis: a potentially effective approach for treatment and prevention. Mol Cell Ther 2:36 (2014).

(Continued)

*Primary Examiner* — Amber D Steele
(74) *Attorney, Agent, or Firm* — Wilson Sonsini Goodrich & Rosati

(57) ABSTRACT

Provided herein are peptides that bind β-catenin, and compositions comprising said peptides. Peptides binding β-catenin prevent translocation to the nucleus and modulate the canonical Wnt pathway. Also provided herein are methods of using said peptides and compositions in the treatment of tissue-infiltrating conditions including endometriosis.

18 Claims, 12 Drawing Sheets

Specification includes a Sequence Listing.

(56) References Cited

OTHER PUBLICATIONS

Morrow et al., Sustained release of proteins from a modified vaginal ring device. Eur J Pharm Biopharm 77(1):3-10 (2011).

Onder et al., Loss of E-cadherin promotes metastasis via multiple downstream transcriptional pathways. Cancer Res 68(10):3645-3654 (2008).

Patel et al., Therapeutic opportunities in colon-specific drug-delivery systems. Crit Rev Ther Drug Carrier Syst 24(2):147-202 (2007).

Pazhohan et al., The Wnt/β-catenin signaling in endometriosis, the expression of total and active forms of β-catenin, total and inactive forms of glycogen synthase kinase-3β, WNT7a and DICKKOPF-1. Eur J Obstet Gynecol Reprod Biol 220:1-5 (2018).

PCT/US2019/062679 International Search Report and Written Opinion dated Apr. 28, 2020.

Sampson, Metastatic or Embolic Endometriosis, due to the Menstrual Dissemination of Endometrial Tissue into the Venous Circulation. Am J Pathol 3(2):93-110 (1927).

Selcuk et al., Recurrence of endometriosis; risk factors, mechanisms and biomarkers; review of the literature. J Turk Ger Gynecol Assoc 14(2):98-103 (2013).

Valentijn et al., SSEA-1 isolates human endometrial basal glandular epithelial cells: phenotypic and functional characterization and implications in the pathogenesis of endometriosis. Hum Reprod 28(10):2695-2708 (2013).

Van Den Mooter. Colon drug delivery. Expert Opin Drug Deliv. 3(1):111-125 (2006).

Xiong et al., Estradiol promotes cells invasion by activating β-catenin signaling pathway in endometriosis. Reproduction 150(6):507-516 (2015).

Zhang et al., 17 β-Estradiol promotes vascular endothelial growth factor expression via the Wnt/β-catenin pathway during the pathogenesis of endometriosis. Mol Hum Reprod 22(7):526-535 (2016).

Matsuzaki, S. et al., Involvement of the Wnt/beta-Cantenin Signaling Pathway in the Cellular and Molecular Mechanisms of Fibrosis in Endometriosis, PLOS One, 2013, vol. 8, No. 10, article No. e76808, pp. 1-12.

PCT/US2019/062679 International Preliminary Report on Patentability dated May 25, 2021.

Extended European Search Report dated Sep. 20, 2022 for European Application No. 19887008.1.

Huttenrauch, F et al., "β-Arrestin Binding to CC Chemokine Receptor 5 Requires Multiple C-terminal Receptor Phosphorylation Sites and Involves a Conserved Asp-Arg-Tyr Sequence Motif", The Journal of Biological Chemistry, 2002, vol. 277, No. 34, p. 30769-30777.

Luciferase Reporter

Cell Proliferation

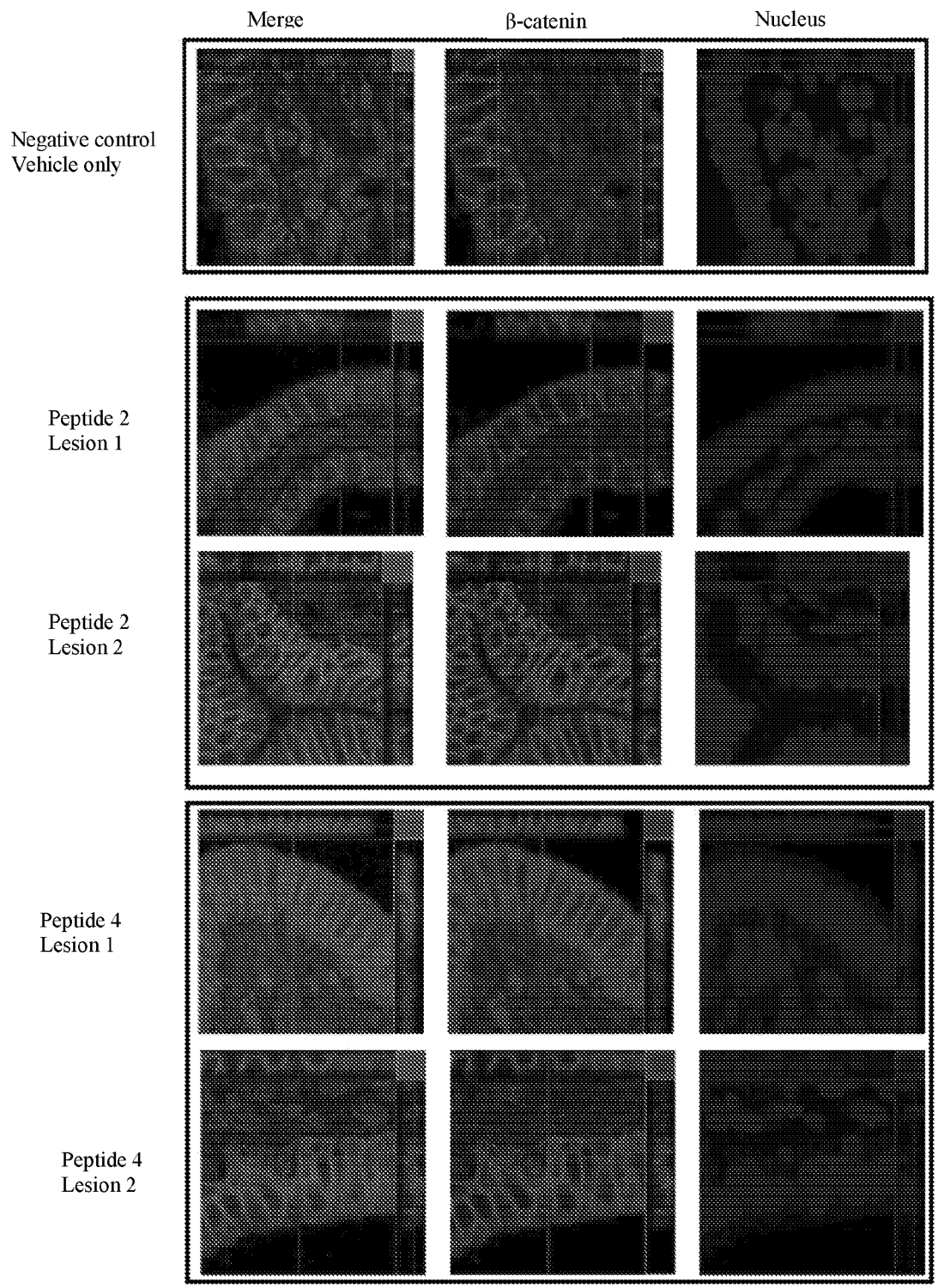

SEQUENCE LISTING

<160> NUMBER OF SEQ ID NOS: 504

<210> SEQ ID NO 1
<211> LENGTH: 16
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: NMe-Trp

<400> SEQUENCE: 1

Gly Trp Trp Glu Ser Ile Leu Asp Glu His Val Gln Arg Val Trp Gly
1               5                   10                  15

<210> SEQ ID NO 2
<211> LENGTH: 16
<212> TYPE: PRT

```
<213> ORGANISM: Homo sapiens
<220> FEATURE:
<221> NAME/KEY: MOD_RES
<222> LOCATION: (3)..(3)
<223> OTHER INFORMATION: NMe-Trp

<400> SEQUENCE: 2

Gly Trp Trp Glu Ser Ile Leu Asp Glu His Val Gln Arg Val Trp Gly
1               5                   10                  15

<210> SEQ ID NO 3
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: NMeNva
<220> FEATURE:
<221> NAME/KEY: MOD_RES
<222> LOCATION: (8)..(8)
<223> OTHER INFORMATION: NMeNva
<220> FEATURE:
<221> NAME/KEY: MOD_RES
<222> LOCATION: (11)..(11)
<223> OTHER INFORMATION: NMeNva

<400> SEQUENCE: 3

Met Met Val Gln Ser Leu Phe Val Pro Pro Val Lys
1               5                   10

<210> SEQ ID NO 4
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: NMeNva
<220> FEATURE:
<221> NAME/KEY: MOD_RES
<222> LOCATION: (8)..(8)
<223> OTHER INFORMATION: NMeNva
<220> FEATURE:
<221> NAME/KEY: MOD_RES
<222> LOCATION: (11)..(11)
<223> OTHER INFORMATION: NMeNva

<400> SEQUENCE: 4

Met Met Val Gln Ser Leu Phe Val Pro Pro Val Lys
1               5                   10

<210> SEQ ID NO 5
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: NMeNva

<400> SEQUENCE: 5

Met Trp Val Trp Leu Ser Arg Gln Trp Ile Val Lys
1               5                   10

<210> SEQ ID NO 6
<211> LENGTH: 12
<212> TYPE: PRT
<213> ORGANISM: Homo sapiens

<400> SEQUENCE: 6
```

Met Ser Arg Met Trp Phe Leu Ile Ser Phe Trp Lys
1               5                   10

<210> SEQ ID NO 7
<211> LENGTH: 9
<212> TYPE: PRT
<213> ORGANISM: Homo sapiens

<400> SEQUENCE: 7

Met Trp Phe Leu Ile Ser Phe Trp Ala
1               5

<210> SEQ ID NO 8
<211> LENGTH: 9
<212> TYPE: PRT
<213> ORGANISM: Homo sapiens

<400> SEQUENCE: 8

Met Trp Phe Leu Ile Ser Phe Ala Gly
1               5

<210> SEQ ID NO 9
<211> LENGTH: 9
<212> TYPE: PRT
<213> ORGANISM: Homo sapiens

<400> SEQUENCE: 9

Met Trp Phe Leu Ile Ser Ala Trp Gly
1               5

<210> SEQ ID NO 10
<211> LENGTH: 9
<212> TYPE: PRT
<213> ORGANISM: Homo sapiens

<400> SEQUENCE: 10

Met Trp Phe Leu Ile Ala Phe Trp Gly
1               5

<210> SEQ ID NO 11
<211> LENGTH: 9
<212> TYPE: PRT
<213> ORGANISM: Homo sapiens

<400> SEQUENCE: 11

Met Trp Phe Leu Ala Ser Phe Trp Gly
1               5

<210> SEQ ID NO 12
<211> LENGTH: 9
<212> TYPE: PRT
<213> ORGANISM: Homo sapiens

<400> SEQUENCE: 12

Met Trp Phe Ala Ile Ser Phe Trp Gly
1               5

<210> SEQ ID NO 13
<211> LENGTH: 9
<212> TYPE: PRT
<213> ORGANISM: Homo sapiens

<400> SEQUENCE: 13

Met Trp Ala Leu Ile Ser Phe Trp Gly

```
1               5

<210> SEQ ID NO 14
<211> LENGTH: 13
<212> TYPE: PRT
<213> ORGANISM: Homo sapiens

<400> SEQUENCE: 14

Met Ser Arg Met Trp Phe Leu Ile Ser Phe Trp Met Gly
1               5                   10

<210> SEQ ID NO 15
<211> LENGTH: 12
<212> TYPE: PRT
<213> ORGANISM: Homo sapiens

<400> SEQUENCE: 15

Met Ile Arg Met Trp Phe Leu Ile Ser Phe Trp Gly
1               5                   10

<210> SEQ ID NO 16
<211> LENGTH: 13
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Nme-Ala

<400> SEQUENCE: 16

Met Ser Arg Met Trp Phe Leu Ile Ser Phe Trp Ala Gly
1               5                   10

<210> SEQ ID NO 17
<211> LENGTH: 9
<212> TYPE: PRT
<213> ORGANISM: Homo sapiens

<400> SEQUENCE: 17

Met Trp Phe Leu Ile Ser Phe Trp Gly
1               5

<210> SEQ ID NO 18
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala

<400> SEQUENCE: 18

Lys Ala Glu Ser Ile Leu Asp Glu His Val Gln Arg Val Trp Gly
1               5                   10                  15

<210> SEQ ID NO 19
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala

<400> SEQUENCE: 19

Lys Ala Gln Ser Ile Leu Asp Glu His Val Gln Arg Val Trp Gly
1               5                   10                  15
```

<210> SEQ ID NO 20
<211> LENGTH: 16
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Nme-Ala

<400> SEQUENCE: 20

Lys Trp Ala Gln Ser Ile Leu Asn Gln His Val Gln Arg Val Trp Gly
1               5                   10                  15

<210> SEQ ID NO 21
<211> LENGTH: 13
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Lys(Aoc)
<220> FEATURE:
<221> NAME/KEY: MOD_RES
<222> LOCATION: (7)..(7)
<223> OTHER INFORMATION: NMe-Trp

<400> SEQUENCE: 21

Lys Met Ile Arg Met Trp Phe Leu Ile Ser Phe Trp Gly
1               5                   10

<210> SEQ ID NO 22
<211> LENGTH: 15
<212> TYPE: PRT
<213> ORGANISM: Homo sapiens

<400> SEQUENCE: 22

Met Trp Glu Ser Ile Leu Asp Glu His Val Gln Arg Val Trp Gly
1               5                   10                  15

<210> SEQ ID NO 23
<211> LENGTH: 16
<212> TYPE: PRT
<213> ORGANISM: Homo sapiens

<400> SEQUENCE: 23

Met Trp Glu Ser Ile Leu Asp Glu His Met Gln Arg Val Trp Arg Gly
1               5                   10                  15

<210> SEQ ID NO 24
<211> LENGTH: 14
<212> TYPE: PRT
<213> ORGANISM: Homo sapiens

<400> SEQUENCE: 24

Lys Met Ser Arg Met Trp Phe Leu Ile Ser Phe Trp Arg Gly
1               5                   10

<210> SEQ ID NO 25
<211> LENGTH: 13
<212> TYPE: PRT
<213> ORGANISM: Homo sapiens

<400> SEQUENCE: 25

Lys Met Ser Arg Met Trp Leu Leu Ile Ser Phe Trp Gly
1               5                   10

```
<210> SEQ ID NO 26
<211> LENGTH: 10
<212> TYPE: PRT
<213> ORGANISM: Homo sapiens

<400> SEQUENCE: 26

Lys Met Trp Phe Leu Ile Ser Phe Trp Gly
1               5                   10

<210> SEQ ID NO 27
<211> LENGTH: 13
<212> TYPE: PRT
<213> ORGANISM: Homo sapiens

<400> SEQUENCE: 27

Lys Met Ser Arg Met Trp Tyr Leu Ile Ser Phe Trp Gly
1               5                   10

<210> SEQ ID NO 28
<211> LENGTH: 13
<212> TYPE: PRT
<213> ORGANISM: Homo sapiens

<400> SEQUENCE: 28

Lys Met Ser Arg Met Trp Phe Leu Ile Ser Leu Trp Gly
1               5                   10

<210> SEQ ID NO 29
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 29

Lys Met Pro Leu Ala Ile Ser Trp Phe Glu His Ile Gly
1               5                   10

<210> SEQ ID NO 30
<211> LENGTH: 16
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Nme-Ala

<400> SEQUENCE: 30

Lys Met Ala Glu Ser Ile Leu Asp Glu His Val Gln Arg Val Trp Gly
1               5                   10                  15

<210> SEQ ID NO 31
<211> LENGTH: 12
<212> TYPE: PRT
<213> ORGANISM: Homo sapiens

<400> SEQUENCE: 31

Lys Met Ser Arg Met Trp Tyr Leu Ile Ser Phe Trp
1               5                   10

<210> SEQ ID NO 32
<211> LENGTH: 11
<212> TYPE: PRT
<213> ORGANISM: Homo sapiens
```

```
<400> SEQUENCE: 32

Lys Ser Arg Met Trp Tyr Leu Ile Ser Phe Trp
1               5                   10

<210> SEQ ID NO 33
<211> LENGTH: 14
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Pra

<400> SEQUENCE: 33

Trp Glu Ser Ile Leu Asp Glu His Val Gln Arg Val Trp Xaa
1               5                   10

<210> SEQ ID NO 34
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: aMe-Val

<400> SEQUENCE: 34

Met Trp Glu Ser Ile Leu Asp Glu His Val Gln Arg Val Trp Gly
1               5                   10                  15

<210> SEQ ID NO 35
<211> LENGTH: 15
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: aMe-Ser

<400> SEQUENCE: 35

Met Trp Glu Ser Ile Leu Asp Glu His Val Gln Arg Val Trp Gly
1               5                   10                  15

<210> SEQ ID NO 36
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Trp

<400> SEQUENCE: 36

Trp Trp Glu Ser Ile Leu Asp Glu His Val Gln Arg Val Trp Gly
1               5                   10                  15

<210> SEQ ID NO 37
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: NMe-Trp
<220> FEATURE:
<221> NAME/KEY: MOD_RES
<222> LOCATION: (2)..(2)
<223> OTHER INFORMATION: NMe-Trp
```

```
<400> SEQUENCE: 37

Trp Trp Glu Ser Ile Leu Asp Glu His Val Gln Arg Val Trp Gly
1               5                   10                  15

<210> SEQ ID NO 38
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Trp
<220> FEATURE:
<221> NAME/KEY: MOD_RES
<222> LOCATION: (4)..(4)
<223> OTHER INFORMATION: aMe-Ser
<220> FEATURE:
<221> NAME/KEY: MOD_RES
<222> LOCATION: (10)..(10)
<223> OTHER INFORMATION: aMe-Val

<400> SEQUENCE: 38

Trp Trp Glu Ser Ile Leu Asp Glu His Val Gln Arg Val Trp Gly
1               5                   10                  15

<210> SEQ ID NO 39
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Trp
<220> FEATURE:
<221> NAME/KEY: MOD_RES
<222> LOCATION: (10)..(10)
<223> OTHER INFORMATION: aMe-Val

<400> SEQUENCE: 39

Trp Trp Glu Ser Ile Leu Asp Glu His Val Gln Arg Val Trp Gly
1               5                   10                  15

<210> SEQ ID NO 40
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Trp
<220> FEATURE:
<221> NAME/KEY: MOD_RES
<222> LOCATION: (4)..(4)
<223> OTHER INFORMATION: aMe-Ser

<400> SEQUENCE: 40

Trp Trp Glu Ser Ile Leu Asp Glu His Val Gln Arg Val Trp Gly
1               5                   10                  15

<210> SEQ ID NO 41
<211> LENGTH: 12
<212> TYPE: PRT
<213> ORGANISM: Homo sapiens

<400> SEQUENCE: 41

Met Ser Arg Met Trp Phe Leu Ile Ser Phe Trp Gly
1               5                   10
```

```
<210> SEQ ID NO 42
<211> LENGTH: 9
<212> TYPE: PRT
<213> ORGANISM: Homo sapiens

<400> SEQUENCE: 42

Met Trp Phe Leu Ile Cys Phe Trp Gly
1               5

<210> SEQ ID NO 43
<211> LENGTH: 9
<212> TYPE: PRT
<213> ORGANISM: Homo sapiens

<400> SEQUENCE: 43

Met Trp Ile Leu Ile Ser Phe Trp Gly
1               5

<210> SEQ ID NO 44
<211> LENGTH: 13
<212> TYPE: PRT
<213> ORGANISM: Homo sapiens

<400> SEQUENCE: 44

Met Ser Arg Met Trp Phe Leu Ile Ser Phe Trp Thr Gly
1               5                   10

<210> SEQ ID NO 45
<211> LENGTH: 10
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Nme-Ala

<400> SEQUENCE: 45

Met Trp Phe Leu Ile Ser Phe Trp Ala Gly
1               5                   10

<210> SEQ ID NO 46
<211> LENGTH: 12
<212> TYPE: PRT
<213> ORGANISM: Homo sapiens

<400> SEQUENCE: 46

Met Ser Arg Met Trp Phe Leu Ile Cys Phe Trp Gly
1               5                   10

<210> SEQ ID NO 47
<211> LENGTH: 10
<212> TYPE: PRT
<213> ORGANISM: Homo sapiens

<400> SEQUENCE: 47

Met Trp Phe Leu Ile Ser Phe Trp Glu Gly
1               5                   10

<210> SEQ ID NO 48
<211> LENGTH: 12
<212> TYPE: PRT
<213> ORGANISM: Homo sapiens

<400> SEQUENCE: 48

Met Ser Arg Thr Trp Phe Leu Ile Ser Phe Trp Gly
1               5                   10
```

<210> SEQ ID NO 49
<211> LENGTH: 10
<212> TYPE: PRT
<213> ORGANISM: Homo sapiens

<400> SEQUENCE: 49

Met Trp Phe Leu Ile Ser Phe Trp Arg Gly
1               5                   10

<210> SEQ ID NO 50
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 50

Met Ser Arg Met Ala Phe Leu Ile Ser Phe Trp Gly
1               5                   10

<210> SEQ ID NO 51
<211> LENGTH: 12
<212> TYPE: PRT
<213> ORGANISM: Homo sapiens

<400> SEQUENCE: 51

Met Ser Arg Met Trp Ile Leu Ile Ser Phe Trp Gly
1               5                   10

<210> SEQ ID NO 52
<211> LENGTH: 12
<212> TYPE: PRT
<213> ORGANISM: Homo sapiens

<400> SEQUENCE: 52

Met Ser Arg Met Leu Phe Leu Ile Ser Phe Trp Gly
1               5                   10

<210> SEQ ID NO 53
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: NMe-Trp

<400> SEQUENCE: 53

Met Ile Arg Met Trp Phe Leu Ile Ser Phe Trp Gly
1               5                   10

<210> SEQ ID NO 54
<211> LENGTH: 12
<212> TYPE: PRT
<213> ORGANISM: Homo sapiens

<400> SEQUENCE: 54

Met Ser Arg Met Trp Phe Leu Ile Ser Ser Trp Gly
1               5                   10

<210> SEQ ID NO 55
<211> LENGTH: 12
<212> TYPE: PRT

<213> ORGANISM: Homo sapiens

<400> SEQUENCE: 55

Met Ser Arg Ile Trp Phe Leu Ile Ser Phe Trp Gly
1               5                   10

<210> SEQ ID NO 56
<211> LENGTH: 12
<212> TYPE: PRT
<213> ORGANISM: Homo sapiens

<400> SEQUENCE: 56

Met Ser Arg Met Trp Phe Leu Val Ser Phe Trp Gly
1               5                   10

<210> SEQ ID NO 57
<211> LENGTH: 13
<212> TYPE: PRT
<213> ORGANISM: Homo sapiens

<400> SEQUENCE: 57

Met Ser Arg Met Trp Phe Leu Ile Ser Phe Trp Glu Gly
1               5                   10

<210> SEQ ID NO 58
<211> LENGTH: 13
<212> TYPE: PRT
<213> ORGANISM: Homo sapiens

<400> SEQUENCE: 58

Met Ser Arg Met Trp Phe Leu Ile Ser Phe Trp Arg Gly
1               5                   10

<210> SEQ ID NO 59
<211> LENGTH: 12
<212> TYPE: PRT
<213> ORGANISM: Homo sapiens

<400> SEQUENCE: 59

Met Ser Arg Lys Trp Phe Leu Ile Ser Phe Trp Gly
1               5                   10

<210> SEQ ID NO 60
<211> LENGTH: 12
<212> TYPE: PRT
<213> ORGANISM: Homo sapiens

<400> SEQUENCE: 60

Met Ser Arg Met Trp Leu Leu Ile Ser Phe Trp Gly
1               5                   10

<210> SEQ ID NO 61
<211> LENGTH: 12
<212> TYPE: PRT
<213> ORGANISM: Homo sapiens

<400> SEQUENCE: 61

Met Asn Arg Met Trp Phe Leu Ile Ser Phe Trp Gly
1               5                   10

<210> SEQ ID NO 62
<211> LENGTH: 12
<212> TYPE: PRT
<213> ORGANISM: Homo sapiens

<400> SEQUENCE: 62

Met Ser Arg Met Trp Phe Leu Thr Ser Phe Trp Gly
1               5                   10

<210> SEQ ID NO 63
<211> LENGTH: 12
<212> TYPE: PRT
<213> ORGANISM: Homo sapiens

<400> SEQUENCE: 63

Met Ser Arg Met Trp Phe Leu Phe Ser Phe Trp Gly
1               5                   10

<210> SEQ ID NO 64
<211> LENGTH: 12
<212> TYPE: PRT
<213> ORGANISM: Homo sapiens

<400> SEQUENCE: 64

Met Ser Arg Val Trp Phe Leu Ile Ser Phe Trp Gly
1               5                   10

<210> SEQ ID NO 65
<211> LENGTH: 12
<212> TYPE: PRT
<213> ORGANISM: Homo sapiens

<400> SEQUENCE: 65

Met Ser Arg Met Trp Phe Pro Ile Ser Phe Trp Gly
1               5                   10

<210> SEQ ID NO 66
<211> LENGTH: 12
<212> TYPE: PRT
<213> ORGANISM: Homo sapiens

<400> SEQUENCE: 66

Met Ser Arg Met Trp Tyr Leu Ile Ser Phe Trp Gly
1               5                   10

<210> SEQ ID NO 67
<211> LENGTH: 12
<212> TYPE: PRT
<213> ORGANISM: Homo sapiens

<400> SEQUENCE: 67

Met Gly Arg Met Trp Phe Leu Ile Ser Phe Trp Gly
1               5                   10

<210> SEQ ID NO 68
<211> LENGTH: 12
<212> TYPE: PRT
<213> ORGANISM: Homo sapiens

<400> SEQUENCE: 68

Met Ser Arg Met Trp Phe Leu Ile Ser Leu Trp Gly
1               5                   10

<210> SEQ ID NO 69
<211> LENGTH: 12
<212> TYPE: PRT
<213> ORGANISM: Homo sapiens

<400> SEQUENCE: 69

```
Met Ser Arg Met Trp Phe Leu Ile Ser Phe Arg Gly
1               5                   10
```

<210> SEQ ID NO 70
<211> LENGTH: 12
<212> TYPE: PRT
<213> ORGANISM: Homo sapiens

<400> SEQUENCE: 70

```
Met Ser Arg Met Trp Phe Leu Asn Ser Phe Trp Gly
1               5                   10
```

<210> SEQ ID NO 71
<211> LENGTH: 10
<212> TYPE: PRT
<213> ORGANISM: Homo sapiens

<400> SEQUENCE: 71

```
Lys Met Trp Ile Leu Ile Ser Phe Trp Gly
1               5                   10
```

<210> SEQ ID NO 72
<211> LENGTH: 11
<212> TYPE: PRT
<213> ORGANISM: Homo sapiens

<400> SEQUENCE: 72

```
Met Ser Arg Met Trp Phe Leu Ile Ser Phe Trp
1               5                   10
```

<210> SEQ ID NO 73
<211> LENGTH: 11
<212> TYPE: PRT
<213> ORGANISM: Homo sapiens

<400> SEQUENCE: 73

```
Met Thr Arg Met Trp Phe Leu Ile Ser Phe Trp
1               5                   10
```

<210> SEQ ID NO 74
<211> LENGTH: 11
<212> TYPE: PRT
<213> ORGANISM: Homo sapiens

<400> SEQUENCE: 74

```
Met Gln Arg Met Trp Phe Leu Ile Ser Phe Trp
1               5                   10
```

<210> SEQ ID NO 75
<211> LENGTH: 11
<212> TYPE: PRT
<213> ORGANISM: Homo sapiens

<400> SEQUENCE: 75

```
Met Ser Arg Arg Trp Phe Leu Ile Ser Phe Trp
1               5                   10
```

<210> SEQ ID NO 76
<211> LENGTH: 11
<212> TYPE: PRT
<213> ORGANISM: Homo sapiens

<400> SEQUENCE: 76

```
Met Ser Arg Thr Trp Phe Leu Ile Ser Phe Trp
1               5                   10
```

<210> SEQ ID NO 77
<211> LENGTH: 11
<212> TYPE: PRT
<213> ORGANISM: Homo sapiens

<400> SEQUENCE: 77

Met Ser Arg Phe Trp Phe Leu Ile Ser Phe Trp
1               5                   10

<210> SEQ ID NO 78
<211> LENGTH: 11
<212> TYPE: PRT
<213> ORGANISM: Homo sapiens

<400> SEQUENCE: 78

Met Ser Arg Trp Trp Phe Leu Ile Ser Phe Trp
1               5                   10

<210> SEQ ID NO 79
<211> LENGTH: 11
<212> TYPE: PRT
<213> ORGANISM: Homo sapiens

<400> SEQUENCE: 79

Trp Ser Arg Met Trp Phe Leu Ile Ser Phe Trp
1               5                   10

<210> SEQ ID NO 80
<211> LENGTH: 11
<212> TYPE: PRT
<213> ORGANISM: Homo sapiens

<400> SEQUENCE: 80

Met Ser Arg Met Trp Trp Leu Ile Ser Phe Trp
1               5                   10

<210> SEQ ID NO 81
<211> LENGTH: 11
<212> TYPE: PRT
<213> ORGANISM: Homo sapiens

<400> SEQUENCE: 81

Phe Ser Arg Met Trp Phe Leu Ile Ser Phe Trp
1               5                   10

<210> SEQ ID NO 82
<211> LENGTH: 11
<212> TYPE: PRT
<213> ORGANISM: Homo sapiens

<400> SEQUENCE: 82

Tyr Ser Arg Met Trp Phe Leu Ile Ser Phe Trp
1               5                   10

<210> SEQ ID NO 83
<211> LENGTH: 11
<212> TYPE: PRT
<213> ORGANISM: Homo sapiens

<400> SEQUENCE: 83

Lys Ser Arg Met Trp Phe Leu Ile Ser Phe Trp
1               5                   10

-continued

```
<210> SEQ ID NO 84
<211> LENGTH: 11
<212> TYPE: PRT
<213> ORGANISM: Homo sapiens

<400> SEQUENCE: 84

Arg Ser Arg Met Trp Phe Leu Ile Ser Phe Trp
1               5                   10

<210> SEQ ID NO 85
<211> LENGTH: 11
<212> TYPE: PRT
<213> ORGANISM: Homo sapiens

<400> SEQUENCE: 85

Asp Ser Arg Met Trp Phe Leu Ile Ser Phe Trp
1               5                   10

<210> SEQ ID NO 86
<211> LENGTH: 11
<212> TYPE: PRT
<213> ORGANISM: Homo sapiens

<400> SEQUENCE: 86

Glu Ser Arg Met Trp Phe Leu Ile Ser Phe Trp
1               5                   10

<210> SEQ ID NO 87
<211> LENGTH: 11
<212> TYPE: PRT
<213> ORGANISM: Homo sapiens

<400> SEQUENCE: 87

Met Ser Arg Lys Trp Phe Leu Ile Ser Phe Trp
1               5                   10

<210> SEQ ID NO 88
<211> LENGTH: 11
<212> TYPE: PRT
<213> ORGANISM: Homo sapiens

<400> SEQUENCE: 88

Met Ser Arg His Trp Phe Leu Ile Ser Phe Trp
1               5                   10

<210> SEQ ID NO 89
<211> LENGTH: 11
<212> TYPE: PRT
<213> ORGANISM: Homo sapiens

<400> SEQUENCE: 89

His Ser Arg Met Trp Phe Leu Ile Ser Phe Trp
1               5                   10

<210> SEQ ID NO 90
<211> LENGTH: 11
<212> TYPE: PRT
<213> ORGANISM: Homo sapiens

<400> SEQUENCE: 90

Trp Ser Arg Lys Trp Phe Leu Ile Ser Phe Trp
1               5                   10

<210> SEQ ID NO 91
<211> LENGTH: 11
```

```
<212> TYPE: PRT
<213> ORGANISM: Homo sapiens

<400> SEQUENCE: 91

Trp Ser Arg His Trp Phe Leu Ile Ser Phe Trp
1               5                   10

<210> SEQ ID NO 92
<211> LENGTH: 11
<212> TYPE: PRT
<213> ORGANISM: Homo sapiens

<400> SEQUENCE: 92

Trp Ser Arg Trp Trp Phe Leu Ile Ser Phe Trp
1               5                   10

<210> SEQ ID NO 93
<211> LENGTH: 11
<212> TYPE: PRT
<213> ORGANISM: Homo sapiens

<400> SEQUENCE: 93

Lys Ser Arg Lys Trp Phe Leu Ile Ser Phe Trp
1               5                   10

<210> SEQ ID NO 94
<211> LENGTH: 11
<212> TYPE: PRT
<213> ORGANISM: Homo sapiens

<400> SEQUENCE: 94

Lys Ser Arg His Trp Phe Leu Ile Ser Phe Trp
1               5                   10

<210> SEQ ID NO 95
<211> LENGTH: 11
<212> TYPE: PRT
<213> ORGANISM: Homo sapiens

<400> SEQUENCE: 95

Lys Ser Arg Trp Trp Phe Leu Ile Ser Phe Trp
1               5                   10

<210> SEQ ID NO 96
<211> LENGTH: 8
<212> TYPE: PRT
<213> ORGANISM: Homo sapiens

<400> SEQUENCE: 96

Met Trp Phe Leu Ile Ser Ser Trp
1               5

<210> SEQ ID NO 97
<211> LENGTH: 7
<212> TYPE: PRT
<213> ORGANISM: Homo sapiens

<400> SEQUENCE: 97

Trp Phe Leu Ile Ser Ser Trp
1               5

<210> SEQ ID NO 98
<211> LENGTH: 7
<212> TYPE: PRT
<213> ORGANISM: Homo sapiens
```

```
<400> SEQUENCE: 98

Trp Phe Leu Ile Ser Phe Trp
1               5

<210> SEQ ID NO 99
<211> LENGTH: 11
<212> TYPE: PRT
<213> ORGANISM: Homo sapiens

<400> SEQUENCE: 99

Met Ser Arg Met Trp Phe Leu Ile Ser Ser Trp
1               5                   10

<210> SEQ ID NO 100
<211> LENGTH: 7
<212> TYPE: PRT
<213> ORGANISM: Homo sapiens

<400> SEQUENCE: 100

Trp Phe Leu Ile Thr Thr Trp
1               5

<210> SEQ ID NO 101
<211> LENGTH: 7
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Ser(Bzl)

<400> SEQUENCE: 101

Trp Phe Leu Ile Ser Ser Trp
1               5

<210> SEQ ID NO 102
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: NMe-Trp

<400> SEQUENCE: 102

Trp Phe Leu Ile Ser Phe Trp
1               5

<210> SEQ ID NO 103
<211> LENGTH: 7
<212> TYPE: PRT
<213> ORGANISM: Homo sapiens

<400> SEQUENCE: 103

Trp Phe Leu Ile Ser Thr Trp
1               5

<210> SEQ ID NO 104
<211> LENGTH: 7
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Ser(Et)
```

```
<400> SEQUENCE: 104

Trp Phe Leu Ile Ser Ser Trp
1               5

<210> SEQ ID NO 105
<211> LENGTH: 11
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Ser(Et)

<400> SEQUENCE: 105

Met Ser Arg Met Trp Phe Leu Ile Ser Ser Trp
1               5                   10

<210> SEQ ID NO 106
<211> LENGTH: 11
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Ser(Bzl)

<400> SEQUENCE: 106

Met Ser Arg Met Trp Phe Leu Ile Ser Ser Trp
1               5                   10

<210> SEQ ID NO 107
<211> LENGTH: 8
<212> TYPE: PRT
<213> ORGANISM: Homo sapiens

<400> SEQUENCE: 107

Met Trp Phe Leu Ile Ser Phe Trp
1               5

<210> SEQ ID NO 108
<211> LENGTH: 9
<212> TYPE: PRT
<213> ORGANISM: Homo sapiens

<400> SEQUENCE: 108

Met Trp Phe Leu Ile Ser Phe Trp Gly
1               5

<210> SEQ ID NO 109
<211> LENGTH: 7
<212> TYPE: PRT
<213> ORGANISM: Homo sapiens

<400> SEQUENCE: 109

Trp Phe Leu Ile Ser Tyr Trp
1               5

<210> SEQ ID NO 110
<211> LENGTH: 7
<212> TYPE: PRT
<213> ORGANISM: Homo sapiens

<400> SEQUENCE: 110

Trp Phe Leu Ile Ser Phe Trp
1               5
```

```
<210> SEQ ID NO 111
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: NMe-Trp

<400> SEQUENCE: 111

Trp Phe Leu Ile Ser Phe Trp
1               5

<210> SEQ ID NO 112
<211> LENGTH: 8
<212> TYPE: PRT
<213> ORGANISM: Homo sapiens

<400> SEQUENCE: 112

Met Trp Phe Leu Ile Ser Phe Trp
1               5

<210> SEQ ID NO 113
<211> LENGTH: 10
<212> TYPE: PRT
<213> ORGANISM: Homo sapiens

<400> SEQUENCE: 113

Lys Met Trp Ile Leu Ile Cys Phe Trp Gly
1               5                   10

<210> SEQ ID NO 114
<211> LENGTH: 10
<212> TYPE: PRT
<213> ORGANISM: Homo sapiens

<400> SEQUENCE: 114

His Met Trp Ile Leu Ile Cys Phe Trp Gly
1               5                   10

<210> SEQ ID NO 115
<211> LENGTH: 10
<212> TYPE: PRT
<213> ORGANISM: Homo sapiens

<400> SEQUENCE: 115

Arg Met Trp Ile Leu Ile Cys Phe Trp Gly
1               5                   10

<210> SEQ ID NO 116
<211> LENGTH: 9
<212> TYPE: PRT
<213> ORGANISM: Homo sapiens

<400> SEQUENCE: 116

Met Trp Ile Leu Ile Cys Phe Trp Gly
1               5

<210> SEQ ID NO 117
<211> LENGTH: 9
<212> TYPE: PRT
<213> ORGANISM: Homo sapiens

<400> SEQUENCE: 117

Lys Trp Ile Leu Ile Cys Phe Trp Gly
```

```
1               5
```

<210> SEQ ID NO 118
<211> LENGTH: 9
<212> TYPE: PRT
<213> ORGANISM: Homo sapiens

<400> SEQUENCE: 118

```
His Trp Ile Leu Ile Cys Phe Trp Gly
1               5
```

<210> SEQ ID NO 119
<211> LENGTH: 9
<212> TYPE: PRT
<213> ORGANISM: Homo sapiens

<400> SEQUENCE: 119

```
Arg Trp Ile Leu Ile Cys Phe Trp Gly
1               5
```

<210> SEQ ID NO 120
<211> LENGTH: 9
<212> TYPE: PRT
<213> ORGANISM: Homo sapiens

<400> SEQUENCE: 120

```
Lys Trp Ile Leu Ile Cys Phe Trp Asp
1               5
```

<210> SEQ ID NO 121
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: aMe-Phe

<400> SEQUENCE: 121

```
Met Trp Ile Leu Ile Cys Phe Trp Gly
1               5
```

<210> SEQ ID NO 122
<211> LENGTH: 10
<212> TYPE: PRT
<213> ORGANISM: Homo sapiens

<400> SEQUENCE: 122

```
Lys Met Trp Ile Leu Ile Ser Phe Trp Gly
1               5                   10
```

<210> SEQ ID NO 123
<211> LENGTH: 10
<212> TYPE: PRT
<213> ORGANISM: Homo sapiens

<400> SEQUENCE: 123

```
His Met Trp Ile Leu Ile Ser Phe Trp Gly
1               5                   10
```

<210> SEQ ID NO 124
<211> LENGTH: 10
<212> TYPE: PRT
<213> ORGANISM: Homo sapiens

<400> SEQUENCE: 124

Arg Met Trp Ile Leu Ile Ser Phe Trp Gly
1               5                   10

<210> SEQ ID NO 125
<211> LENGTH: 9
<212> TYPE: PRT
<213> ORGANISM: Homo sapiens

<400> SEQUENCE: 125

Lys Trp Ile Leu Ile Ser Phe Trp Gly
1               5

<210> SEQ ID NO 126
<211> LENGTH: 9
<212> TYPE: PRT
<213> ORGANISM: Homo sapiens

<400> SEQUENCE: 126

His Trp Ile Leu Ile Ser Phe Trp Gly
1               5

<210> SEQ ID NO 127
<211> LENGTH: 9
<212> TYPE: PRT
<213> ORGANISM: Homo sapiens

<400> SEQUENCE: 127

Trp Trp Ile Leu Ile Ser Phe Trp Gly
1               5

<210> SEQ ID NO 128
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: aMe-Phe

<400> SEQUENCE: 128

Met Trp Ile Leu Ile Ser Phe Trp Gly
1               5

<210> SEQ ID NO 129
<211> LENGTH: 9
<212> TYPE: PRT
<213> ORGANISM: Homo sapiens

<400> SEQUENCE: 129

Met Trp Ile Leu Ile Ser Ser Trp Gly
1               5

<210> SEQ ID NO 130
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: aMe-Leu

<400> SEQUENCE: 130

Met Trp Ile Leu Ile Cys Phe Trp Gly
1               5

```
<210> SEQ ID NO 131
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: aMe-Phe

<400> SEQUENCE: 131

Met Trp Phe Leu Ile Cys Phe Trp Gly
1               5

<210> SEQ ID NO 132
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: aMe-Trp

<400> SEQUENCE: 132

Met Trp Ile Leu Ile Cys Phe Trp Gly
1               5

<210> SEQ ID NO 133
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: aMe-Phe

<400> SEQUENCE: 133

Met Trp Phe Leu Ile Ser Phe Trp Gly
1               5

<210> SEQ ID NO 134
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: aMe-Trp

<400> SEQUENCE: 134

Met Trp Ile Leu Ile Ser Phe Trp Gly
1               5

<210> SEQ ID NO 135
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: (3-Me)Trp

<400> SEQUENCE: 135

Met Trp Phe Leu Ile Cys His Trp Gly
1               5

<210> SEQ ID NO 136
<211> LENGTH: 9
<212> TYPE: PRT
<213> ORGANISM: Homo sapiens
```

```
<220> FEATURE:
<221> NAME/KEY: MOD_RES
<222> LOCATION: (6)..(6)
<223> OTHER INFORMATION: aMe-Ser

<400> SEQUENCE: 136

Met Trp Ile Leu Ile Ser Phe Trp Gly
1               5

<210> SEQ ID NO 137
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: D-Thr

<400> SEQUENCE: 137

Met Trp Ile Leu Ile Thr Phe Trp Gly
1               5

<210> SEQ ID NO 138
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: aMeLeu

<400> SEQUENCE: 138

Met Trp Ile Leu Ile Ser Phe Trp Gly
1               5

<210> SEQ ID NO 139
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: 2Aoc

<400> SEQUENCE: 139

Xaa Trp Phe Leu Ile Cys Phe Trp Gly
1               5

<210> SEQ ID NO 140
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: (1-Me)Trp

<400> SEQUENCE: 140

Met Trp Phe Leu Ile Cys His Trp Gly
1               5

<210> SEQ ID NO 141
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Nva
```

<400> SEQUENCE: 141

Val Trp Phe Leu Ile Cys Phe Trp Gly
1               5

<210> SEQ ID NO 142
<211> LENGTH: 9
<212> TYPE: PRT
<213> ORGANISM: Homo sapiens

<400> SEQUENCE: 142

Asp Trp Phe Leu Ile Cys Phe Trp Gly
1               5

<210> SEQ ID NO 143
<211> LENGTH: 9
<212> TYPE: PRT
<213> ORGANISM: Homo sapiens

<400> SEQUENCE: 143

Met Trp Phe Leu Ile Gln Phe Trp Gly
1               5

<210> SEQ ID NO 144
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: hSer

<400> SEQUENCE: 144

Met Trp Ile Leu Ile Ser Phe Trp Gly
1               5

<210> SEQ ID NO 145
<211> LENGTH: 9
<212> TYPE: PRT
<213> ORGANISM: Homo sapiens

<400> SEQUENCE: 145

Met Trp Phe Leu Ile Cys His Trp Gly
1               5

<210> SEQ ID NO 146
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Ser(Bzl)

<400> SEQUENCE: 146

Met Trp Ile Leu Ile Ser Phe Trp Gly
1               5

<210> SEQ ID NO 147
<211> LENGTH: 9
<212> TYPE: PRT
<213> ORGANISM: Homo sapiens

<400> SEQUENCE: 147

Met Trp Phe Leu Ile Cys Phe Trp Asp
1               5

<210> SEQ ID NO 148
<211> LENGTH: 9
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Ala(2-Pyr)

<400> SEQUENCE: 148

Met Trp Phe Leu Ile Cys Ala Trp Gly
1               5

<210> SEQ ID NO 149
<211> LENGTH: 9
<212> TYPE: PRT
<213> ORGANISM: Homo sapiens

<400> SEQUENCE: 149

Met Trp Phe Leu Ile Gln Phe Tyr Gly
1               5

<210> SEQ ID NO 150
<211> LENGTH: 9
<212> TYPE: PRT
<213> ORGANISM: Homo sapiens

<400> SEQUENCE: 150

Met Trp Ile Leu Ile Thr Phe Trp Gly
1               5

<210> SEQ ID NO 151
<211> LENGTH: 9
<212> TYPE: PRT
<213> ORGANISM: Homo sapiens

<400> SEQUENCE: 151

Met Trp Phe Leu Ile Lys Phe Tyr Gly
1               5

<210> SEQ ID NO 152
<211> LENGTH: 9
<212> TYPE: PRT
<213> ORGANISM: Homo sapiens

<400> SEQUENCE: 152

Met Trp Ile Leu Ile Ser Tyr Trp Gly
1               5

<210> SEQ ID NO 153
<211> LENGTH: 8
<212> TYPE: PRT
<213> ORGANISM: Homo sapiens

<400> SEQUENCE: 153

Met Trp Phe Leu Ile Cys Phe Trp
1               5

<210> SEQ ID NO 154
<211> LENGTH: 9
<212> TYPE: PRT
<213> ORGANISM: Homo sapiens

<400> SEQUENCE: 154

-continued

Met Trp Phe Leu Ile Cys Phe Trp Gly
1               5

<210> SEQ ID NO 155
<211> LENGTH: 9
<212> TYPE: PRT
<213> ORGANISM: Homo sapiens

<400> SEQUENCE: 155

Met Trp Ile Leu Ile Ser Phe Trp Gly
1               5

<210> SEQ ID NO 156
<211> LENGTH: 9
<212> TYPE: PRT
<213> ORGANISM: Homo sapiens

<400> SEQUENCE: 156

Met Trp Ala Leu Ile Ser Phe Trp Gly
1               5

<210> SEQ ID NO 157
<211> LENGTH: 9
<212> TYPE: PRT
<213> ORGANISM: Homo sapiens

<400> SEQUENCE: 157

Met Trp Phe Ala Ile Ser Phe Trp Gly
1               5

<210> SEQ ID NO 158
<211> LENGTH: 9
<212> TYPE: PRT
<213> ORGANISM: Homo sapiens

<400> SEQUENCE: 158

Met Trp Phe Leu Ala Ser Phe Trp Gly
1               5

<210> SEQ ID NO 159
<211> LENGTH: 9
<212> TYPE: PRT
<213> ORGANISM: Homo sapiens

<400> SEQUENCE: 159

Met Trp Phe Leu Ile Ala Phe Trp Gly
1               5

<210> SEQ ID NO 160
<211> LENGTH: 9
<212> TYPE: PRT
<213> ORGANISM: Homo sapiens

<400> SEQUENCE: 160

Met Trp Phe Leu Ile Ser Ala Trp Gly
1               5

<210> SEQ ID NO 161
<211> LENGTH: 9
<212> TYPE: PRT
<213> ORGANISM: Homo sapiens

<400> SEQUENCE: 161

Met Trp Phe Leu Ile Ser Phe Ala Gly
1               5

```
<210> SEQ ID NO 162
<211> LENGTH: 9
<212> TYPE: PRT
<213> ORGANISM: Homo sapiens

<400> SEQUENCE: 162

Met Trp Phe Leu Ile Ser Phe Trp Ala
1               5

<210> SEQ ID NO 163
<211> LENGTH: 9
<212> TYPE: PRT
<213> ORGANISM: Homo sapiens

<400> SEQUENCE: 163

Met Trp Phe Leu Ile His Phe Trp Gly
1               5

<210> SEQ ID NO 164
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Nle

<400> SEQUENCE: 164

Leu Trp Phe Leu Ile Cys Phe Trp Gly
1               5

<210> SEQ ID NO 165
<211> LENGTH: 9
<212> TYPE: PRT
<213> ORGANISM: Homo sapiens

<400> SEQUENCE: 165

Met Trp Ile Leu Ile Ser Phe Trp Gly
1               5

<210> SEQ ID NO 166
<211> LENGTH: 12
<212> TYPE: PRT
<213> ORGANISM: Homo sapiens

<400> SEQUENCE: 166

Met Ile Arg Met Trp Phe Leu Ile Cys Ala Trp Gly
1               5                   10

<210> SEQ ID NO 167
<211> LENGTH: 10
<212> TYPE: PRT
<213> ORGANISM: Homo sapiens

<400> SEQUENCE: 167

Lys Met Trp Phe Leu Ile Cys Ala Trp Asp
1               5                   10

<210> SEQ ID NO 168
<211> LENGTH: 9
<212> TYPE: PRT
<213> ORGANISM: Homo sapiens

<400> SEQUENCE: 168
```

Lys Trp Phe Leu Ile Cys Ala Trp Asp
1               5

<210> SEQ ID NO 169
<211> LENGTH: 9
<212> TYPE: PRT
<213> ORGANISM: Homo sapiens

<400> SEQUENCE: 169

Lys Trp Phe Leu Ile Cys Ala Trp Asp
1               5

<210> SEQ ID NO 170
<211> LENGTH: 10
<212> TYPE: PRT
<213> ORGANISM: Homo sapiens

<400> SEQUENCE: 170

Lys Met Trp Phe Leu Ile Cys Phe Trp Asp
1               5                   10

<210> SEQ ID NO 171
<211> LENGTH: 10
<212> TYPE: PRT
<213> ORGANISM: Homo sapiens

<400> SEQUENCE: 171

Lys Met Trp Phe Leu Ile Ser Phe Trp Asp
1               5                   10

<210> SEQ ID NO 172
<211> LENGTH: 9
<212> TYPE: PRT
<213> ORGANISM: Homo sapiens

<400> SEQUENCE: 172

Lys Trp Phe Leu Ile Cys Phe Trp Asp
1               5

<210> SEQ ID NO 173
<211> LENGTH: 9
<212> TYPE: PRT
<213> ORGANISM: Homo sapiens

<400> SEQUENCE: 173

Lys Trp Phe Leu Ile Cys Glu Trp Gly
1               5

<210> SEQ ID NO 174
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Lys(Gly)

<400> SEQUENCE: 174

Lys Trp Phe Leu Ile Cys Phe Trp Glu Gly
1               5                   10

<210> SEQ ID NO 175
<211> LENGTH: 10
<212> TYPE: PRT
<213> ORGANISM: Homo sapiens

```
<400> SEQUENCE: 175

Asp Trp Phe Leu Ile Cys Phe Trp Lys Gly
1               5                   10

<210> SEQ ID NO 176
<211> LENGTH: 10
<212> TYPE: PRT
<213> ORGANISM: Homo sapiens

<400> SEQUENCE: 176

Asp Trp Phe Leu Ile Cys Phe Trp Lys Gly
1               5                   10

<210> SEQ ID NO 177
<211> LENGTH: 11
<212> TYPE: PRT
<213> ORGANISM: Homo sapiens

<400> SEQUENCE: 177

Asp Met Trp Phe Leu Ile Cys Phe Trp Lys Gly
1               5                   10

<210> SEQ ID NO 178
<211> LENGTH: 10
<212> TYPE: PRT
<213> ORGANISM: Homo sapiens

<400> SEQUENCE: 178

Asp Trp Phe Leu Ile Cys Ala Trp Lys Gly
1               5                   10

<210> SEQ ID NO 179
<211> LENGTH: 9
<212> TYPE: PRT
<213> ORGANISM: Homo sapiens

<400> SEQUENCE: 179

Lys Trp Phe Leu Ile Cys Phe Trp Glu
1               5

<210> SEQ ID NO 180
<211> LENGTH: 10
<212> TYPE: PRT
<213> ORGANISM: Homo sapiens

<400> SEQUENCE: 180

Lys Met Trp Phe Leu Ile Cys Glu Trp Gly
1               5                   10

<210> SEQ ID NO 181
<211> LENGTH: 9
<212> TYPE: PRT
<213> ORGANISM: Homo sapiens

<400> SEQUENCE: 181

Lys Trp Phe Leu Ile Cys Glu Trp Gly
1               5

<210> SEQ ID NO 182
<211> LENGTH: 9
<212> TYPE: PRT
<213> ORGANISM: Homo sapiens

<400> SEQUENCE: 182
```

```
Lys Trp Ile Leu Ile Ser Phe Trp Glu
1               5

<210> SEQ ID NO 183
<211> LENGTH: 9
<212> TYPE: PRT
<213> ORGANISM: Homo sapiens

<400> SEQUENCE: 183

Lys Trp Phe Leu Ile Ser Ala Trp Glu
1               5

<210> SEQ ID NO 184
<211> LENGTH: 9
<212> TYPE: PRT
<213> ORGANISM: Homo sapiens

<400> SEQUENCE: 184

Lys Trp Ile Leu Ile Ser Ala Trp Glu
1               5

<210> SEQ ID NO 185
<211> LENGTH: 9
<212> TYPE: PRT
<213> ORGANISM: Homo sapiens

<400> SEQUENCE: 185

Lys Trp Phe Leu Ile Cys Phe Trp Glu
1               5

<210> SEQ ID NO 186
<211> LENGTH: 10
<212> TYPE: PRT
<213> ORGANISM: Homo sapiens

<400> SEQUENCE: 186

Lys Met Trp Phe Leu Ile Cys Phe Trp Glu
1               5                   10

<210> SEQ ID NO 187
<211> LENGTH: 9
<212> TYPE: PRT
<213> ORGANISM: Homo sapiens

<400> SEQUENCE: 187

Lys Trp Phe Leu Ile Ser Ala Trp Glu
1               5

<210> SEQ ID NO 188
<211> LENGTH: 9
<212> TYPE: PRT
<213> ORGANISM: Homo sapiens

<400> SEQUENCE: 188

Lys Trp Ile Leu Ile Ser Ala Trp Glu
1               5

<210> SEQ ID NO 189
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ahx
```

<400> SEQUENCE: 189

Xaa Met Trp Phe Leu Ile Cys Phe Trp Asp
1               5                   10

<210> SEQ ID NO 190
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ado

<400> SEQUENCE: 190

Xaa Met Trp Phe Leu Ile Cys Phe Trp Asp
1               5                   10

<210> SEQ ID NO 191
<211> LENGTH: 9
<212> TYPE: PRT
<213> ORGANISM: Homo sapiens

<400> SEQUENCE: 191

Met Trp Phe Leu Ile Cys Ala Trp Asp
1               5

<210> SEQ ID NO 192
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ahx

<400> SEQUENCE: 192

Xaa Met Trp Phe Leu Ile Cys Ala Trp Asp
1               5                   10

<210> SEQ ID NO 193
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ado

<400> SEQUENCE: 193

Xaa Met Trp Phe Leu Ile Cys Ala Trp Asp
1               5                   10

<210> SEQ ID NO 194
<211> LENGTH: 8
<212> TYPE: PRT
<213> ORGANISM: Homo sapiens

<400> SEQUENCE: 194

Trp Phe Leu Ile Cys Phe Trp Gly
1               5

<210> SEQ ID NO 195
<211> LENGTH: 8
<212> TYPE: PRT
<213> ORGANISM: Homo sapiens

<400> SEQUENCE: 195

```
Trp Ile Leu Ile Ser Phe Trp Gly
1               5

<210> SEQ ID NO 196
<211> LENGTH: 8
<212> TYPE: PRT
<213> ORGANISM: Homo sapiens

<400> SEQUENCE: 196

Trp Phe Leu Ile Ala Phe Trp Gly
1               5

<210> SEQ ID NO 197
<211> LENGTH: 8
<212> TYPE: PRT
<213> ORGANISM: Homo sapiens

<400> SEQUENCE: 197

Met Trp Phe Leu Ile Cys Phe Trp
1               5

<210> SEQ ID NO 198
<211> LENGTH: 9
<212> TYPE: PRT
<213> ORGANISM: Homo sapiens

<400> SEQUENCE: 198

Met Trp Phe Leu Ile Cys Phe Trp Gly
1               5

<210> SEQ ID NO 199
<211> LENGTH: 9
<212> TYPE: PRT
<213> ORGANISM: Homo sapiens

<400> SEQUENCE: 199

Lys Trp Phe Leu Ile Ser Phe Trp Glu
1               5

<210> SEQ ID NO 200
<211> LENGTH: 9
<212> TYPE: PRT
<213> ORGANISM: Homo sapiens

<400> SEQUENCE: 200

Lys Trp Phe Leu Ile Ala Phe Trp Glu
1               5

<210> SEQ ID NO 201
<211> LENGTH: 9
<212> TYPE: PRT
<213> ORGANISM: Homo sapiens

<400> SEQUENCE: 201

Lys Trp Phe Leu Ile Ala Phe Trp Glu
1               5

<210> SEQ ID NO 202
<211> LENGTH: 9
<212> TYPE: PRT
<213> ORGANISM: Homo sapiens

<400> SEQUENCE: 202

Lys Trp Phe Leu Ile Ser Ala Trp Asp
```

```
1               5
```

<210> SEQ ID NO 203
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Cha

<400> SEQUENCE: 203

```
Lys Trp Ala Leu Ile Ser Ala Trp Asp
1               5
```

<210> SEQ ID NO 204
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Chg

<400> SEQUENCE: 204

```
Lys Trp Gly Leu Ile Ser Ala Trp Asp
1               5
```

<210> SEQ ID NO 205
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Tle

<400> SEQUENCE: 205

```
Lys Trp Xaa Leu Ile Ser Ala Trp Asp
1               5
```

<210> SEQ ID NO 206
<211> LENGTH: 9
<212> TYPE: PRT
<213> ORGANISM: Homo sapiens

<400> SEQUENCE: 206

```
Lys Trp Leu Leu Ile Ser Ala Trp Asp
1               5
```

<210> SEQ ID NO 207
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Lys(Gly)

<400> SEQUENCE: 207

```
Lys Trp Phe Leu Ile Cys Ala Trp Asp
1               5
```

<210> SEQ ID NO 208
<211> LENGTH: 9
<212> TYPE: PRT
<213> ORGANISM: Homo sapiens

```
<400> SEQUENCE: 208

Lys Trp Phe Glu Ile Ser Phe Trp Gly
1               5

<210> SEQ ID NO 209
<211> LENGTH: 9
<212> TYPE: PRT
<213> ORGANISM: Homo sapiens

<400> SEQUENCE: 209

Ala Trp Phe Leu Ile Ser Phe Trp Gly
1               5

<210> SEQ ID NO 210
<211> LENGTH: 9
<212> TYPE: PRT
<213> ORGANISM: Homo sapiens

<400> SEQUENCE: 210

Met Ala Phe Leu Ile Ser Phe Trp Gly
1               5

<210> SEQ ID NO 211
<211> LENGTH: 9
<212> TYPE: PRT
<213> ORGANISM: Homo sapiens

<400> SEQUENCE: 211

Met Trp Phe Leu Ile Cys Ala Trp Gly
1               5

<210> SEQ ID NO 212
<211> LENGTH: 9
<212> TYPE: PRT
<213> ORGANISM: Homo sapiens

<400> SEQUENCE: 212

Met Trp Phe Leu Ile Ala Ala Trp Gly
1               5

<210> SEQ ID NO 213
<211> LENGTH: 9
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Nme-G

<400> SEQUENCE: 213

Met Trp Phe Leu Ile Cys Phe Trp Gly
1               5

<210> SEQ ID NO 214
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Cys(Me)

<400> SEQUENCE: 214

Met Trp Phe Leu Ile Cys Phe Trp Gly
1               5
```

```
<210> SEQ ID NO 215
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (4)..(4)
<223> OTHER INFORMATION: Cha
<220> FEATURE:
<221> NAME/KEY: MOD_RES
<222> LOCATION: (7)..(7)
<223> OTHER INFORMATION: Abu

<400> SEQUENCE: 215

Lys Leu Trp Ala Leu Ile Xaa Ala Trp Asp
1               5                   10

<210> SEQ ID NO 216
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Cha

<400> SEQUENCE: 216

Met Trp Ala Leu Ile Ser Phe Trp Gly
1               5

<210> SEQ ID NO 217
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Chg

<400> SEQUENCE: 217

Met Trp Gly Leu Ile Ser Phe Trp Gly
1               5

<210> SEQ ID NO 218
<211> LENGTH: 9
<212> TYPE: PRT
<213> ORGANISM: Homo sapiens

<400> SEQUENCE: 218

Met Trp Leu Leu Ile Ser Phe Trp Gly
1               5

<210> SEQ ID NO 219
<211> LENGTH: 9
<212> TYPE: PRT
<213> ORGANISM: Homo sapiens

<400> SEQUENCE: 219

Met Trp Phe Leu Ile Ser Phe Trp Gly
1               5

<210> SEQ ID NO 220
<211> LENGTH: 8
<212> TYPE: PRT
```

```
<213> ORGANISM: Homo sapiens

<400> SEQUENCE: 220

Trp Phe Leu Ile Ser Phe Trp Gly
1               5

<210> SEQ ID NO 221
<211> LENGTH: 9
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Nme-Gly

<400> SEQUENCE: 221

Met Trp Ile Leu Ile Ser Phe Trp Gly
1               5

<210> SEQ ID NO 222
<211> LENGTH: 9
<212> TYPE: PRT
<213> ORGANISM: Homo sapiens

<400> SEQUENCE: 222

Met Trp Ile Leu Ile Ser Phe Trp Gly
1               5

<210> SEQ ID NO 223
<211> LENGTH: 9
<212> TYPE: PRT
<213> ORGANISM: Homo sapiens

<400> SEQUENCE: 223

Met Trp Ile Leu Ile Ser Phe Trp Gly
1               5

<210> SEQ ID NO 224
<211> LENGTH: 9
<212> TYPE: PRT
<213> ORGANISM: Homo sapiens

<400> SEQUENCE: 224

Met Trp Ile Leu Ile Ser Phe Trp Gly
1               5

<210> SEQ ID NO 225
<211> LENGTH: 9
<212> TYPE: PRT
<213> ORGANISM: Homo sapiens

<400> SEQUENCE: 225

Met Trp Ile Leu Ile Ser Phe Trp Gly
1               5

<210> SEQ ID NO 226
<211> LENGTH: 9
<212> TYPE: PRT
<213> ORGANISM: Homo sapiens

<400> SEQUENCE: 226

Lys Trp Phe Leu Ile Ser Phe Trp Glu
1               5

<210> SEQ ID NO 227
```

<211> LENGTH: 9
<212> TYPE: PRT
<213> ORGANISM: Homo sapiens

<400> SEQUENCE: 227

Lys Trp Phe Leu Ile Ser Phe Glu Gly
1               5

<210> SEQ ID NO 228
<211> LENGTH: 9
<212> TYPE: PRT
<213> ORGANISM: Homo sapiens

<400> SEQUENCE: 228

Lys Trp Phe Leu Ile Ser Glu Trp Gly
1               5

<210> SEQ ID NO 229
<211> LENGTH: 9
<212> TYPE: PRT
<213> ORGANISM: Homo sapiens

<400> SEQUENCE: 229

Lys Trp Phe Leu Ile Glu Phe Trp Gly
1               5

<210> SEQ ID NO 230
<211> LENGTH: 9
<212> TYPE: PRT
<213> ORGANISM: Homo sapiens

<400> SEQUENCE: 230

Met Trp Lys Leu Ile Glu Phe Trp Gly
1               5

<210> SEQ ID NO 231
<211> LENGTH: 9
<212> TYPE: PRT
<213> ORGANISM: Homo sapiens

<400> SEQUENCE: 231

Lys Trp Phe Leu Glu Ser Phe Trp Gly
1               5

<210> SEQ ID NO 232
<211> LENGTH: 9
<212> TYPE: PRT
<213> ORGANISM: Homo sapiens

<400> SEQUENCE: 232

Lys Trp Glu Leu Ile Ser Phe Trp Gly
1               5

<210> SEQ ID NO 233
<211> LENGTH: 9
<212> TYPE: PRT
<213> ORGANISM: Homo sapiens

<400> SEQUENCE: 233

Asp Trp Phe Leu Ile Cys Ala Trp Lys
1               5

<210> SEQ ID NO 234
<211> LENGTH: 9
<212> TYPE: PRT

```
<213> ORGANISM: Homo sapiens
<220> FEATURE:
<221> NAME/KEY: MOD_RES
<222> LOCATION: (9)..(9)
<223> OTHER INFORMATION: Beta-Ala

<400> SEQUENCE: 234

Lys Trp Phe Leu Ile Cys Ala Trp Ala
1               5

<210> SEQ ID NO 235
<211> LENGTH: 9
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Beta-Ala

<400> SEQUENCE: 235

Lys Trp Phe Leu Ile Cys Ala Trp Ala
1               5

<210> SEQ ID NO 236
<211> LENGTH: 9
<212> TYPE: PRT
<213> ORGANISM: Homo sapiens

<400> SEQUENCE: 236

Lys Trp Phe Leu Ile Cys Ala Trp Asp
1               5

<210> SEQ ID NO 237
<211> LENGTH: 6
<212> TYPE: PRT
<213> ORGANISM: Homo sapiens

<400> SEQUENCE: 237

Leu Ile Ser Phe Trp Gly
1               5

<210> SEQ ID NO 238
<211> LENGTH: 6
<212> TYPE: PRT
<213> ORGANISM: Homo sapiens

<400> SEQUENCE: 238

Leu Ile Ser Phe Trp Gly
1               5

<210> SEQ ID NO 239
<211> LENGTH: 7
<212> TYPE: PRT
<213> ORGANISM: Homo sapiens

<400> SEQUENCE: 239

Phe Leu Ile Ser Phe Trp Gly
1               5

<210> SEQ ID NO 240
<211> LENGTH: 8
<212> TYPE: PRT
<213> ORGANISM: Homo sapiens

<400> SEQUENCE: 240

Met Trp Ile Leu Ile Ser Phe Trp
```

```
1               5

<210> SEQ ID NO 241
<211> LENGTH: 7
<212> TYPE: PRT
<213> ORGANISM: Homo sapiens

<400> SEQUENCE: 241

Phe Leu Ile Ser Phe Trp Gly
1               5

<210> SEQ ID NO 242
<211> LENGTH: 9
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Beta-Ala

<400> SEQUENCE: 242

Met Trp Ile Leu Ile Ser Phe Trp Ala
1               5

<210> SEQ ID NO 243
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Abu

<400> SEQUENCE: 243

Lys Trp Phe Leu Ile Xaa Ala Trp Asp
1               5

<210> SEQ ID NO 244
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Abu

<400> SEQUENCE: 244

Lys Trp Phe Leu Ile Xaa Ala Trp Asp
1               5

<210> SEQ ID NO 245
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ahx

<400> SEQUENCE: 245

Xaa Trp Phe Leu Ile Cys Ala Trp Asp
1               5

<210> SEQ ID NO 246
<211> LENGTH: 9
<212> TYPE: PRT
<213> ORGANISM: Homo sapiens
<220> FEATURE:
```

```
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (6)..(6)
<223> OTHER INFORMATION: Abu

<400> SEQUENCE: 246

Xaa Trp Phe Leu Ile Xaa Ala Trp Asp
1               5

<210> SEQ ID NO 247
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Lys(GABA); wherein the Lys is modified on the
      side chain

<400> SEQUENCE: 247

Lys Trp Phe Leu Ile Cys Ala Trp Asp
1               5

<210> SEQ ID NO 248
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Lys(Ava); wherein the Lys is modified on the
      side chain

<400> SEQUENCE: 248

Lys Trp Phe Leu Ile Cys Ala Trp Asp
1               5

<210> SEQ ID NO 249
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Lys(Ahx); wherein the Lys is modified on the
      side chain

<400> SEQUENCE: 249

Lys Trp Phe Leu Ile Cys Ala Trp Asp
1               5

<210> SEQ ID NO 250
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Adc

<400> SEQUENCE: 250

Xaa Trp Phe Leu Ile Cys Ala Trp
1               5

<210> SEQ ID NO 251
<211> LENGTH: 7
```

```
<212> TYPE: PRT
<213> ORGANISM: Homo sapiens

<400> SEQUENCE: 251

Lys Leu Ile Ala Phe Trp Asp
1               5

<210> SEQ ID NO 252
<211> LENGTH: 7
<212> TYPE: PRT
<213> ORGANISM: Homo sapiens

<400> SEQUENCE: 252

Lys Leu Ile Ala Phe Trp Asp
1               5

<210> SEQ ID NO 253
<211> LENGTH: 8
<212> TYPE: PRT
<213> ORGANISM: Homo sapiens

<400> SEQUENCE: 253

Lys Phe Leu Ile Ala Phe Trp Asp
1               5

<210> SEQ ID NO 254
<211> LENGTH: 8
<212> TYPE: PRT
<213> ORGANISM: Homo sapiens

<400> SEQUENCE: 254

Lys Phe Leu Ile Ala Phe Trp Asp
1               5

<210> SEQ ID NO 255
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Cha

<400> SEQUENCE: 255

Lys Trp Ala Leu Ile Ser Ala Trp Asp
1               5

<210> SEQ ID NO 256
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Ava

<400> SEQUENCE: 256

Met Trp Phe Leu Ile Xaa Trp Gly
1               5

<210> SEQ ID NO 257
<211> LENGTH: 8
<212> TYPE: PRT
<213> ORGANISM: Homo sapiens
<220> FEATURE:
<221> NAME/KEY: MOD_RES
<222> LOCATION: (6)..(6)
```

```
<223> OTHER INFORMATION: Ava

<400> SEQUENCE: 257

Met Trp Phe Leu Ile Xaa Trp Gly
1               5

<210> SEQ ID NO 258
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Abu
<220> FEATURE:
<221> NAME/KEY: MOD_RES
<222> LOCATION: (9)..(9)
<223> OTHER INFORMATION: Nme-Gly

<400> SEQUENCE: 258

Met Trp Phe Leu Ile Xaa Phe Trp Gly
1               5

<210> SEQ ID NO 259
<211> LENGTH: 9
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Abu
<220> FEATURE:
<221> NAME/KEY: MOD_RES
<222> LOCATION: (9)..(9)
<223> OTHER INFORMATION: Nme-Gly

<400> SEQUENCE: 259

Met Trp Phe Leu Ile Xaa Phe Trp Gly
1               5

<210> SEQ ID NO 260
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Lys(Beta-Ala); wherein the Lys is modified on
      the side chain

<400> SEQUENCE: 260

Lys Trp Phe Leu Ile Cys Ala Trp Asp
1               5

<210> SEQ ID NO 261
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Cha
<220> FEATURE:
<221> NAME/KEY: MOD_RES
<222> LOCATION: (6)..(6)
<223> OTHER INFORMATION: Abu

<400> SEQUENCE: 261

Lys Trp Ala Leu Ile Xaa Ala Trp Asp
1               5
```

```
<210> SEQ ID NO 262
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Chg
<220> FEATURE:
<221> NAME/KEY: MOD_RES
<222> LOCATION: (6)..(6)
<223> OTHER INFORMATION: Abu

<400> SEQUENCE: 262

Lys Trp Gly Leu Ile Xaa Ala Trp Asp
1               5

<210> SEQ ID NO 263
<211> LENGTH: 8
<212> TYPE: PRT
<213> ORGANISM: Homo sapiens

<400> SEQUENCE: 263

Trp Ile Leu Ile Ala Phe Trp Gly
1               5

<210> SEQ ID NO 264
<211> LENGTH: 9
<212> TYPE: PRT
<213> ORGANISM: Homo sapiens

<400> SEQUENCE: 264

Met Trp Ile Leu Ile Ser Phe Trp Gly
1               5

<210> SEQ ID NO 265
<211> LENGTH: 8
<212> TYPE: PRT
<213> ORGANISM: Homo sapiens

<400> SEQUENCE: 265

Trp Ile Leu Ile Ala Phe Trp Gly
1               5

<210> SEQ ID NO 266
<211> LENGTH: 46
<212> TYPE: PRT
<213> ORGANISM: Homo sapiens

<400> SEQUENCE: 266

Gly Gly Gly Asp Asp Leu Gly Ala Asn Asp Glu Leu Ile Ser Phe Lys
1               5                   10                  15

Asp Glu Gly Glu Gln Glu Glu Lys Ser Ser Glu Asn Ser Ser Ala Glu
            20                  25                  30

Arg Asp Leu Ala Asp Val Lys Ser Ser Leu Val Asn Glu Lys
        35                  40                  45

<210> SEQ ID NO 267
<211> LENGTH: 46
<212> TYPE: PRT
<213> ORGANISM: Homo sapiens
<220> FEATURE:
<221> NAME/KEY: MOD_RES
<222> LOCATION: (46)..(46)
<223> OTHER INFORMATION: Lys(FITC)
```

<400> SEQUENCE: 267

Gly Gly Gly Asp Leu Gly Ala Asn Asp Glu Leu Ile Ser Phe Lys
1               5                   10                  15

Asp Glu Gly Glu Gln Glu Glu Lys Ser Ser Glu Asn Ser Ser Ala Glu
                20                  25                  30

Arg Asp Leu Ala Asp Val Lys Ser Ser Leu Val Asn Glu Lys
            35                  40                  45

<210> SEQ ID NO 268
<211> LENGTH: 56
<212> TYPE: PRT
<213> ORGANISM: Homo sapiens

<400> SEQUENCE: 268

Asp Thr Asp Pro Thr Ala Pro Pro Tyr Asp Ser Leu Leu Val Phe Asp
1               5                   10                  15

Tyr Glu Gly Ser Gly Ser Glu Ala Ala Ser Leu Ser Ser Leu Asn Ser
                20                  25                  30

Ser Glu Ser Asp Lys Asp Gln Asp Tyr Asp Tyr Leu Asn Glu Trp Gly
            35                  40                  45

Asn Arg Phe Lys Lys Leu Ala Lys
        50                  55

<210> SEQ ID NO 269
<211> LENGTH: 56
<212> TYPE: PRT
<213> ORGANISM: Homo sapiens

<400> SEQUENCE: 269

Asp Thr Asp Pro Thr Ala Pro Pro Tyr Asp Ser Leu Leu Val Phe Asp
1               5                   10                  15

Tyr Glu Gly Ser Gly Ser Glu Ala Ala Ser Leu Ser Ser Leu Asn Ser
                20                  25                  30

Ser Glu Ser Asp Lys Asp Gln Asp Tyr Asp Tyr Leu Asn Glu Trp Gly
            35                  40                  45

Asn Arg Phe Lys Lys Leu Ala Lys
        50                  55

<210> SEQ ID NO 270
<211> LENGTH: 38
<212> TYPE: PRT
<213> ORGANISM: Homo sapiens
<220> FEATURE:
<221> NAME/KEY: MOD_RES
<222> LOCATION: (36)..(37)
<223> OTHER INFORMATION: Beta-Ala

<400> SEQUENCE: 270

Asn Pro Asp Gly Leu Ser Gln Glu Gln Leu Glu His Arg Glu Arg Ser
1               5                   10                  15

Leu Gln Thr Leu Arg Asp Ile Gln Arg Met Leu Phe Pro Asp Glu Lys
                20                  25                  30

Glu Phe Thr Ala Ala Lys
            35

<210> SEQ ID NO 271
<211> LENGTH: 38
<212> TYPE: PRT
<213> ORGANISM: Homo sapiens
<220> FEATURE:

```
<221> NAME/KEY: MOD_RES
<222> LOCATION: (36)..(37)
<223> OTHER INFORMATION: Beta-Ala

<400> SEQUENCE: 271

Asn Pro Asp Gly Leu Ser Gln Glu Gln Leu Glu His Arg Glu Arg Ser
1               5                   10                  15

Leu Gln Thr Leu Arg Asp Ile Gln Arg Met Leu Phe Pro Asp Glu Lys
            20                  25                  30

Glu Phe Thr Ala Ala Lys
        35

<210> SEQ ID NO 272
<211> LENGTH: 10
<212> TYPE: PRT
<213> ORGANISM: Homo sapiens

<400> SEQUENCE: 272

Lys Trp Phe Leu Ile Cys Phe Trp Glu Gly
1               5                   10

<210> SEQ ID NO 273
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Lys(Gly); wherein the Lys is modified on the
      side chain

<400> SEQUENCE: 273

Lys Trp Phe Leu Ile Cys Phe Trp Glu Gly
1               5                   10

<210> SEQ ID NO 274
<211> LENGTH: 9
<212> TYPE: PRT
<213> ORGANISM: Homo sapiens

<400> SEQUENCE: 274

Met Trp Phe Leu Ile Ala Phe Trp Gly
1               5

<210> SEQ ID NO 275
<211> LENGTH: 11
<212> TYPE: PRT
<213> ORGANISM: Homo sapiens

<400> SEQUENCE: 275

Arg Ser Arg His Trp Phe Leu Ile Ser Phe Trp
1               5                   10

<210> SEQ ID NO 276
<211> LENGTH: 11
<212> TYPE: PRT
<213> ORGANISM: Homo sapiens

<400> SEQUENCE: 276

Arg Ser Arg Trp Trp Phe Leu Ile Ser Phe Trp
1               5                   10

<210> SEQ ID NO 277
<211> LENGTH: 11
<212> TYPE: PRT
```

```
<213> ORGANISM: Homo sapiens
<220> FEATURE:
<221> NAME/KEY: MOD_RES
<222> LOCATION: (1)..(1)
<223> OTHER INFORMATION: Orn

<400> SEQUENCE: 277

Xaa Ser Arg Met Trp Tyr Leu Ile Ser Phe Trp
1               5                   10

<210> SEQ ID NO 278
<211> LENGTH: 12
<212> TYPE: PRT
<213> ORGANISM: Homo sapiens

<400> SEQUENCE: 278

Lys Ser Arg Met Trp Phe Leu Ile Ser Phe Trp Gly
1               5                   10

<210> SEQ ID NO 279
<211> LENGTH: 12
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Beta-Ala

<400> SEQUENCE: 279

Lys Ala Ser Arg Met Trp Phe Leu Ile Ser Phe Trp
1               5                   10

<210> SEQ ID NO 280
<211> LENGTH: 9
<212> TYPE: PRT
<213> ORGANISM: Homo sapiens

<400> SEQUENCE: 280

Arg Lys Lys Arg Arg Gln Arg Arg Arg
1               5

<210> SEQ ID NO 281
<211> LENGTH: 9
<212> TYPE: PRT
<213> ORGANISM: Homo sapiens

<400> SEQUENCE: 281

Arg Lys Lys Arg Arg Gln Arg Arg Arg
1               5

<210> SEQ ID NO 282
<211> LENGTH: 9
<212> TYPE: PRT
<213> ORGANISM: Homo sapiens

<400> SEQUENCE: 282

Arg Lys Lys Arg Arg Gln Arg Arg Arg
1               5

<210> SEQ ID NO 283
<211> LENGTH: 7
<212> TYPE: PRT
<213> ORGANISM: Homo sapiens

<400> SEQUENCE: 283

Pro Lys Lys Lys Arg Lys Val
```

```
1               5

<210> SEQ ID NO 284
<211> LENGTH: 10
<212> TYPE: PRT
<213> ORGANISM: Homo sapiens

<400> SEQUENCE: 284

Lys Trp Phe Leu Ile Cys Ala Trp Asn Gly
1               5                   10

<210> SEQ ID NO 285
<211> LENGTH: 7
<212> TYPE: PRT
<213> ORGANISM: Homo sapiens

<400> SEQUENCE: 285

Pro Lys Lys Lys Arg Lys Val
1               5

<210> SEQ ID NO 286
<211> LENGTH: 7
<212> TYPE: PRT
<213> ORGANISM: Homo sapiens

<400> SEQUENCE: 286

Pro Lys Lys Lys Arg Lys Val
1               5

<210> SEQ ID NO 287
<211> LENGTH: 7
<212> TYPE: PRT
<213> ORGANISM: Homo sapiens

<400> SEQUENCE: 287

Pro Lys Lys Lys Arg Lys Val
1               5

<210> SEQ ID NO 288
<211> LENGTH: 17
<212> TYPE: PRT
<213> ORGANISM: Homo sapiens

<400> SEQUENCE: 288

Pro Lys Lys Lys Arg Lys Val Gly Met Trp Phe Leu Ile Cys Phe Trp
1               5                   10                  15

Gly

<210> SEQ ID NO 289
<211> LENGTH: 7
<212> TYPE: PRT
<213> ORGANISM: Homo sapiens

<400> SEQUENCE: 289

Pro Lys Lys Lys Arg Lys Val
1               5

<210> SEQ ID NO 290
<211> LENGTH: 17
<212> TYPE: PRT
<213> ORGANISM: Homo sapiens

<400> SEQUENCE: 290

Pro Lys Lys Lys Arg Lys Val Gly Met Trp Ile Leu Ile Ser Phe Trp
```

-continued

```
1               5                   10                  15

Gly

<210> SEQ ID NO 291
<211> LENGTH: 12
<212> TYPE: PRT
<213> ORGANISM: Homo sapiens

<400> SEQUENCE: 291

Lys Met Ser Arg Met Asp Tyr Leu Ile Ser Phe Trp
1               5                   10

<210> SEQ ID NO 292
<211> LENGTH: 12
<212> TYPE: PRT
<213> ORGANISM: Homo sapiens

<400> SEQUENCE: 292

Lys Met Ser Arg Met Asp Glu Leu Ile Ser Phe Trp
1               5                   10

<210> SEQ ID NO 293
<211> LENGTH: 9
<212> TYPE: PRT
<213> ORGANISM: Homo sapiens

<400> SEQUENCE: 293

Lys Asp Phe Leu Ile Ala Phe Trp Asp
1               5

<210> SEQ ID NO 294
<211> LENGTH: 9
<212> TYPE: PRT
<213> ORGANISM: Homo sapiens

<400> SEQUENCE: 294

Lys Asp Glu Leu Ile Ala Phe Trp Asp
1               5

<210> SEQ ID NO 295
<211> LENGTH: 9
<212> TYPE: PRT
<213> ORGANISM: Homo sapiens

<400> SEQUENCE: 295

Met Asp Phe Leu Ile Ser Phe Trp Gly
1               5

<210> SEQ ID NO 296
<211> LENGTH: 9
<212> TYPE: PRT
<213> ORGANISM: Homo sapiens

<400> SEQUENCE: 296

Met Asp Glu Leu Ile Ser Phe Trp Gly
1               5

<210> SEQ ID NO 297
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Nme-Ala
```

```
<400> SEQUENCE: 297

Met Trp Ala Trp Leu Ser Arg Gln Trp Ile Val Gly
1               5                   10

<210> SEQ ID NO 298
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala

<400> SEQUENCE: 298

Met Ala Glu Ser Ile Leu Asp Glu His Val Gln Arg Val Trp Gly
1               5                   10                  15

<210> SEQ ID NO 299
<211> LENGTH: 15
<212> TYPE: PRT
<213> ORGANISM: Homo sapiens

<400> SEQUENCE: 299

Met Tyr Glu Ser Ile Leu Asp Glu His Met Gln Arg Val Trp Gly
1               5                   10                  15

<210> SEQ ID NO 300
<211> LENGTH: 15
<212> TYPE: PRT
<213> ORGANISM: Homo sapiens

<400> SEQUENCE: 300

Met Pro Glu Ser Ile Leu Asp Glu His Val Gln Arg Val Trp Gly
1               5                   10                  15

<210> SEQ ID NO 301
<211> LENGTH: 15
<212> TYPE: PRT
<213> ORGANISM: Homo sapiens

<400> SEQUENCE: 301

Met Trp Glu Ser Ile Leu Asp Glu His Met Gln Arg Val Trp Gly
1               5                   10                  15

<210> SEQ ID NO 302
<211> LENGTH: 18
<212> TYPE: PRT
<213> ORGANISM: Homo sapiens

<400> SEQUENCE: 302

Met Tyr Glu Ser Ile Leu Asp Glu His Val Gln Arg Val Trp Gly Ile
1               5                   10                  15

Leu Arg

<210> SEQ ID NO 303
<211> LENGTH: 18
<212> TYPE: PRT
<213> ORGANISM: Homo sapiens

<400> SEQUENCE: 303

Met Trp Glu Ser Ile Leu Asp Glu His Val Gln Arg Val Trp Gly Ile
1               5                   10                  15

Leu Arg
```

```
<210> SEQ ID NO 304
<211> LENGTH: 15
<212> TYPE: PRT
<213> ORGANISM: Homo sapiens

<400> SEQUENCE: 304

Met Tyr Glu Ser Ile Leu Asp Glu His Val Gln Arg Val Trp Gly
1               5                   10                  15

<210> SEQ ID NO 305
<211> LENGTH: 15
<212> TYPE: PRT
<213> ORGANISM: Homo sapiens

<400> SEQUENCE: 305

Met Trp Glu Ser Ile Leu Asp Glu His Val Lys Arg Val Trp Gly
1               5                   10                  15

<210> SEQ ID NO 306
<211> LENGTH: 15
<212> TYPE: PRT
<213> ORGANISM: Homo sapiens

<400> SEQUENCE: 306

Met Trp Glu Ser Ile Leu Asp Glu His Val Gln Arg Val Trp Gly
1               5                   10                  15

<210> SEQ ID NO 307
<211> LENGTH: 13
<212> TYPE: PRT
<213> ORGANISM: Homo sapiens

<400> SEQUENCE: 307

Lys Met Ser Arg Met Trp Phe Leu Ile Ser Phe Trp Gly
1               5                   10

<210> SEQ ID NO 308
<211> LENGTH: 10
<212> TYPE: PRT
<213> ORGANISM: Homo sapiens

<400> SEQUENCE: 308

Lys Met Trp Phe Leu Ile Cys Phe Trp Gly
1               5                   10

<210> SEQ ID NO 309
<211> LENGTH: 14
<212> TYPE: PRT
<213> ORGANISM: Homo sapiens

<400> SEQUENCE: 309

Lys Met Ser Arg Met Trp Phe Leu Ile Ser Phe Trp Thr Gly
1               5                   10

<210> SEQ ID NO 310
<211> LENGTH: 11
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Nme-Ala

<400> SEQUENCE: 310
```

```
Lys Met Trp Phe Leu Ile Ser Phe Trp Ala Gly
1               5                   10

<210> SEQ ID NO 311
<211> LENGTH: 13
<212> TYPE: PRT
<213> ORGANISM: Homo sapiens

<400> SEQUENCE: 311

Lys Met Ser Arg Met Trp Phe Leu Ile Cys Phe Trp Gly
1               5                   10

<210> SEQ ID NO 312
<211> LENGTH: 11
<212> TYPE: PRT
<213> ORGANISM: Homo sapiens

<400> SEQUENCE: 312

Lys Met Trp Phe Leu Ile Ser Phe Trp Glu Gly
1               5                   10

<210> SEQ ID NO 313
<211> LENGTH: 13
<212> TYPE: PRT
<213> ORGANISM: Homo sapiens

<400> SEQUENCE: 313

Lys Met Ser Arg Thr Trp Phe Leu Ile Ser Phe Trp Gly
1               5                   10

<210> SEQ ID NO 314
<211> LENGTH: 11
<212> TYPE: PRT
<213> ORGANISM: Homo sapiens

<400> SEQUENCE: 314

Lys Met Trp Phe Leu Ile Ser Phe Trp Arg Gly
1               5                   10

<210> SEQ ID NO 315
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Nme-Ala

<400> SEQUENCE: 315

Lys Met Ser Arg Met Ala Phe Leu Ile Ser Phe Trp Gly
1               5                   10

<210> SEQ ID NO 316
<211> LENGTH: 13
<212> TYPE: PRT
<213> ORGANISM: Homo sapiens

<400> SEQUENCE: 316

Lys Met Ser Arg Met Trp Ile Leu Ile Ser Phe Trp Gly
1               5                   10

<210> SEQ ID NO 317
<211> LENGTH: 14
<212> TYPE: PRT
<213> ORGANISM: Homo sapiens
```

```
<400> SEQUENCE: 317

Lys Met Ser Arg Met Trp Phe Leu Ile Ser Phe Trp Met Gly
1               5                   10

<210> SEQ ID NO 318
<211> LENGTH: 13
<212> TYPE: PRT
<213> ORGANISM: Homo sapiens

<400> SEQUENCE: 318

Lys Met Ser Arg Met Leu Phe Leu Ile Ser Phe Trp Gly
1               5                   10

<210> SEQ ID NO 319
<211> LENGTH: 13
<212> TYPE: PRT
<213> ORGANISM: Homo sapiens

<400> SEQUENCE: 319

Lys Met Ile Arg Met Trp Phe Leu Ile Ser Phe Trp Gly
1               5                   10

<210> SEQ ID NO 320
<211> LENGTH: 13
<212> TYPE: PRT
<213> ORGANISM: Homo sapiens

<400> SEQUENCE: 320

Lys Met Ser Arg Met Trp Phe Leu Ile Ser Ser Trp Gly
1               5                   10

<210> SEQ ID NO 321
<211> LENGTH: 14
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Nme-Ala

<400> SEQUENCE: 321

Lys Met Ser Arg Met Trp Phe Leu Ile Ser Phe Trp Ala Gly
1               5                   10

<210> SEQ ID NO 322
<211> LENGTH: 13
<212> TYPE: PRT
<213> ORGANISM: Homo sapiens

<400> SEQUENCE: 322

Lys Met Ser Arg Ile Trp Phe Leu Ile Ser Phe Trp Gly
1               5                   10

<210> SEQ ID NO 323
<211> LENGTH: 13
<212> TYPE: PRT
<213> ORGANISM: Homo sapiens

<400> SEQUENCE: 323

Lys Met Ser Arg Met Trp Phe Leu Val Ser Phe Trp Gly
1               5                   10

<210> SEQ ID NO 324
<211> LENGTH: 14
<212> TYPE: PRT
```

<213> ORGANISM: Homo sapiens

<400> SEQUENCE: 324

Lys Met Ser Arg Met Trp Phe Leu Ile Ser Phe Trp Glu Gly
1               5                   10

<210> SEQ ID NO 325
<211> LENGTH: 13
<212> TYPE: PRT
<213> ORGANISM: Homo sapiens

<400> SEQUENCE: 325

Lys Met Ser Arg Lys Trp Phe Leu Ile Ser Phe Trp Gly
1               5                   10

<210> SEQ ID NO 326
<211> LENGTH: 13
<212> TYPE: PRT
<213> ORGANISM: Homo sapiens

<400> SEQUENCE: 326

Lys Met Asn Arg Met Trp Phe Leu Ile Ser Phe Trp Gly
1               5                   10

<210> SEQ ID NO 327
<211> LENGTH: 13
<212> TYPE: PRT
<213> ORGANISM: Homo sapiens

<400> SEQUENCE: 327

Lys Met Ser Arg Met Trp Phe Leu Thr Ser Phe Trp Gly
1               5                   10

<210> SEQ ID NO 328
<211> LENGTH: 13
<212> TYPE: PRT
<213> ORGANISM: Homo sapiens

<400> SEQUENCE: 328

Lys Met Ser Arg Met Arg Phe Leu Ile Ser Phe Trp Gly
1               5                   10

<210> SEQ ID NO 329
<211> LENGTH: 13
<212> TYPE: PRT
<213> ORGANISM: Homo sapiens

<400> SEQUENCE: 329

Lys Met Ser Arg Met Trp Phe Leu Phe Ser Phe Trp Gly
1               5                   10

<210> SEQ ID NO 330
<211> LENGTH: 13
<212> TYPE: PRT
<213> ORGANISM: Homo sapiens

<400> SEQUENCE: 330

Lys Met Ser Arg Val Trp Phe Leu Ile Ser Phe Trp Gly
1               5                   10

<210> SEQ ID NO 331
<211> LENGTH: 13
<212> TYPE: PRT
<213> ORGANISM: Homo sapiens

<400> SEQUENCE: 331

Lys Met Ser Arg Met Trp Phe Pro Ile Ser Phe Trp Gly
1               5                   10

<210> SEQ ID NO 332
<211> LENGTH: 13
<212> TYPE: PRT
<213> ORGANISM: Homo sapiens

<400> SEQUENCE: 332

Lys Met Gly Arg Met Trp Phe Leu Ile Ser Phe Trp Gly
1               5                   10

<210> SEQ ID NO 333
<211> LENGTH: 13
<212> TYPE: PRT
<213> ORGANISM: Homo sapiens

<400> SEQUENCE: 333

Lys Met Ser Arg Met Trp Phe Leu Ile Ser Phe Arg Gly
1               5                   10

<210> SEQ ID NO 334
<211> LENGTH: 13
<212> TYPE: PRT
<213> ORGANISM: Homo sapiens

<400> SEQUENCE: 334

Lys Met Ser Arg Met Trp Phe Leu Asn Ser Phe Trp Gly
1               5                   10

<210> SEQ ID NO 335
<211> LENGTH: 13
<212> TYPE: PRT
<213> ORGANISM: Homo sapiens

<400> SEQUENCE: 335

Lys Met Pro Ser Phe Ile Ile Val Leu Thr Val Ile Gly
1               5                   10

<210> SEQ ID NO 336
<211> LENGTH: 13
<212> TYPE: PRT
<213> ORGANISM: Homo sapiens

<400> SEQUENCE: 336

Lys Met Pro Ser Phe Ile Ile Val Leu Thr Leu Ile Gly
1               5                   10

<210> SEQ ID NO 337
<211> LENGTH: 13
<212> TYPE: PRT
<213> ORGANISM: Homo sapiens

<400> SEQUENCE: 337

Lys Met Pro Ser Tyr Ile Ile Val Leu Thr Val Ile Gly
1               5                   10

<210> SEQ ID NO 338
<211> LENGTH: 13
<212> TYPE: PRT
<213> ORGANISM: Homo sapiens

<400> SEQUENCE: 338

```
Lys Met Pro Cys Phe Ile Ile Val Leu Thr Val Ile Gly
1               5                   10

<210> SEQ ID NO 339
<211> LENGTH: 13
<212> TYPE: PRT
<213> ORGANISM: Homo sapiens

<400> SEQUENCE: 339

Lys Met Pro Ser Phe Val Ile Val Leu Thr Val Ile Gly
1               5                   10

<210> SEQ ID NO 340
<211> LENGTH: 13
<212> TYPE: PRT
<213> ORGANISM: Homo sapiens

<400> SEQUENCE: 340

Lys Met Pro Ser Leu Ile Ile Val Leu Thr Val Ile Gly
1               5                   10

<210> SEQ ID NO 341
<211> LENGTH: 14
<212> TYPE: PRT
<213> ORGANISM: Homo sapiens

<400> SEQUENCE: 341

Lys Met Pro Ser Phe Ile Ile Val Leu Thr Val Ile Arg Gly
1               5                   10

<210> SEQ ID NO 342
<211> LENGTH: 13
<212> TYPE: PRT
<213> ORGANISM: Homo sapiens

<400> SEQUENCE: 342

Lys Met Pro Ser Phe Ile Ile Val Leu Ser Val Ile Gly
1               5                   10

<210> SEQ ID NO 343
<211> LENGTH: 14
<212> TYPE: PRT
<213> ORGANISM: Homo sapiens

<400> SEQUENCE: 343

Lys Met Pro Ser Phe Ile Ile Val Leu Thr Val Ile Glu Gly
1               5                   10

<210> SEQ ID NO 344
<211> LENGTH: 13
<212> TYPE: PRT
<213> ORGANISM: Homo sapiens

<400> SEQUENCE: 344

Lys Met Pro Ser Phe Ile Val Val Leu Thr Val Ile Gly
1               5                   10

<210> SEQ ID NO 345
<211> LENGTH: 14
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Nme-Ala
```

```
<400> SEQUENCE: 345

Lys Met Pro Ser Phe Ile Ile Val Leu Thr Val Ile Ala Gly
1               5                   10

<210> SEQ ID NO 346
<211> LENGTH: 13
<212> TYPE: PRT
<213> ORGANISM: Homo sapiens

<400> SEQUENCE: 346

Lys Met Pro Ser Ser Ile Ile Val Leu Thr Val Ile Gly
1               5                   10

<210> SEQ ID NO 347
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 347

Lys Met Trp Leu Ala Thr Ser Ile Pro Thr Ala Ala Gly
1               5                   10

<210> SEQ ID NO 348
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 348

Lys Met Trp Leu Ala Thr Ser Ile Pro Thr Ala Ser Gly
1               5                   10

<210> SEQ ID NO 349
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 349

Lys Met Trp Leu Ala Thr Ser Ile Pro Ala Ala Ala Gly
1               5                   10

<210> SEQ ID NO 350
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 350

Lys Met Trp Leu Ala Thr Cys Ile Pro Thr Ala Ala Gly
1               5                   10

<210> SEQ ID NO 351
<211> LENGTH: 13
```

```
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 351

Lys Met Trp Leu Ala Thr Ser Ile Pro Thr Thr Ala Gly
1               5                   10

<210> SEQ ID NO 352
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 352

Lys Met Trp Leu Ala Thr Gly Ile Pro Thr Ala Ala Gly
1               5                   10

<210> SEQ ID NO 353
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 353

Lys Met Arg Leu Ala Thr Ser Ile Pro Thr Ala Ala Gly
1               5                   10

<210> SEQ ID NO 354
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 354

Lys Met Pro Leu Ala Ile Ser Arg Phe Glu His Ile Gly
1               5                   10

<210> SEQ ID NO 355
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 355

Lys Met Pro Leu Ala Ile Ser Arg Phe Glu His Leu Gly
1               5                   10

<210> SEQ ID NO 356
<211> LENGTH: 13
<212> TYPE: PRT
<213> ORGANISM: Homo sapiens
<220> FEATURE:
<221> NAME/KEY: MOD_RES
```

```
<222> LOCATION: (5)..(5)
<223> OTHER INFORMATION: Nme-Ala

<400> SEQUENCE: 356

Lys Met Pro Leu Ala Ile Ser Lys Phe Glu His Ile Gly
1               5                   10

<210> SEQ ID NO 357
<211> LENGTH: 14
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 357

Lys Met Pro Leu Ala Ile Ser Arg Phe Glu His Ile Glu Gly
1               5                   10

<210> SEQ ID NO 358
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 358

Lys Met Pro Leu Ala Ile Ser Arg Phe Glu His Phe Gly
1               5                   10

<210> SEQ ID NO 359
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 359

Lys Met Pro Leu Ala Ile Ser Arg Ile Glu His Ile Gly
1               5                   10

<210> SEQ ID NO 360
<211> LENGTH: 14
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 360

Lys Met Pro Leu Ala Ile Ser Arg Phe Glu His Ile Arg Gly
1               5                   10

<210> SEQ ID NO 361
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 361
```

Lys Met Pro Leu Ala Ile Arg Arg Phe Glu His Ile Gly
1               5                   10

<210> SEQ ID NO 362
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 362

Lys Met Pro Leu Ala Asn Ser Arg Phe Glu His Ile Gly
1               5                   10

<210> SEQ ID NO 363
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 363

Lys Met Pro Leu Ala Ile Ser Arg Phe Glu His Val Gly
1               5                   10

<210> SEQ ID NO 364
<211> LENGTH: 13
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Nme-Ala

<400> SEQUENCE: 364

Lys Met Pro Leu Ala Ile Gly Arg Phe Glu His Ile Gly
1               5                   10

<210> SEQ ID NO 365
<211> LENGTH: 13
<212> TYPE: PRT
<213> ORGANISM: Homo sapiens

<400> SEQUENCE: 365

Lys Met Pro Leu Gln Ile Ser Arg Phe Glu His Ile Gly
1               5                   10

<210> SEQ ID NO 366
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Nme-Ala

<400> SEQUENCE: 366

Lys Met Trp Ala Trp Leu Ser Arg Gln Trp Ile Val Gly
1               5                   10

<210> SEQ ID NO 367
<211> LENGTH: 16
<212> TYPE: PRT

<213> ORGANISM: Homo sapiens

<400> SEQUENCE: 367

Lys Met Tyr Glu Ser Ile Leu Asp Glu His Met Gln Arg Val Trp Gly
1               5                   10                  15

<210> SEQ ID NO 368
<211> LENGTH: 16
<212> TYPE: PRT
<213> ORGANISM: Homo sapiens

<400> SEQUENCE: 368

Lys Met Pro Glu Ser Ile Leu Asp Glu His Val Gln Arg Val Trp Gly
1               5                   10                  15

<210> SEQ ID NO 369
<211> LENGTH: 16
<212> TYPE: PRT
<213> ORGANISM: Homo sapiens

<400> SEQUENCE: 369

Lys Met Trp Glu Ser Ile Leu Asp Glu His Met Gln Arg Val Trp Gly
1               5                   10                  15

<210> SEQ ID NO 370
<211> LENGTH: 19
<212> TYPE: PRT
<213> ORGANISM: Homo sapiens

<400> SEQUENCE: 370

Lys Met Tyr Glu Ser Ile Leu Asp Glu His Val Gln Arg Val Trp Gly
1               5                   10                  15

Ile Leu Arg

<210> SEQ ID NO 371
<211> LENGTH: 16
<212> TYPE: PRT
<213> ORGANISM: Homo sapiens

<400> SEQUENCE: 371

Lys Met Trp Glu Ser Ile Leu Asp Glu His Val Gln Arg Val Trp Gly
1               5                   10                  15

<210> SEQ ID NO 372
<211> LENGTH: 19
<212> TYPE: PRT
<213> ORGANISM: Homo sapiens

<400> SEQUENCE: 372

Lys Met Trp Glu Ser Ile Leu Asp Glu His Val Gln Arg Val Trp Gly
1               5                   10                  15

Ile Leu Arg

<210> SEQ ID NO 373
<211> LENGTH: 17
<212> TYPE: PRT
<213> ORGANISM: Homo sapiens

<400> SEQUENCE: 373

Lys Met Trp Glu Ser Ile Leu Asp Glu His Met Gln Arg Val Trp Arg
1               5                   10                  15

Gly

```
<210> SEQ ID NO 374
<211> LENGTH: 16
<212> TYPE: PRT
<213> ORGANISM: Homo sapiens

<400> SEQUENCE: 374

Lys Met Tyr Glu Ser Ile Leu Asp Glu His Val Gln Arg Val Trp Gly
1               5                   10                  15

<210> SEQ ID NO 375
<211> LENGTH: 16
<212> TYPE: PRT
<213> ORGANISM: Homo sapiens

<400> SEQUENCE: 375

Lys Met Trp Glu Ser Ile Leu Asp Glu His Val Lys Arg Val Trp Gly
1               5                   10                  15

<210> SEQ ID NO 376
<211> LENGTH: 16
<212> TYPE: PRT
<213> ORGANISM: Homo sapiens

<400> SEQUENCE: 376

Lys Met Trp Glu Ser Ile Leu Asp Glu His Val Gln Arg Val Trp Gly
1               5                   10                  15

<210> SEQ ID NO 377
<211> LENGTH: 14
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: aMe-Ser
<220> FEATURE:
<221> NAME/KEY: MOD_RES
<222> LOCATION: (9)..(9)
<223> OTHER INFORMATION: aMe-Val
<220> FEATURE:
<221> NAME/KEY: MOD_RES
<222> LOCATION: (14)..(14)
<223> OTHER INFORMATION: Pra

<400> SEQUENCE: 377

Trp Glu Ser Ile Leu Asp Glu His Val Gln Arg Val Trp Xaa
1               5                   10

<210> SEQ ID NO 378
<211> LENGTH: 14
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: NmeNva

<400> SEQUENCE: 378

Met Leu Val Ile Asp Gln Val Ser Val Ser Arg Val Trp Lys
1               5                   10

<210> SEQ ID NO 379
<211> LENGTH: 15
<212> TYPE: PRT
<213> ORGANISM: Homo sapiens
<220> FEATURE:
<221> NAME/KEY: MOD_RES
<222> LOCATION: (2)..(2)
```

```
<223> OTHER INFORMATION: NmeNva

<400> SEQUENCE: 379

Met Val Arg Ser Ser Gln Glu Leu Pro Val His Arg Val Trp Lys
1               5                   10                  15

<210> SEQ ID NO 380
<211> LENGTH: 12
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: NmeNva

<400> SEQUENCE: 380

Gly Lys Trp Leu Val Thr Ser Ile Pro Thr Ala Ala
1               5                   10

<210> SEQ ID NO 381
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: NmeNva

<400> SEQUENCE: 381

Lys Trp Leu Val Thr Ser Ile Pro Thr Ala Ala
1               5                   10

<210> SEQ ID NO 382
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: NmeNva

<400> SEQUENCE: 382

Met Trp Leu Val Thr Ser Ile Pro Thr Ala Ala Lys
1               5                   10

<210> SEQ ID NO 383
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: NmeNva

<400> SEQUENCE: 383

Met Pro Leu Val Ile Ser Arg Phe Glu His Ile Lys
1               5                   10

<210> SEQ ID NO 384
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: NmeNva

<400> SEQUENCE: 384
```

```
Met Pro Leu Val Ile Ser Arg Phe Glu His Ile Lys
1               5                   10
```

<210> SEQ ID NO 385
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: NmeNva

<400> SEQUENCE: 385

```
Met Pro Leu Val Ile Ser Arg Phe Glu His Ile Lys
1               5                   10
```

<210> SEQ ID NO 386
<211> LENGTH: 11
<212> TYPE: PRT
<213> ORGANISM: Homo sapiens

<400> SEQUENCE: 386

```
Lys Pro Pro Trp Val Ser Pro Pro Met Thr Met
1               5                   10
```

<210> SEQ ID NO 387
<211> LENGTH: 12
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: NmeNva
<220> FEATURE:
<221> NAME/KEY: MOD_RES
<222> LOCATION: (8)..(8)
<223> OTHER INFORMATION: NmeNva
<220> FEATURE:
<221> NAME/KEY: MOD_RES
<222> LOCATION: (11)..(11)
<223> OTHER INFORMATION: NmeNva

<400> SEQUENCE: 387

```
Met Met Val Gln Ser Leu Phe Val Pro Pro Val Lys
1               5                   10
```

<210> SEQ ID NO 388
<211> LENGTH: 13
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: NmeNva

<400> SEQUENCE: 388

```
Met Trp Val Trp Leu Ser Arg Gln Trp Ile Val Leu Lys
1               5                   10
```

<210> SEQ ID NO 389
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Lys(Aoc); wherein the Lys is modified on the
      side chain

<400> SEQUENCE: 389

```
Lys Met Ile Arg Met Trp Phe Leu Ile Ser Phe Trp Gly
1               5                   10

<210> SEQ ID NO 390
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Trp
<220> FEATURE:
<221> NAME/KEY: MOD_RES
<222> LOCATION: (4)..(4)
<223> OTHER INFORMATION: aMe-Ser
<220> FEATURE:
<221> NAME/KEY: MOD_RES
<222> LOCATION: (10)..(10)
<223> OTHER INFORMATION: aMe-Val

<400> SEQUENCE: 390

Trp Trp Glu Ser Ile Leu Asp Glu His Val Gln Arg Val Trp Gly
1               5                   10                  15

<210> SEQ ID NO 391
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: beta-Ala
<220> FEATURE:
<221> NAME/KEY: MOD_RES
<222> LOCATION: (3)..(3)
<223> OTHER INFORMATION: NMe-Trp
<220> FEATURE:
<221> NAME/KEY: MOD_RES
<222> LOCATION: (5)..(5)
<223> OTHER INFORMATION: aMe-Ser
<220> FEATURE:
<221> NAME/KEY: MOD_RES
<222> LOCATION: (11)..(11)
<223> OTHER INFORMATION: aMe-Val

<400> SEQUENCE: 391

Ala Trp Trp Glu Ser Ile Leu Asp Glu His Val Gln Arg Val Trp Gly
1               5                   10                  15

<210> SEQ ID NO 392
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Trp
<220> FEATURE:
<221> NAME/KEY: MOD_RES
<222> LOCATION: (4)..(4)
<223> OTHER INFORMATION: aMe-Ser
<220> FEATURE:
<221> NAME/KEY: MOD_RES
<222> LOCATION: (10)..(10)
<223> OTHER INFORMATION: aMe-Val

<400> SEQUENCE: 392

Trp Trp Glu Ser Ile Leu Asp Glu His Val Gln Arg Val Trp Gly
1               5                   10                  15

<210> SEQ ID NO 393
```

```
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Trp
<220> FEATURE:
<221> NAME/KEY: MOD_RES
<222> LOCATION: (4)..(4)
<223> OTHER INFORMATION: aMe-Ser
<220> FEATURE:
<221> NAME/KEY: MOD_RES
<222> LOCATION: (10)..(10)
<223> OTHER INFORMATION: aMe-Val

<400> SEQUENCE: 393

Trp Trp Glu Ser Ile Leu Asp Glu His Val Gln Arg Val Trp
1               5                   10

<210> SEQ ID NO 394
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: beta-Ala
<220> FEATURE:
<221> NAME/KEY: MOD_RES
<222> LOCATION: (3)..(3)
<223> OTHER INFORMATION: NMe-Trp
<220> FEATURE:
<221> NAME/KEY: MOD_RES
<222> LOCATION: (5)..(5)
<223> OTHER INFORMATION: aMe-Ser
<220> FEATURE:
<221> NAME/KEY: MOD_RES
<222> LOCATION: (11)..(11)
<223> OTHER INFORMATION: aMe-Val

<400> SEQUENCE: 394

Ala Trp Trp Glu Ser Ile Leu Asp Glu His Val Gln Arg Val Trp
1               5                   10                  15

<210> SEQ ID NO 395
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Trp
<220> FEATURE:
<221> NAME/KEY: MOD_RES
<222> LOCATION: (4)..(4)
<223> OTHER INFORMATION: aMe-Ser
<220> FEATURE:
<221> NAME/KEY: MOD_RES
<222> LOCATION: (10)..(10)
<223> OTHER INFORMATION: aMe-Val

<400> SEQUENCE: 395

Trp Trp Glu Ser Ile Leu Asp Glu His Val Gln Arg Val Trp
1               5                   10

<210> SEQ ID NO 396
<211> LENGTH: 15
<212> TYPE: PRT
<213> ORGANISM: Homo sapiens
<220> FEATURE:
<221> NAME/KEY: MOD_RES
<222> LOCATION: (2)..(2)
```

```
<223> OTHER INFORMATION: NMe-Trp
<220> FEATURE:
<221> NAME/KEY: MOD_RES
<222> LOCATION: (4)..(4)
<223> OTHER INFORMATION: aMe-Ser
<220> FEATURE:
<221> NAME/KEY: MOD_RES
<222> LOCATION: (10)..(10)
<223> OTHER INFORMATION: aMe-Val

<400> SEQUENCE: 396

Trp Trp Glu Ser Ile Leu Asp Glu His Val Gln Arg Val Trp Gly
1               5                   10                  15

<210> SEQ ID NO 397
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Trp
<220> FEATURE:
<221> NAME/KEY: MOD_RES
<222> LOCATION: (4)..(4)
<223> OTHER INFORMATION: aMe-Ser
<220> FEATURE:
<221> NAME/KEY: MOD_RES
<222> LOCATION: (10)..(10)
<223> OTHER INFORMATION: aMe-Val

<400> SEQUENCE: 397

Trp Trp Glu Ser Ile Leu Asp Glu His Val Gln Arg Val Trp
1               5                   10

<210> SEQ ID NO 398
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: NMe-Trp
<220> FEATURE:
<221> NAME/KEY: MOD_RES
<222> LOCATION: (5)..(5)
<223> OTHER INFORMATION: aMe-Ser
<220> FEATURE:
<221> NAME/KEY: MOD_RES
<222> LOCATION: (11)..(11)
<223> OTHER INFORMATION: aMe-Val

<400> SEQUENCE: 398

Gly Trp Trp Glu Ser Ile Leu Asp Glu His Val Gln Arg Val Trp
1               5                   10                  15

<210> SEQ ID NO 399
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: beta-Ala
<220> FEATURE:
<221> NAME/KEY: MOD_RES
<222> LOCATION: (3)..(3)
<223> OTHER INFORMATION: NMe-Trp
<220> FEATURE:
<221> NAME/KEY: MOD_RES
<222> LOCATION: (5)..(5)
<223> OTHER INFORMATION: aMe-Ser
<220> FEATURE:
```

```
<221> NAME/KEY: MOD_RES
<222> LOCATION: (11)..(11)
<223> OTHER INFORMATION: aMe-Val

<400> SEQUENCE: 399

Ala Trp Trp Glu Ser Ile Leu Asp Glu His Val Gln Arg Val Trp
1               5                   10                  15

<210> SEQ ID NO 400
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Trp
<220> FEATURE:
<221> NAME/KEY: MOD_RES
<222> LOCATION: (4)..(4)
<223> OTHER INFORMATION: aMe-Ser
<220> FEATURE:
<221> NAME/KEY: MOD_RES
<222> LOCATION: (10)..(10)
<223> OTHER INFORMATION: aMe-Val

<400> SEQUENCE: 400

Trp Trp Glu Ser Ile Leu Asp Glu His Val Gln Arg Val Trp
1               5                   10

<210> SEQ ID NO 401
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala

<400> SEQUENCE: 401

Trp Ala Gln Lys Ile Leu Asp Glu His Val Gln Arg Val Trp Gly
1               5                   10                  15

<210> SEQ ID NO 402
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala

<400> SEQUENCE: 402

Trp Ala Gln Lys Ile Leu Asp Glu His Val Gln Arg Val Trp Gly
1               5                   10                  15

<210> SEQ ID NO 403
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala
<220> FEATURE:
<221> NAME/KEY: MOD_RES
<222> LOCATION: (10)..(10)
<223> OTHER INFORMATION: Chg

<400> SEQUENCE: 403

Trp Ala Gln Lys Ile Leu Asp Glu His Gly Gln Arg Val Trp Gly
```

-continued

```
1               5                   10                  15

<210> SEQ ID NO 404
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala
<220> FEATURE:
<221> NAME/KEY: MOD_RES
<222> LOCATION: (10)..(10)
<223> OTHER INFORMATION: Chg

<400> SEQUENCE: 404

Trp Ala Gln Lys Ile Leu Asp Glu His Gly Gln Arg Val Trp Gly
1               5                   10                  15

<210> SEQ ID NO 405
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala
<220> FEATURE:
<221> NAME/KEY: MOD_RES
<222> LOCATION: (10)..(10)
<223> OTHER INFORMATION: Chg

<400> SEQUENCE: 405

Trp Ala Gln Lys Ile Leu Asp Glu His Gly Gln Arg Val Trp Gly
1               5                   10                  15

<210> SEQ ID NO 406
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala
<220> FEATURE:
<221> NAME/KEY: MOD_RES
<222> LOCATION: (6)..(6)
<223> OTHER INFORMATION: Cha

<400> SEQUENCE: 406

Trp Ala Gln Lys Ile Ala Asp Glu His Val Gln Arg Val Trp Gly
1               5                   10                  15

<210> SEQ ID NO 407
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala
<220> FEATURE:
<221> NAME/KEY: MOD_RES
<222> LOCATION: (6)..(6)
<223> OTHER INFORMATION: Cha

<400> SEQUENCE: 407

Trp Ala Gln Lys Ile Ala Asp Glu His Val Gln Arg Val Trp Gly
1               5                   10                  15
```

```
<210> SEQ ID NO 408
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala
<220> FEATURE:
<221> NAME/KEY: MOD_RES
<222> LOCATION: (6)..(6)
<223> OTHER INFORMATION: Cha

<400> SEQUENCE: 408

Trp Ala Gln Lys Ile Ala Asp Glu His Val Gln Arg Val Trp Gly
1               5                   10                  15

<210> SEQ ID NO 409
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala
<220> FEATURE:
<221> NAME/KEY: MOD_RES
<222> LOCATION: (6)..(6)
<223> OTHER INFORMATION: Cha

<400> SEQUENCE: 409

Trp Ala Gln Lys Ile Ala Asp Glu His Val Gln Arg Val Trp Gly
1               5                   10                  15

<210> SEQ ID NO 410
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Beta-Ala

<400> SEQUENCE: 410

Ala Arg Leu Pro Glu Ser Ile Leu Asp Glu His Val Gln Arg Val Trp
1               5                   10                  15
Pro

<210> SEQ ID NO 411
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Beta-Ala

<400> SEQUENCE: 411

Ala Arg Leu Pro Glu Ser Ile Leu Asp Glu His Trp Gln Arg Val Trp
1               5                   10                  15
Pro

<210> SEQ ID NO 412
<211> LENGTH: 18
<212> TYPE: PRT
<213> ORGANISM: Homo sapiens
<220> FEATURE:
<221> NAME/KEY: MOD_RES
<222> LOCATION: (1)..(1)
```

```
<223> OTHER INFORMATION: Beta-Ala

<400> SEQUENCE: 412

Ala Glu Glu Asp Pro Gln Thr Ile Leu Asp Asp His Leu Ser Arg Val
1               5                   10                  15

Leu Lys

<210> SEQ ID NO 413
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Beta-Ala

<400> SEQUENCE: 413

Ala Arg Leu Pro Glu Ser Ile Leu Asp Glu His Val Gln Arg Val Trp
1               5                   10                  15

Pro

<210> SEQ ID NO 414
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg
<220> FEATURE:
<221> NAME/KEY: MOD_RES
<222> LOCATION: (11)..(11)
<223> OTHER INFORMATION: Aib

<400> SEQUENCE: 414

Trp Ala Gln Lys Ile Leu Asp Glu His Gly Xaa Arg Val Trp Gly
1               5                   10                  15

<210> SEQ ID NO 415
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 415

Trp Ala Gln Lys Ile Leu Asp Glu His Gly Ser Arg Val Trp Gly
1               5                   10                  15

<210> SEQ ID NO 416
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
```

<222> LOCATION: (10)..(10)
<223> OTHER INFORMATION: Chg

<400> SEQUENCE: 416

Trp Ala Gln Lys Ile Leu Asp Glu His Gly Ser Arg Val Trp Gly
1               5                   10                  15

<210> SEQ ID NO 417
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (10)..(10)
<223> OTHER INFORMATION: Chg

<400> SEQUENCE: 417

Trp Ala Xaa Lys Ile Leu Asp Glu His Gly Gln Arg Val Trp Gly
1               5                   10                  15

<210> SEQ ID NO 418
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (10)..(10)
<223> OTHER INFORMATION: Chg

<400> SEQUENCE: 418

Trp Ala Xaa Lys Ile Leu Asp Glu His Gly Gln Arg Val Trp Gly
1               5                   10                  15

<210> SEQ ID NO 419
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (3)..(3)
<223> OTHER INFORMATION: NMe-Ala
<220> FEATURE:
<221> NAME/KEY: MOD_RES
<222> LOCATION: (11)..(11)
<223> OTHER INFORMATION: Chg

<400> SEQUENCE: 419

Ala Trp Ala Gln Lys Ile Leu Asp Glu His Gly Gln Arg Val Trp Gly
1               5                   10                  15

<210> SEQ ID NO 420

```
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (5)..(5)
<223> OTHER INFORMATION: Chg

<400> SEQUENCE: 420

Trp Ala Gln Lys Gly Leu Asp Glu His Val Gln Arg Val Trp Gly
1               5                   10                  15

<210> SEQ ID NO 421
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (5)..(5)
<223> OTHER INFORMATION: Chg

<400> SEQUENCE: 421

Trp Ala Gln Lys Gly Leu Asp Glu His Val Gln Arg Val Trp Gly
1               5                   10                  15

<210> SEQ ID NO 422
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (5)..(5)
<223> OTHER INFORMATION: Chg

<400> SEQUENCE: 422

Trp Ala Gln Lys Gly Leu Asp Glu His Val Gln Arg Val Trp Gly
1               5                   10                  15

<210> SEQ ID NO 423
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (4)..(4)
<223> OTHER INFORMATION: Orn
<220> FEATURE:
<221> NAME/KEY: MOD_RES
<222> LOCATION: (10)..(10)
<223> OTHER INFORMATION: Chg

<400> SEQUENCE: 423

Trp Ala Gln Xaa Ile Leu Asp Glu His Gly Gln Arg Val Trp Gly
1               5                   10                  15
```

-continued

```
<210> SEQ ID NO 424
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (4)..(4)
<223> OTHER INFORMATION: Orn
<220> FEATURE:
<221> NAME/KEY: MOD_RES
<222> LOCATION: (10)..(10)
<223> OTHER INFORMATION: Chg

<400> SEQUENCE: 424

Trp Ala Gln Xaa Ile Leu Asp Glu His Gly Gln Arg Val Trp Gly
1               5                   10                  15

<210> SEQ ID NO 425
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (4)..(4)
<223> OTHER INFORMATION: Orn
<220> FEATURE:
<221> NAME/KEY: MOD_RES
<222> LOCATION: (10)..(10)
<223> OTHER INFORMATION: Chg

<400> SEQUENCE: 425

Trp Ala Gln Xaa Ile Leu Asp Glu His Gly Gln Arg Val Trp Gly
1               5                   10                  15

<210> SEQ ID NO 426
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 426

Trp Ala Gln Glu Ile Leu Asp Lys His Gly Gln Arg Val Trp Gly
1               5                   10                  15

<210> SEQ ID NO 427
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 427
```

```
Trp Ala Gln Glu Ile Leu Asp Lys His Gly Gln Arg Val Trp Gly
1               5                   10                  15

<210> SEQ ID NO 428
<211> LENGTH: 16
<212> TYPE: PRT
<213> ORGANISM: Homo sapiens

<400> SEQUENCE: 428

Arg Trp Pro Gln Lys Ile Leu Asp Glu His Val Arg Arg Val Trp Arg
1               5                   10                  15

<210> SEQ ID NO 429
<211> LENGTH: 17
<212> TYPE: PRT
<213> ORGANISM: Homo sapiens

<400> SEQUENCE: 429

Arg Arg Trp Pro Gln Lys Ile Leu Asp Glu His Val Arg Arg Val Trp
1               5                   10                  15

Arg

<210> SEQ ID NO 430
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 430

Trp Ala Gln Lys Ile Leu Asp Asp His Gly Gln Arg Val Trp Gly
1               5                   10                  15

<210> SEQ ID NO 431
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 431

Trp Ala Gln Lys Ile Leu Asp Asp His Gly Gln Arg Val Trp Gly
1               5                   10                  15

<210> SEQ ID NO 432
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg
```

```
<400> SEQUENCE: 432

Trp Ala Gln Lys Ile Leu Asp Asp His Gly Gln Arg Val Trp Gly
1               5                   10                  15

<210> SEQ ID NO 433
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: NMe-Ala
<220> FEATURE:
<221> NAME/KEY: MOD_RES
<222> LOCATION: (9)..(9)
<223> OTHER INFORMATION: Chg

<400> SEQUENCE: 433

Ala Gln Lys Ile Leu Asn Glu His Gly Gln Arg Val Trp Gly
1               5                   10

<210> SEQ ID NO 434
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: NMe-Ala
<220> FEATURE:
<221> NAME/KEY: MOD_RES
<222> LOCATION: (9)..(9)
<223> OTHER INFORMATION: Chg

<400> SEQUENCE: 434

Ala Gln Lys Ile Leu Asn Glu His Gly Gln Arg Val Trp Gly
1               5                   10

<210> SEQ ID NO 435
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 435

Trp Ala Gln Lys Ile Leu Asn Glu His Gly Gln Arg Val Trp Gly
1               5                   10                  15

<210> SEQ ID NO 436
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 436
```

```
Trp Ala Gln Lys Ile Leu Asn Glu His Gly Gln Arg Val Trp Gly
1               5                   10                  15

<210> SEQ ID NO 437
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala

<400> SEQUENCE: 437

Trp Ala Gln Ser Ile Leu Asp Glu His Val Gln Lys Val Trp Gly
1               5                   10                  15

<210> SEQ ID NO 438
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala

<400> SEQUENCE: 438

Trp Ala Gln Ser Ile Leu Asp Glu His Val Gln Lys Val Trp Gly
1               5                   10                  15

<210> SEQ ID NO 439
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala

<400> SEQUENCE: 439

Trp Ala Gln Ser Ile Leu Asp Glu His Val Gln Lys Val Trp Gly
1               5                   10                  15

<210> SEQ ID NO 440
<211> LENGTH: 13
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Chg

<400> SEQUENCE: 440

Gln Lys Ile Leu Asp Glu His Gly Gln Arg Val Trp Gly
1               5                   10

<210> SEQ ID NO 441
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Chg

<400> SEQUENCE: 441

Trp Ala Gln Lys Ile Leu Asp Glu His Gly Gln Arg Val Trp Gly
1               5                   10                  15
```

```
<210> SEQ ID NO 442
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Pip
<220> FEATURE:
<221> NAME/KEY: MOD_RES
<222> LOCATION: (10)..(10)
<223> OTHER INFORMATION: Chg

<400> SEQUENCE: 442

Trp Xaa Gln Lys Ile Leu Asp Glu His Gly Gln Arg Val Trp Gly
1               5                   10                  15

<210> SEQ ID NO 443
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (10)..(10)
<223> OTHER INFORMATION: Chg

<400> SEQUENCE: 443

Trp Xaa Gln Lys Ile Leu Asp Glu His Gly Gln Arg Val Trp Gly
1               5                   10                  15

<210> SEQ ID NO 444
<211> LENGTH: 16
<212> TYPE: PRT
<213> ORGANISM: Homo sapiens

<400> SEQUENCE: 444

Glu Asp Pro Gln Lys Ile Leu Asp Glu His Leu Gln Arg Val Leu Lys
1               5                   10                  15

<210> SEQ ID NO 445
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: NMe-Ala
<220> FEATURE:
<221> NAME/KEY: MOD_RES
<222> LOCATION: (9)..(9)
<223> OTHER INFORMATION: Chg

<400> SEQUENCE: 445

Ala Gln Lys Ile Leu Asp Glu His Gly Gln Arg Val Trp
1               5                   10

<210> SEQ ID NO 446
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
```

```
<223> OTHER INFORMATION: Chg

<400> SEQUENCE: 446

Trp Ala Gln Lys Ile Leu Asp Glu His Gly Gln Arg Val Trp
1               5                   10

<210> SEQ ID NO 447
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 447

Trp Ala Gln Lys Ile Leu Asp Glu His Gly Gln Arg Val Trp
1               5                   10

<210> SEQ ID NO 448
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: NMe-Ala
<220> FEATURE:
<221> NAME/KEY: MOD_RES
<222> LOCATION: (9)..(9)
<223> OTHER INFORMATION: Chg

<400> SEQUENCE: 448

Ala Gln Lys Ile Leu Asp Glu His Gly Gln Arg Val Trp Arg
1               5                   10

<210> SEQ ID NO 449
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 449

Trp Ala Gln Lys Ile Leu Asp Glu His Gly Gln Arg Val Trp Arg
1               5                   10                  15

<210> SEQ ID NO 450
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala

<400> SEQUENCE: 450

Trp Ala Glu Ser Ile Leu Lys Glu His Val Gln Arg Val Trp Gly
1               5                   10                  15
```

```
<210> SEQ ID NO 451
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala

<400> SEQUENCE: 451

Trp Ala Glu Ser Ile Leu Lys Glu His Val Gln Arg Val Trp Gly
1               5                   10                  15

<210> SEQ ID NO 452
<211> LENGTH: 13
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 452

Trp Ala Gln Lys Ile Leu Asn Asp His Gly Gln Ala Val
1               5                   10

<210> SEQ ID NO 453
<211> LENGTH: 13
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 453

Trp Ala Gln Lys Ile Leu Asn Asp His Gly Gln Ala Val
1               5                   10

<210> SEQ ID NO 454
<211> LENGTH: 13
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 454

Trp Ala Gln Lys Ile Leu Asn Asp His Gly Gln Ala Val
1               5                   10

<210> SEQ ID NO 455
<211> LENGTH: 14
<212> TYPE: PRT
<213> ORGANISM: Homo sapiens
<220> FEATURE:
<221> NAME/KEY: MOD_RES
```

<222> LOCATION: (2)..(2)
<223> OTHER INFORMATION: Aib
<220> FEATURE:
<221> NAME/KEY: MOD_RES
<222> LOCATION: (10)..(10)
<223> OTHER INFORMATION: Chg

<400> SEQUENCE: 455

Trp Xaa Gln Lys Ile Leu Asn Asp His Gly Gln Arg Val Trp
1               5                   10

<210> SEQ ID NO 456
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (10)..(10)
<223> OTHER INFORMATION: Chg

<400> SEQUENCE: 456

Trp Xaa Gln Lys Ile Leu Asn Asp His Gly Gln Arg Val Trp
1               5                   10

<210> SEQ ID NO 457
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: NMe-Ala
<220> FEATURE:
<221> NAME/KEY: MOD_RES
<222> LOCATION: (9)..(9)
<223> OTHER INFORMATION: Chg

<400> SEQUENCE: 457

Ala Gln Lys Ile Leu Asp Asp His Gly Gln Arg Val Trp Gly
1               5                   10

<210> SEQ ID NO 458
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 458

Trp Ala Gln Lys Ile Leu Asn Asp His Gly Gln Ala Val Trp
1               5                   10

<210> SEQ ID NO 459
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:

```
<221> NAME/KEY: MOD_RES
<222> LOCATION: (10)..(10)
<223> OTHER INFORMATION: Chg

<400> SEQUENCE: 459

Trp Ala Gln Lys Ile Leu Asn Asp His Gly Gln Ala Val Trp
1               5                   10

<210> SEQ ID NO 460
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 460

Trp Ala Gln Ser Ile Leu Asp Lys His Gly Gln Asp Val Trp
1               5                   10

<210> SEQ ID NO 461
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 461

Trp Ala Gln Ser Ile Leu Asp Lys His Gly Gln Asp Val Trp
1               5                   10

<210> SEQ ID NO 462
<211> LENGTH: 14
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Chg

<400> SEQUENCE: 462

Trp Pro Gln Ser Ile Leu Asp Lys His Gly Gln Asp Val Trp
1               5                   10

<210> SEQ ID NO 463
<211> LENGTH: 14
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Chg

<400> SEQUENCE: 463

Trp Pro Gln Ser Ile Leu Asp Lys His Gly Gln Asp Val Trp
1               5                   10

<210> SEQ ID NO 464
```

```
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 464

Trp Ala Gln Lys Ile Leu Asp Glu His Gly Glu Asp Val Trp Lys
1               5                   10                  15

<210> SEQ ID NO 465
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 465

Trp Ala Gln Lys Ile Leu Asp Glu His Gly Glu Asp Val Trp Lys
1               5                   10                  15

<210> SEQ ID NO 466
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 466

Trp Ala Gln Ser Ile Leu Asp Glu His Gly Gln Lys Val Trp
1               5                   10

<210> SEQ ID NO 467
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 467

Trp Ala Gln Ser Ile Leu Asp Glu His Gly Gln Lys Val Trp
1               5                   10

<210> SEQ ID NO 468
<211> LENGTH: 14
<212> TYPE: PRT
<213> ORGANISM: Homo sapiens
```

```
-continued

<220> FEATURE:
<221> NAME/KEY: MOD_RES
<222> LOCATION: (10)..(10)
<223> OTHER INFORMATION: Chg

<400> SEQUENCE: 468

Trp Pro Gln Ser Ile Leu Asp Glu His Gly Gln Lys Val Trp
1               5                   10

<210> SEQ ID NO 469
<211> LENGTH: 14
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Chg

<400> SEQUENCE: 469

Trp Pro Gln Ser Ile Leu Asp Glu His Gly Gln Lys Val Trp
1               5                   10

<210> SEQ ID NO 470
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 470

Trp Ala Gln Ser Ile Leu Asp Glu His Gly Gln Lys Val Trp Gly
1               5                   10                  15

<210> SEQ ID NO 471
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 471

Trp Ala Gln Ser Ile Leu Asp Glu His Gly Gln Lys Val Trp Gly
1               5                   10                  15

<210> SEQ ID NO 472
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Chg

<400> SEQUENCE: 472

Trp Pro Gln Ser Ile Leu Asp Glu His Gly Gln Lys Val Trp Gly
1               5                   10                  15
```

```
<210> SEQ ID NO 473
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Chg

<400> SEQUENCE: 473

Trp Pro Gln Ser Ile Leu Asp Glu His Gly Gln Lys Val Trp Gly
1               5                   10                  15

<210> SEQ ID NO 474
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: NMe-Trp
<220> FEATURE:
<221> NAME/KEY: MOD_RES
<222> LOCATION: (5)..(5)
<223> OTHER INFORMATION: aMe-Ser
<220> FEATURE:
<221> NAME/KEY: MOD_RES
<222> LOCATION: (11)..(11)
<223> OTHER INFORMATION: aMe-Val

<400> SEQUENCE: 474

Gly Trp Trp Glu Ser Ile Leu Asp Glu His Val Gln Arg Val Trp
1               5                   10                  15

<210> SEQ ID NO 475
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Beta-Ala

<400> SEQUENCE: 475

Ala Glu Asn Pro Glu Ser Ile Leu Asp Glu His Val Gln Arg Val Met
1               5                   10                  15

Arg

<210> SEQ ID NO 476
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 476

Trp Ala Gln Lys Ile Leu Asp Glu His Gly Glu Ala Val Trp Lys
1               5                   10                  15

<210> SEQ ID NO 477
<211> LENGTH: 15
<212> TYPE: PRT
<213> ORGANISM: Homo sapiens
<220> FEATURE:
```

```
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 477

Trp Ala Gln Lys Ile Leu Asp Glu His Gly Glu Ala Val Trp Lys
1               5                   10                  15

<210> SEQ ID NO 478
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 478

Trp Ala Gln Lys Ile Leu Asp Glu His Gly Gln Arg Val Trp Arg
1               5                   10                  15

<210> SEQ ID NO 479
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: NMe-Ala
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (9)..(9)
<223> OTHER INFORMATION: Chg

<400> SEQUENCE: 479

Ala Xaa Lys Ile Leu Asp Asp His Gly Gln Arg Val Trp
1               5                   10

<210> SEQ ID NO 480
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: NMe-Ala
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (9)..(9)
<223> OTHER INFORMATION: Chg

<400> SEQUENCE: 480

Ala Xaa Lys Ile Leu Asp Asp His Gly Gln Arg Val Trp
1               5                   10
```

```
<210> SEQ ID NO 481
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (10)..(10)
<223> OTHER INFORMATION: Chg

<400> SEQUENCE: 481

Trp Ala Xaa Lys Ile Leu Asp Asp His Gly Gln Arg Val Trp
1               5                   10

<210> SEQ ID NO 482
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: NMe-Ala
<220> FEATURE:
<221> NAME/KEY: MOD_RES
<222> LOCATION: (9)..(9)
<223> OTHER INFORMATION: Chg

<400> SEQUENCE: 482

Ala Gln Asp Ile Leu Asp Lys His Gly Gln Arg Val Trp Gly
1               5                   10

<210> SEQ ID NO 483
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Nme-Ala
<220> FEATURE:
<221> NAME/KEY: MOD_RES
<222> LOCATION: (10)..(10)
<223> OTHER INFORMATION: Chg

<400> SEQUENCE: 483

Trp Ala Gln Asp Ile Leu Asp Lys His Gly Gln Arg Val Trp Gly
1               5                   10                  15

<210> SEQ ID NO 484
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: NMe-Ala
<220> FEATURE:
<221> NAME/KEY: MOD_RES
<222> LOCATION: (10)..(10)
<223> OTHER INFORMATION: Chg

<400> SEQUENCE: 484

Trp Ala Gln Asp Ile Leu Asp Lys His Gly Gln Arg Val Trp Gly
1               5                   10                  15
```

```
<210> SEQ ID NO 485
<211> LENGTH: 14
<212> TYPE: PRT
<213> ORGANISM: Homo sapiens

<400> SEQUENCE: 485

Pro Gln Lys Ile Leu Asp Glu His Val Gln Arg Val Met Lys
1               5                   10

<210> SEQ ID NO 486
<211> LENGTH: 14
<212> TYPE: PRT
<213> ORGANISM: Homo sapiens

<400> SEQUENCE: 486

Pro Gln Lys Ile Leu Asp Glu His Val Gln Arg Val Met Lys
1               5                   10

<210> SEQ ID NO 487
<211> LENGTH: 14
<212> TYPE: PRT
<213> ORGANISM: Homo sapiens

<400> SEQUENCE: 487

Pro Gln Lys Ile Leu Asp Glu His Val Gln Arg Val Met Lys
1               5                   10

<210> SEQ ID NO 488
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Chg

<400> SEQUENCE: 488

Pro Gln Lys Ile Leu Asp Glu His Gly Gln Arg Val Met Lys
1               5                   10

<210> SEQ ID NO 489
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Chg

<400> SEQUENCE: 489

Pro Gln Lys Ile Leu Asp Glu His Gly Gln Arg Val Met Lys
1               5                   10

<210> SEQ ID NO 490
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Chg

<400> SEQUENCE: 490

Pro Gln Lys Ile Leu Asp Glu His Gly Gln Arg Val Met Lys
1               5                   10
```

```
<210> SEQ ID NO 491
<211> LENGTH: 9
<212> TYPE: PRT
<213> ORGANISM: Homo sapiens

<400> SEQUENCE: 491

Met Trp Phe Leu Ile Cys Phe Trp Gly
1               5

<210> SEQ ID NO 492
<211> LENGTH: 9
<212> TYPE: PRT
<213> ORGANISM: Homo sapiens

<400> SEQUENCE: 492

Met Trp Ile Leu Ile Ser Phe Trp Gly
1               5

<210> SEQ ID NO 493
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Cha
<220> FEATURE:
<221> NAME/KEY: MOD_RES
<222> LOCATION: (6)..(6)
<223> OTHER INFORMATION: Abu

<400> SEQUENCE: 493

Lys Trp Ala Leu Ile Xaa Ala Trp Asp
1               5

<210> SEQ ID NO 494
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Cha
<220> FEATURE:
<221> NAME/KEY: MOD_RES
<222> LOCATION: (6)..(6)
<223> OTHER INFORMATION: Abu

<400> SEQUENCE: 494

Lys Trp Ala Leu Ile Xaa Ala Trp Asp
1               5

<210> SEQ ID NO 495
<211> LENGTH: 9
<212> TYPE: PRT
<213> ORGANISM: Homo sapiens

<400> SEQUENCE: 495

Met Trp Phe Leu Ile Cys Phe Trp Gly
1               5

<210> SEQ ID NO 496
<211> LENGTH: 9
<212> TYPE: PRT
<213> ORGANISM: Homo sapiens

<400> SEQUENCE: 496

Met Trp Ile Leu Ile Ser Phe Trp Gly
```

```
<210> SEQ ID NO 497
<211> LENGTH: 9
<212> TYPE: PRT
<213> ORGANISM: Homo sapiens

<400> SEQUENCE: 497

Met Trp Phe Leu Ile Cys Phe Trp Gly
1               5

<210> SEQ ID NO 498
<211> LENGTH: 9
<212> TYPE: PRT
<213> ORGANISM: Homo sapiens

<400> SEQUENCE: 498

Met Trp Ile Leu Ile Ser Phe Trp Gly
1               5

<210> SEQ ID NO 499
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(18)
<223> OTHER INFORMATION: a, c, t or g
<220> FEATURE:
<221> NAME/KEY: modified_base
<222> LOCATION: (20)..(21)
<223> OTHER INFORMATION: a, c, t or g
<220> FEATURE:
<221> NAME/KEY: modified_base
<222> LOCATION: (23)..(24)
<223> OTHER INFORMATION: a, c, t or g
<220> FEATURE:
<221> NAME/KEY: modified_base
<222> LOCATION: (26)..(27)
<223> OTHER INFORMATION: a, c, t or g
<220> FEATURE:
<221> NAME/KEY: modified_base
<222> LOCATION: (29)..(30)
<223> OTHER INFORMATION: a, c, t or g
<220> FEATURE:
<221> NAME/KEY: modified_base
<222> LOCATION: (32)..(33)
<223> OTHER INFORMATION: a, c, t or g
<220> FEATURE:
<221> NAME/KEY: modified_base
<222> LOCATION: (35)..(36)
<223> OTHER INFORMATION: a, c, t or g
<220> FEATURE:
<221> NAME/KEY: modified_base
<222> LOCATION: (38)..(39)
<223> OTHER INFORMATION: a, c, t or g
<220> FEATURE:
<221> NAME/KEY: modified_base
<222> LOCATION: (41)..(42)
<223> OTHER INFORMATION: a, c, t or g
<220> FEATURE:
<221> NAME/KEY: modified_base
<222> LOCATION: (44)..(45)
<223> OTHER INFORMATION: a, c, t or g

<400> SEQUENCE: 499
gccagacccc gatttsnnsn nsnnsnnsnn snnsnnsnns nnsnncattg taattgtaaa      60
tagtaattg                                                             69
```

```
<210> SEQ ID NO 500
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
taatacgact cactataggg acaattacta tttacaatta ca                             42

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
accgctgcca gacccccgatt t                                                   21

<210> SEQ ID NO 502
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
aaaaaaaaaa aaaaaaaaa a                                                     21

<210> SEQ ID NO 503
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
tttttttttt tttaccgctg ccagac                                               26

<210> SEQ ID NO 504
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys or Arg

<400> SEQUENCE: 504

Met Ser Arg Xaa Met Trp Phe Leu Leu Cys Phe Trp Gly
1               5                   10
```

COMPOSITIONS AND METHODS FOR TREATING ENDOMETRIOSIS

CROSS REFERENCE

This application is a § 371 U.S. National Stage Entry of International Application No. PCT/US2019/062679, filed Nov. 21, 2019, which claims the benefit of U.S. Provisional Application No. 62/770,601, filed Nov. 21, 2018, which are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 11, 2023, is named 54455-701_831_SL.txt and is 106,279 bytes in size.

FIELD

The present disclosure relates to agents and methods, formulations, and devices for administering such agents for treating diseases or conditions in a subject. Among the provided agents are those that can inhibit certain cellular proteins or functions, including inhibitors of β-catenin and Wnt. The agents can include therapeutic peptides and peptidomimetic agents. Features of the methods provide various advantages for treating conditions such as endometriosis, such as the ability treat or reverse the root causes of endometriosis and reduce or eliminate the need to administer hormonal therapies in order to ameliorate the symptoms associated with endometriosis.

BACKGROUND

Endometriosis (EMS) affects ~10% of women and adolescents: more than 7.4 million women in the US and more than 176 million women worldwide. EMS is the #1 cause of disability and infertility among women in their reproductive years; 40% of infertile women have EMS. The average age at diagnosis is 28 years. Debilitating symptoms include painful menstruation, chronic pain, pain with intercourse, and infertility (Giudice, L. C. & Kao, L. C., Lancet 364, 1789-1799). In addition to human suffering, the symptom-associated productivity loss and direct health-care cost to the United States is greater than $90 billion annually. EMS occurs via retrograde menstruation, where viable endometrial tissue flows back through the fallopian tubes and into the peritoneal cavity. There it attaches to multiple foreign sites (e.g. fallopian tubes, ovarian fossa, peritoneal wall, ligaments, and bowel) and responds to hormones (Sampson, J. A., Am J Pathol 3, 93-110 143, 1927). Current therapies are only able to suppress symptoms and are not curative. Recurrences are common and can occur quickly if therapies are discontinued.

Hormonal based therapies are used to alter ovulation cycles to reduce retrograde menstruation and treat EMS symptoms. These include combined estrogen/progesterone therapies, progestin-only treatments, or GnRH antagonists/agonists (i.e. "medical menopause"), which decreases hormonal activation to suppress ovulation; however, these therapies only suppress EMS symptoms and do not cure disease. Upon cessation of therapy, symptom reoccurrence is ~70% (Selcuk, I. et al., Ger Gynecol Assoc 14, 98-103, 2013). Managing EMS via hormone regulation fails to reverse existing lesions; does not hinder growth of lesions caused by other factors (e.g. oxidative stress or genetics); is hindered by progesterone receptor (PGR) resistance found in most women with EMS; and is accompanied by unfavorable side effects. The limitations of hormone therapeutics for EMS have resulted in limited efficacy, low adherence to protocol, and the need for invasive surgery.

While surgery remains a fundamental tool in diagnosing and managing endometriosis, even surgery is not curative; the main objective of surgical intervention is to prevent recurrence and reduce symptoms in order to eliminate the need for or prolong the time between additional surgeries.

Thus, there is a need for non-hormonal, non-surgical treatments for EMS.

SUMMARY

Provided herein are peptides and peptidomimetic agents comprising an amino acid sequence having the formula $X_1$—$X_2$—$X_3$—$X_4$—$X_5$—$X_6$—$X_7$—$X_8$—$X_9$—$X_{10}$—$X_{11}$—$X_{12}$—$X_{13}$—$X_{14}$—$X_{15}$—$X_{16}$, wherein: $X_1$ is M or null; $X_2$ is S, I, G, T, A, L, or null; $X_3$ is R, K or null; $X_4$ is a positively-charged amino acid, citrulline, Orn, D, E, 8-aminooctanoic acid, or an amino carboxylic acid with between 4 and 12 carbons; $X_5$ is M, Norleucine, Orn, D, E, K, H, R, K, 8-aminooctanoic acid, an amino carboxylic acid with between 4 and 12 carbons or null; $X_6$ is W, Y, F, or N-methyl A; $X_7$ is F, I, L, Chg, Cha, or Tle; $X_8$ is L, I, or A; $X_9$ is L, I, or A; $X_{10}$ is C, S, A, Abu, C(me), or S(Bzl); $X_{11}$ is F, H, A, K, E, Chg, Cng, or Orn; $X_{12}$ is W, Y, A, or F; and $X_{13}$ is G, GABA, or null.

Provided herein are peptides and peptidomimetic agents comprising an amino acid sequence having the formula R—$X_1$—$X_2$—$X_3$—$X_4$—$X_5$—$X_6$—$X_7$—$X_8$—$X_9$—$X_{10}$—$X_{11}$—$X_{12}$—$X_{13}$—$X_{14}$—$X_{15}$—$X_{16}$, wherein: R is $NH_2$, acetylation, stearic acid, palmitic acid, myristic acid, lauric acid, a $C_1$-$C_8$ hydrocarbon, a $C_1$-$C_8$ fatty acid, or null; $X_1$ is M, G, beta alanine, norleucine, norvaline, or null; $X_2$ is W, N-methyl W, R, Y, F, citrulline, or K; $X_3$ is P, W, N-methyl-W, N-ethyl-W, N-methyl A, N-ethyl A, L, Pip, Aib, Y, or F; $X_4$ is E, Q, N, or D; $X_5$ is S, alpha methyl S, K, D, Orn, T, or E; $X_6$ is I, Chg, H, or L; $X_7$ is L or I; $X_8$ is D, N, E, or Q; $X_9$ is D, E, K, Q, or Orn; $X_{10}$ is H or methyl-H; $X_{11}$ is V, alpha methyl V, Chg, L I, or norvaline; $X_{12}$ is Q, Aib, S, R, or N; $X_{13}$ is R, K, citrulline, Orn, D, or E; $X_{14}$ is V, I, L, or norvaline; $X_{15}$ is W, Y, or F; and $X_{16}$ is R, G, or null.

Provided herein are peptides and peptidomimetic agents comprising an amino acid sequence of any one of SEQ ID NO: 1-SEQ ID NO: 500.

Provided herein are peptides and peptidomimetic agents comprising an amino acid sequence having at least 80%, 85%, 90%, 95%, 96%, 97%, 98%, 99%, or 100% sequence identity to any one of SEQ ID NO: 1-SEQ ID NO: 500.

In some embodiments, the peptide binds to β-catenin. In some embodiments, the peptide is a β-catenin inhibitor. In some embodiments, the peptide is an inhibitor of β-catenin translocation to the nucleus. In some embodiments, the peptide prevents β-catenin acting as a transcription factor to oncogenes, Matrix Metalloproteinase 9 (MMP9), or Chloride C3 Channel (ClC-3). In some embodiments, the peptide prevents transformation, invasion, migration, fibrogenesis, or any combination thereof, of endometriosis (EMS) cells. In some embodiments, the peptide prevents β-catenin from binding to estrogen receptor (ESR1). In some embodiments, the peptide does not decrease membrane activity of β-catenin. In some embodiments, the peptide does not decrease β-catenin E-cadherin binding. In some embodiments, the peptide prevents oncogenic transcription factor activity. In some embodiments, the peptide inhibits Wnt pathway activity with an $EC_{50}$ of less than 50 uM, less than 30uM, less than 10uM, 5 uM, 1 uM, 500 nM, 400 nM, 300 nM, 200 nM, 100 nM, 50 nM, 30 nM, 10 nM, 5 nM, 3 nM, 1 nM, 800 pM, 600 pM, 400 pM, 200 pM, 100 pM, 50 pM, 30 pM, 20 pM, 10 pM, or 5 pM or less than about 10 uM, about 5 uM, about 1 uM, about 500 nM, about 400 nM, about 300 nM, about 200 nM, about 100 nM, about 50 nM, about 30 nM, about 10 nM, about 5 nM, about 3 nM, about 1 nM, about 800 pM, about 600 pM, about 400 pM, about 200 pM, about 100 pM, about 50 pM, about 30 pM, about 20 pM, about 10 pM, or about 5 pM. In some embodiments, the peptide binds β-catenin with a $KD_{50}$ binding affinity of less than 50 uM, 30 uM , 10 uM $K_D$, 5 uM, 1 uM, 500 nM, 400 nM, 300 nM, 200 nM, 100 nM, 50 nM, 30 nM, 10 nM, 5 nM, 3 nM, 1 nM, 800 pM, 600 pM, 400 pM, 200 pM, 100 pM, 50 pM, 30 pM, 20 pM, 10 pM, or 5 pM or less than about 10 uM, about 5 uM, about 1 uM, about 500 nM, about 400 nM, about 300 nM, about 200 nM, about 100 nM, about 50 nM, about 30 nM, about 10 nM, about 5 nM, about 3 nM, about 1 nM, about 800 pM, about 600 pM, about 400 pM, about 200 pM, about 100 pM, about 50 pM, about 30 pM, about 20 pM, about 10 pM, or about 5 pM. In some embodiments, the peptide is non-naturally occurring. In some embodiments, the peptide is a circularized peptide. In some embodiments, the peptide is a bicyclic peptide. In some embodiments, the peptide is circularized with a Cys-Cys disulfide bond. In some embodiments, the peptide is circularized with an amide bond. In some embodiments, the amide bond is head-to-tail between N-terminus and C-terminus. In some embodiments, the amide bond is head-to-side chain between N-terminus and an internal COOH. In some embodiments, the amide bond is side chain-to-tail between an internal $NH_2$ and C-terminus. In some embodiments, the amide bond is side chain-to-side chain between an internal $NH_2$ and an internal COOH. In some embodiments, the peptide is circularized using hydrocarbon stapling. In some embodiments, the peptide is circularized using click chemistry. In some embodiments, the peptide is at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, or at least 81 amino acid residues. In some embodiments, the peptide is less than 4, less than 5, less than 6, less than 7, less than 8, less than 9, less than 10, less than 11, less than 12, less than 13, less than 14, less than 15, less than 16, less than 17, less than 18, less than 19, less than 20, less than 21, less than 22, less than 23, less than 24, less than 25, less than 26, less than 27, less than 28, less than 29, less than 30, less than 31, less than 32, less than 33, less than 34, less than 35, less than 36, less than 37, less than 38, less than 39, less than 40, less than 41, less than 42, less than 43, less than 44, less than 45, less than 46, less than 47, less than 48, less than 49, less than 50, less than 51, less than 52, less than 53, less than 54, less than 55, less than 56, less than 57, less than 58, less than 59, less than 60, less than 61, less than 62, less than 63, less than 64, less than 65, less than 66, less than 67, less than 68, less than 69, less than 70, less than 71, less than 72, less than 73, less than 74, less than 75, less than 76, less than 77, less than 78, less than 79, less than 80, or less than 81 amino acid residues. In some embodiments, the peptide comprises one or more non-natural amino acids. In some embodiments, the one or more non-natural amino acids are N-methyl amino acids.

Provided herein are pharmaceutical compositions comprising: a β-catenin inhibitor; and a pharmaceutically acceptable carrier.

Provided herein are pharmaceutical compositions comprising: a peptide comprising binding specificity to β-catenin; and a pharmaceutically acceptable carrier.

Provided herein are pharmaceutical compositions comprising: a β-catenin inhibitor comprising a peptide; and a pharmaceutically acceptable carrier.

Provided herein are pharmaceutical compositions comprising: peptides as described herein; and a pharmaceutically acceptable carrier. In some embodiments, the peptide is a circularized peptide. In some embodiments, the composition comprises an absorption or permeation enhancer. In some embodiments, the absorption enhancer comprises one or more of, sulphoxides, such as dimethyl sulphoxides (DMSO); laurocapran (1-dodecylazacycloheptan-2-one); pyrrolidones, such as n-methyl-2-pyrrolidone; terpenes and terpenoids; essential oils; oxazolidinones, such as 4-decy-cloxazolidin-2-one; urea; cyclopentadecalactone; sodium N-[8-(2-hydroxylbenzoyl)amino] caprylate (SNAC); 8-(N-2-hydroxy-5-chloro-benzoyl)-amino-caprylic acid (5-CNAC); medium chain fatty acids, salts, and derivatives; sodium caprate; sodium caprylate; protease inhibitor and omega-3 fatty acid; liquid mixed-micelle spray; lipid polymer micelle; alkylglycosides; chitosan; dodecyl-2-N,N-dimethylamino propionate (DDAIP); cell-membrane-lipid components; nanoparticles; liposomes, ligands; and lipophilic modifications. In some embodiments, the absorption enhancer is sodium caprate.

Provided herein are formulations comprising peptides or pharmaceutical compositions as described herein, wherein the formulation comprises a solution, lotion, shake lotion, cream, ointment, gel, foam, powder, solid, paste, tincture, microparticle, microcapsule, nanoparticle, liposome, emulsion, or lyophilisate. Further described herein are formulations, wherein the gel is a thermoreversible gel. Further described herein are formulations, wherein the formulation comprises one or more mucoadhesive polymers. Further described herein are formulations, wherein the formulation is for topical administration.

Provided herein are intravaginal devices comprising peptides or pharmaceutical compositions as described herein. In some embodiments, the intravaginal device is a suppository, transdermal patch, sponge, tape, film, intravaginal ring, vaginal tampon, vaginal ring, vaginal strip, vaginal capsule, vaginal tablet, vaginal pessary, vaginal cup, vaginal sponge, or intrauterine device. In some embodiments, the peptide or the pharmaceutical composition is formulated as a formulation selected from the group consisting of a solution, lotion, shake lotion, cream, ointment, gel, foam, mucoadhesive composition, coating, core, matrix, emulsion, liposomes, or lyophilisate, wherein the intravaginal device comprises the formulation. In some embodiments, the intravaginal device comprises from about 0.01 mg to about 5000 mg of inhibitor In some embodiments, the intravaginal device comprises about 0.01 mg, about 0.05 mg, about 0.1 mg, about 0.5 mg, about 1 mg, about 5 mg, about 10 mg, about 20 mg, about 40 mg, about 60 mg, about 80 mg, about 100 mg, about 150 mg, about 200 mg, about 400 mg, about 600 mg, about 800 mg, about 1000 mg, about 1200 mg, about 1400 mg, about 1600 mg, about 1800 mg, about 2000 mg, about 2500 mg, about 3000 mg, about 3500 mg, about 4000 mg, about 4500 mg, or about 5000 mg inhibitor. In some embodiments, the intravaginal device is configured to deliver the inhibitor transmucosally. In some embodiments, the intravaginal device is configured to deliver inhibitor over 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 18 hours, 19 hours, 20 hours, 21 hours, 22 hours, 23 hours, 24 hours, 1 day, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 1 month, 2 months, 3 months, 4 months, 5 months, 6 months, 7 months, 8 months, 9 months, 10 months, 11 months, 12 months, 1 year, 2 years, 3 years, 4 years, 5 years, 6 years, 7 years, 8 years, 9 years, 10 years, 11 years, or 12 years. In some embodiments, the intravaginal device is configured to deliver from about 0.01 mg to about 1000 mg inhibitor/day. In some embodiments, the intravaginal device is configured to deliver about 0.01 mg, about 0.05 mg, about 0.1 mg, about 0.5 mg, about 1 mg, about 5 mg, about 10 mg, about 20 mg, about 40 mg, about 60 mg, about 80 mg, about 100 mg, about 150 mg, about 200 mg, about 400 mg, about 600 mg, about 800 mg, or about 1000 mg inhibitor/day. In some embodiments, the device is the suppository. In some embodiments, the device is the transdermal patch. In some embodiments, the device is the sponge. In some embodiments, the device is the tape. Further provided herein are intravaginal devices, wherein the device is the intravaginal ring. In some embodiments, the intravaginal ring comprises a silicone insert, a compressed tablet, or a lyophilized gel. In some embodiments, the peptide or the composition is incorporated throughout the silicone insert, the compressed tablet, or the lyophilized gel. In some embodiments, the device is the vaginal tampon. In some embodiments, the device is the vaginal ring. In some embodiments, the device is the vaginal strip. In some embodiments, the device is the vaginal capsule. In some embodiments, the device is the vaginal tablet. In some embodiments, the device is the vaginal pessary. In some embodiments, the device is the vaginal cup. In some embodiments, the device is the vaginal sponge. In some embodiments, the device is the intrauterine device.

Provided herein are formulations comprising peptides or pharmaceutical compositions as described herein, wherein the formulation is for oral administration. Further provided herein are formulations, wherein the formulation is a tablet or capsule. In some embodiments, the formulation is a liquid.

Provided herein are methods of inhibiting β-catenin in a subject comprising inserting the devices as described herein into the vagina of the subject.

Provided herein are methods of inhibiting β-catenin comprising contacting a cell with the peptides or the pharmaceutical compositions as described herein.

Provided herein are methods of treating endometriosis comprising administering a therapeutically effective amount of the peptides or the pharmaceutical compositions as described herein to a subject in need thereof.

Provided herein are methods of reducing symptoms associated with endometriosis comprising administering a therapeutically effective amount of the peptides or the pharmaceutical compositions as described herein to a subject in need thereof. In some embodiments, the symptoms comprise at least one selected from the group consisting of chronic pain, central sensitization, myofascial pain, adnexal masses, infertility, dysmenorrhea, genetic predisposition, nonmenstrual pelvic-abdominal pain, dyspareunia, bowel symptoms (diarrhea, cramping, constipation), defecation pain (dyschezia), ovarian mass or tumor, painful bladder symptoms, and dysuria.

Provided herein are methods of treating a condition comprising administering to a subject a therapeutically effective amount of the peptides or the pharmaceutical compositions as described herein. In some embodiments, the condition is a tissue-infiltration condition, a tissue migration condition, a tissue invasion condition, or a combination thereof. In some embodiments, the condition comprises a cancer. In some embodiments, the cancer comprises colorectal carcinoma, squamous cell carcinoma, head and neck cancer, pancreatic cancer, breast cancer, myeloid leukemia, basal cell carcinoma, synovial sarcoma, non-small cell lung cancer, a solid tumor, or prostate cancer. In some embodiments, the condition comprises endometriosis. In some embodiments, the peptide binds to β-catenin. In some embodiments, the peptide inhibits β-catenin. In some embodiments, the peptide binds to cytoplasmic β-catenin. In some embodiments, the peptide binds to cytoplasmic β-catenin to inhibit translocation of β-catenin to a nucleus of a cell. In some embodiments, the peptide binds to cytoplasmic β-catenin to maintain or increase membrane-bound β-catenin. In some embodiments, the peptide binds to cytoplasmic β-catenin to decrease nuclear β-catenin. In some embodiments, the peptide binds to cytoplasmic β-catenin to prevent β-catenin acting as a transcription factor to oncogenes, Matrix Metalloproteinase 9 (MMP9), or Chloride C3 Channel (ClC-3). In some embodiments, the peptide binds to cytoplasmic β-catenin to prevent transformation, invasion, migration, fibrogenesis, or any combination thereof, of EMS cells. In some embodiments, the peptide binds to cytoplasmic β-catenin to prevent β-catenin from binding to estrogen receptor (ESR1). In some embodiments, the peptide binds to cytoplasmic β-catenin and membrane activity of β-catenin is not decreased. In some embodiments, the peptide binds to cytoplasmic β-catenin and β-catenin-E-cadherin binding is not decreased. In some embodiments, the peptide prevents oncogenic transcription factor activity. In some embodiments, the reduction in free cytoplasmic β-catenin is relative to a cell from the subject taken at a different timepoint. In some embodiments, the amount of membrane-bound cytoplasmic β-catenin in a cell of the subject is increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or at least 100%. In some embodiments, the increase in membrane-bound cytoplasmic β-catenin is relative to a cell of a control subject who was not administered the therapeutically effective amount of the pharmaceutical composition. In some embodiments, the increase in membrane-bound β-catenin is relative to a cell of the subject taken prior to the subject developing the condition. In some embodiments, the increase in membrane-bound β-catenin is relative to a cell from the subject taken at a different timepoint. In some embodiments, the amount of nuclear β-catenin in a cell of the subject is reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or at least 100%. In some embodiments, the reduction in nuclear β-catenin is relative to a cell of a control subject who was not administered the therapeutically effective amount of the pharmaceutical composition. In some embodiments, the reduction in nuclear β-catenin is relative to a cell of the subject taken prior to the subject developing the condition. In some embodiments, the reduction in nuclear β-catenin is relative to a cell from the subject taken at a different timepoint.

In some embodiments, the therapeutically effective amount is from about 0.01 mg to about 1000 mg.

Provided herein are methods of preventing a condition comprising administering to a subject a therapeutically effective amount of the peptides or the pharmaceutical compositions as described herein. In some embodiments, the condition is a tissue-infiltration condition, a tissue migration condition, a tissue invasion condition, or a combination thereof. In some embodiments, the condition comprises a cancer. In some embodiments, the cancer comprises colorectal carcinoma, squamous cell carcinoma, head and neck cancer, pancreatic cancer, breast cancer, myeloid leukemia, basal cell carcinoma, synovial sarcoma, non-small cell lung cancer, a solid tumor, or prostate cancer. In some embodiments, the condition comprises endometriosis. In some embodiments, the peptide binds to β-catenin. In some embodiments, the peptide inhibits β-catenin. In some embodiments, the peptide binds to cytoplasmic β-catenin. In some embodiments, the peptide binds to cytoplasmic β-catenin to inhibit translocation of β-catenin to a nucleus of a cell. In some embodiments, the peptide binds to cytoplasmic β-catenin to maintain or increase an amount of membrane-bound β-catenin. In some embodiments, the peptide binds to cytoplasmic β-catenin to prevents β-catenin acting as a transcription factor to oncogenes, Matrix Metalloproteinase 9 (MMP9), or Chloride C3 Channel (ClC-3). In some embodiments, the peptide prevents transformation, invasion, migration, fibrogenesis, or any combination thereof, of EMS cells. In some embodiments, the peptide prevents β-catenin from binding to estrogen receptor (ESR1). In some embodiments, the peptide binds to cytoplasmic β-catenin and membrane activity of β-catenin is not decreased. In some embodiments, the peptide binds to cytoplasmic β-catenin and β-catenin-E-cadherin binding is not affected. In some embodiments, the peptide prevents oncogenic transcription factor activity. In some embodiments, the amount of nuclear β-catenin in a cell of the subject is reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or at least 100%. In some embodiments, the reduction in nuclear β-catenin is relative to a cell of a control subject who was not administered the therapeutically effective amount of the pharmaceutical composition. In some embodiments, the reduction in nuclear β-catenin is relative to a cell of the subject taken prior to the subject developing the endometriosis or tissue-infiltrating condition. In some embodiments, the reduction in nuclear β-catenin is relative to a cell from the subject taken at a different timepoint. In some embodiments, the therapeutically effective amount is from about 0.01 mg to about 1000 mg. In some embodiments, the peptide or pharmaceutical composition is administered intravenously. In some embodiments, the peptide or pharmaceutical composition is administered intramuscularly. In some embodiments, the peptide or pharmaceutical composition is administered concurrently to administration of a medication to treat osteoporosis. In some embodiments, the medication to treat osteoporosis comprises alendronate, ibandronate, risedronate, zoledronic acid, denosumab, calcitonin, estrogen, raloxifene, bazodoxifene, teriparatide, abaloparatide, or any combination thereof. In some embodiments, the medication to treat osteoporosis is zoledronic acid.

Provided herein is an intravaginal device comprising a peptide comprising an amino acid sequence of SEQ ID NO: 215 or 393 formulated to release peptide in a time-controlled manner, wherein the peptide binds β-catenin, wherein the peptide inhibits translocation of β-catenin to a nucleus of a cell, wherein the peptide does not decrease β-catenin binding E-cadherin in the membrane; and wherein the peptide reduces size or severity of endometriosis lesions or other symptoms associated with endometriosis in a subject in need thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 4A shows analysis of daily vaginal smears to assess estrous cycle stage. FIG. 4B shows Peptide 2 (SEQ ID NO: 215) demonstrates regression of lesions. FIG. 4C shows images of lesions treated with either vehicle or Peptide 2. Two images of lesions (L) are shown for each treatment. Donor mice express green fluorescent protein and lesions are green. Magnification=7.5 ×.

FIG. 6B shows representative slides at 120× magnification of stained mouse model endometriosis lesions showing β-catenin localizes more in the membrane in peptide-treated samples than in control-treated mice.

DETAILED DESCRIPTION

Figure 1:
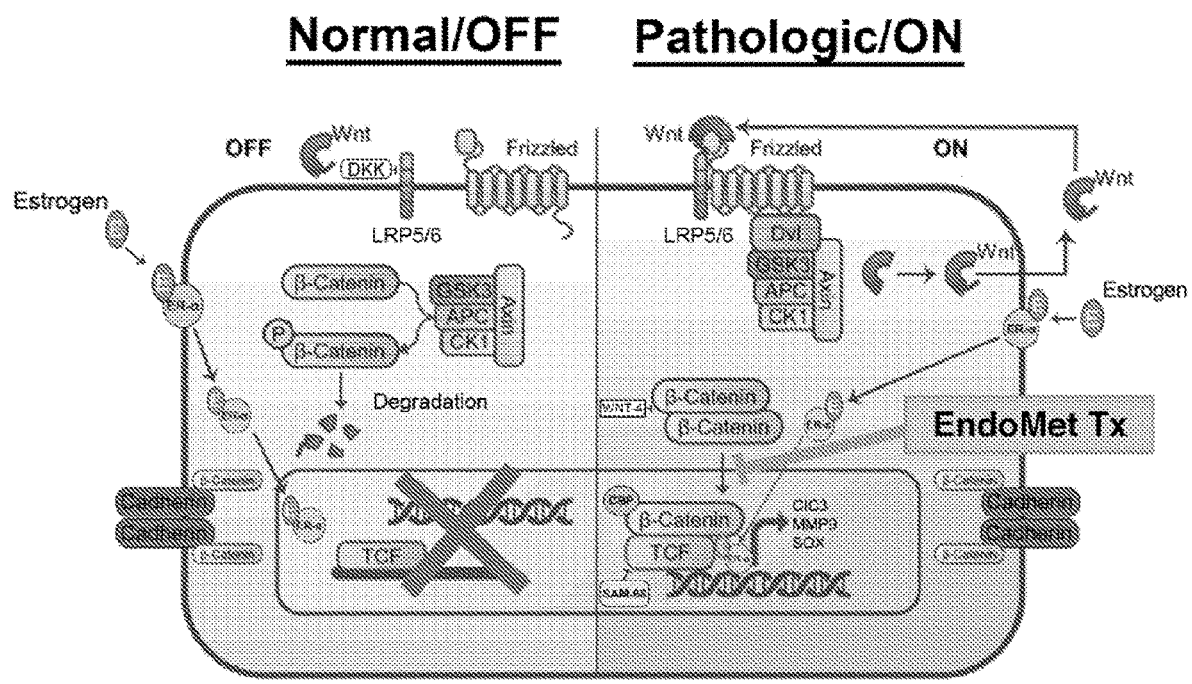
FIG. 1 shows the Wnt/β-catenin signal transduction pathway in the "Off" and "On" states.

Provided herein are agents, compositions, methods, and articles of manufacture for use in conjunction with treating therapy, for example, for the treatment of various diseases and conditions. In some cases, the diseases and conditions can include endometriosis. The methods can involve administering to a subject an inhibitor, or a composition, formulation, or device comprising an inhibitor. Exemplary inhibitors include β-catenin inhibitors. The inhibitor can be or can include a peptide, such as an isolated peptide or a combination of peptides.

I. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof The terms "determining", "measuring", "evaluating", "assessing, " "assaying, " and "analyzing" are often used interchangeably herein to refer to forms of measurement, and include determining if an element is present or not (for example, detection). These terms can include quantitative, qualitative or quantitative and qualitative determinations. Assessing is alternatively relative or absolute. "Detecting the presence of" includes determining the amount of something present, as well as determining whether it is present or absent.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. The disease can be endometriosis. In some cases, the subject is not necessarily diagnosed or suspected of being at high risk for the disease.

The term "in vivo" is used to describe an event that takes place in a subject's body.

The term "ex vivo" is used to describe an event that takes place outside of a subject's body. An "ex vivo" assay is not performed on a subject. Rather, it is performed upon a sample separate from a subject. An example of an "ex vivo" assay performed on a sample is an "in vitro" assay.

The term "in vitro" is used to describe an event that takes places contained in a container for holding laboratory reagent such that it is separated from the living biological source organism from which the material is obtained. In vitro assays can encompass cell-based assays in which cells alive or dead are employed. In vitro assays can also encompass a cell-free assay in which no intact cells are employed.

As used herein, the term 'about' a number refers to that number plus or minus 10% of that number. The term 'about' a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The abbreviations for many of the terms used in sequences herein are defined in Table 1.

TABLE 1

| Key | |
|---|---|
| ND | not determined |
| Blank | experiment not performed |
| My | myristic acid |
| COOH | Carboxylate |
| H2N | Amino |
| NMeX | N-methyl amino acid. X is any amino acid. For example NMeA = N-methyl alanine |
| X* | An amino acid used in cyclization. For example, K* is K with its side chain used in cyclization |
| Aoc | 8-amino caprylic acid |
| Cyclo | Cyclic |
| Pra | propargyl glycine |
| AmeX | Alpha methyl amino acid |
| S(Et) | Serine with a ethyl ether on its side chain |
| S(Bzl) | O-benzyl-L-serine |
| dX | D amino acid |
| GABA | Gamma aminobutyric acid |
| Nle | Norleucine |
| Ac | Acetyl |
| Tle | Tert-leucine |
| Cha | 3-cyclohexyl-L-alanine |
| Chg | Cyclohexylglycine |

TABLE 1-continued

| Key | |
|---|---|
| Bz | Benzyl |
| Piv | Pivalic acid |
| β | Beta Alanine |
| Ava | amino valeric acid |
| Ahx | amino caproic acid |
| Adc | amino decanoic acid |
| 2-Pyr | 2-pyridine |
| O | Ornithine |
| Pip | pipecolic acid |
| St- | Stearyl- (stearic acid) |

The section headings used herein are for organizational purposes only and are not to be construed as limiting the subject matter described.

II. WNT CANONICAL PATHWAYS-βCATENIN

Wnt pathways are involved in the control of gene expression, cell behavior, cell adhesion, and cell polarity. The Canonical (β-catenin-Dependent) Wnt Signaling pathway is the best studied of the Wnt pathways and is highly conserved through evolution. In this pathway, Wnt signaling inhibits the degradation of β-catenin, which can regulate transcription of a number of genes. Wnt signaling is activated via ligation of Wnt proteins to their respective dimeric cell surface receptors composed of the seven transmembrane frizzled proteins and the LRP5/6. Upon ligation to their receptors, the cytoplasmic protein disheveled (Dvl) is recruited, phosphorylated and activated. Activation of Dvl induces the dissociation of GSK-3β from Axin and leads to the inhibition of GSK-3β. Next, the phosphorylation and degradation of β-catenin is inhibited as a result of the inactivation of the "destruction complex." Subsequently, stabilized β-catenin translocates into the nucleus leading to changes in different target gene expressions.

In healthy cells, β-catenin is typically bound to E-cadherin at the cellular membrane and is regulated by the Wnt pathway, as shown in FIG. 1. In healthy gynecological epithelia, high concentrations of β-catenin are often found at the membrane with low concentrations in the cytoplasm and nucleus (Aberle, H., et al., EMBO J 16, 3797-3804, 1997; Jha, R. K., et al., FEBS Lett 580, 5653-5660, 2006; Lee, K. Y., et al., Trends Endocrinol Metab 18, 234-239, 2007; Jeong, J. W. et al., Oncogene 28, 31-40, 2009 each of which is incorporated by reference herein for such disclosure). The Wnt/β-catenin signal transduction pathway is turned "Off", (β-catenin interacts with a destruction complex, which phosphorylates β-catenin and targets it for proteasome degradation.

Conversely, in Wnt pathway dysregulation, β-catenin often dissociates from the membrane and accumulates in the cytoplasm. Once in the cytoplasm, β-catenin is often able to translocate into the nucleus, where it can function as a transcription factor to oncogenes (Clevers, H., Cell 127, 469-480, 2006), Matrix Metalloproteinase 9 (MMP9), Chloride 3 Channel (ClC-3), and other Wnt pathway-activated proteins. These proteins are believed to be able to initiate the transformation, invasion, migration, and fibrogenesis of EMS cells (Guan, Y. T. et al., Hum Reprod 31, 986-998, 2016) (Matsuzaki, S. et al., Mol Cell Ther 2, 36, 2014) (Zhang, L. et al., Biol Reprod 94, 70, 2016) (Zhang, L. et al., Mol Hum Reprod 22, 526-535, 2016). When the transduction pathway is in the "On" state, cytoplasmic β-catenin can accumulate, translocate to the nucleus, and bind to transcription factors (including ER-α) to stimulate transcription of WNT target genes to produce, for example, ClC3, MMP9, and SOX.

In EMS, β-catenin often disassociates from the membrane by either receptor dysregulation or somatic mutation. It is thought to bind to estrogen receptor (ESR1) and translocate into the nucleus, where it is thought to activate onco/endogenes and give rise to lesions (Valentijn, A. J. et al., Hum Reprod 28, 2695-2708, 2013) (Kouzmenko, A. P. et al., J Biol Chem 279, 40255-40258, 2004).

Maintaining β-catenin's membrane activity is thought to be a hallmark of healthy cells; Wnt antagonists that disrupt β-catenin's membrane binding with E-cadherin are believed to increase concentrations of cytoplasmic β-catenin and cell mobility. This can result in an undesired, proto-oncogene-like effect (Onder, T. T. et al., Cancer Res 68, 3645-3654, 2008). Therefore, a cytoplasmic β-catenin-specific Wnt antagonist capable of inhibiting β-catenin's nuclear translocation and oncogenic transcription factor activity is an attractive approach for treating EMS (Matsuzaki, S. et al., Mol Cell Ther 2, 36, 2014; Xiong, W. et al., Reproduction 150, 507-516, 2015; Pazhohan, A et al., Eur J Obstet Gynecol Reprod Biol 220, 1-5, 2018, each of which is incorporated by reference herein for such disclosure).

Dysregulation of the Wnt pathway is a thought to be present in all lesion subtypes of EMS. For example, cytoplasmic β-catenin translocates to the nucleus and activates target genes. Preventing translocation of β-catenin to the nucleus targets the downstream initiators of EMS without causing the unwanted side effects from targeting upstream receptors. Wnt antagonists can reverse endometriotic lesions. To date, four Wnt antagonists (PKF 115-584, CGP049090, niclosamide, and (β-catenin siRNA) have successfully reversed EMS lesion progression across the subtypes of EMS; none has advanced to clinical trials due to of off-target effects. A therapeutic agent that inhibits the translocation of excess cytoplasmic β-catenin and inhibits its transcriptional factor activity without interfering with β-catenin:E-cadherin interactions to maintain membrane protein function will be a significant improvement over therapeutics currently considered in the art.

Normal uterine function typically includes inactivated canonical Wnt pathway and β-catenin predominantly associated with the E-cadherin membrane complex (FIG. 1). Hormonal activation of the Wnt pathway releases β-catenin into the cytoplasm to translocate to the nucleus, activating nuclear transcription activity and leading to EMS pathogenesis.

A. β-Catenin Inhibitors

In some embodiments, the compositions provided herein include β-catenin inhibitors. The β-catenin inhibitors can be useful in a variety of therapeutic settings including, for example, treating, inhibiting, preventing, or reducing EMS and its related symptoms. Such inhibitors may be able to directly address EMS etiology, reverse disease progression, and prevent or delay EMS recurrence. In some cases, the β-catenin inhibitors can shrink existing EMS lesions. In some cases, β-catenin inhibitors can inhibit dysregulation of the Wnt pathway, which is believed to be one of the underlying causes of EMS. The β-catenin inhibitors can sometimes limit EMS pathogenesis by preventing endometrial cell invasiveness. Alternatively or in addition, the β-catenin inhibitors can suppress epithelial to mesenchymal transition (EMT). This suppression can limit proliferation of endometriotic lesions. Alternatively or in addition, the β-catenin inhibitors can sometimes reduce paracrine production of TGF-β1 and Wnt1, which in turn can diminish fibrogenesis in ovarian endometriomas. Moreover, the β-catenin inhibitors can sometimes reduce MMP9 expression, which can result in reduced angiogenesis. Inhibiting or reducing angiogenesis can inhibit the ability of endometrial cells to grow outside the uterus.

As an exemplary advantage, targeting β-catenin can reduce unwanted side effects associated with targeting upstream receptors. In some cases, these side effects can include excessive estrogen production. In some cases, the inhibitors preferentially inhibit the ability of β-catenin to translocate from the cytoplasm to the nucleus. In some cases, the inhibitors preferentially inhibit the transcriptional activity of β-catenin. These exemplary features can advantageously leave the membrane functions of β-catenin largely or completely intact, which can, in some cases, reduce the side effects associated with inhibiting Wnt function. Thus, in some cases the inhibitors do not inhibit the binding of β-catenin to the cell membrane.

In some cases, the inhibitors do not interfere with the ability of β-catenin to bind to binding factors, which can lead to side effects. For example, in some aspects, the inhibitors may not interfere with the binding or interactions between β-catenin and E-cadherin or adenomatous polyposis coli (APC) or may not disrupt nuclear TCF binding to DNA.

1. Peptides

In some embodiments, the β-catenin inhibitor comprises a peptide. In some cases, the peptides correspond to, such as are based on or derived from, a protein or peptide that binds to β-catenin. In some cases, the peptide contains a synthetic peptide sequence.

The peptides described herein may be optimized for affinity for their desired target, absorption or cellular uptake, stability, protease resistance, and other factors. The affinity of a peptide for its intended target can be altered using a variety of methods. For example, the affinity can be improved with amino acid substitutions. Additionally, modifying the size of a peptide, modifying the position of cyclization, increasing hydrophobicity, and modifying the amino acids or incorporating artificial amino acids into the structure of the peptide can affect the affinity of a peptide. Exemplary modifications include incorporating N-methyls and alpha-methyl amino acids.

Among the provided embodiments are peptidomimetic agents comprising the same or similar structures and properties as the peptides described herein. Such peptidomimetic agents include small protein-like chains designed to mimic a peptide. These include peptidomimetic agents comprising modifications of a peptide, or by designing similar systems that mimic peptides, such as peptoids and β-peptides.

Exemplary peptides include SEQ ID NO: 1-SEQ ID NO: 500, as listed in Table 4. Peptides generally identified in to one of two families: 1, having homology to the TCF4/β-catenin binding region and 2, having similar sequence to β-catenin binding stapled peptides. In some cases, the peptide comprises an amino acid sequence having at least 80%, 85%, 90%, 95%, 96%, 97%, 98%, 99%, or 100% sequence identity to any one of SEQ ID NO: 1-SEQ ID NO: 500.

Alternatively or in addition, the peptide can comprise a sequence having the formula $X_1$—$X_2$—$X_3$—$X_4$—$X_5$—$X_6$—$X_7$—$X_8$—$X_9$—$X_{10}$—$X_{11}$—$X_{12}$—$X_{13}$—$X_{14}$—$X_{15}$—$X_{16}$. In some embodiments, $X_1$ is M or null. In some embodiments, $X_2$ is S, I, G, T, A, L, or null; $X_3$ is R, K or null. In some embodiments, $X_4$ is a positively-charged amino acid, citrulline, Orn, D, E, 8-aminooctanoic acid, or an amino carboxylic acid with between 4 and 12 carbons. In some embodiments, $X_5$ is M, Norleucine, Orn, D, E, K, H, R, K, 8-aminooctanoic acid, an amino carboxylic acid with between 4 and 12 carbons or null. In some embodiments, $X_6$ is W, Y, F, or N-methyl A. In some embodiments, $X_7$ is F, I, L, Chg, Cha, or Tle. In some embodiments, $X_8$ is L, I, or A. In some embodiments, $X_9$ is L, I, or A. In some embodiments, $X_{10}$ is C, S, A, Abu, C(me), or S(Bzl). In some embodiments, $X_{11}$ is F, H, A, K, E, Chg, Cng, or Orn. In some embodiments, $X_{12}$ is W, Y, A, or F. In some embodiments, $X_{13}$ is G, GABA, or null. In some embodiments, $X_1$ is M or null; $X_2$ is S, I, G, T, A, L, or null; $X_3$ is R, K or null; $X_4$ is a positively-charged amino acid, citrulline, Orn, D, E, 8-aminooctanoic acid, or an amino carboxylic acid with between 4 and 12 carbons; $X_5$ is M, Norleucine, Orn, D, E, K, H, R, K, 8-aminooctanoic acid, an amino carboxylic acid with between 4 and 12 carbons or null; $X_6$ is W, Y, F, or N-methyl A; $X_7$ is F, I, L, Chg, Cha, or Tle; $X_8$ is L, I, or A; $X_9$ is L, I, or A; $X_{10}$ is C, S, A, Abu, C(me), or S(Bzl); $X_{11}$ is F, H, A, K, E, Chg, Cng, or Orn; $X_{12}$ is W, Y, A, or F; and $X_{13}$ is G, GABA, or null.

Alternatively or in addition, the peptide can comprise a sequence having the formula R-$X_1$—$X_2$—$X_3$—$X_4$—$X_5$—$X_6$—$X_7$—$X_8$—$X_9$—$X_{10}$—$X_{11}$—$X_{12}$—$X_{13}$—$X_{14}$—$X_{15}$—$X_{16}$. In some embodiments, R is NH2, acetylation, stearic acid, palmitic acid, myristic acid, lauric acid, a C1-C8 hydrocarbon, a C1-C8 fatty acid, or null). In some embodiments, $X_1$ is M, G, beta alanine, norleucine, norvaline, or null). In some embodiments, $X_2$ is W, N-methyl W, R, Y, F, citrulline, or K). In some embodiments, $X_3$ is P, W, N-methyl-W, N-ethyl-W, N-methyl A, N-ethyl A, L, Pip, Aib, Y, or F). In some embodiments, $X_4$ is E, Q, N, or D). In some embodiments, $X_5$ is S, alpha methyl S, K, D, Orn, T, or E). In some embodiments, $X_6$ is I, Chg, H, or L). In some embodiments, $X_7$ is L or I). In some embodiments, $X_8$ is D, N, E, or Q). In some embodiments, $X_9$ is D, E, K, Q, or Orn). In some embodiments, $X_{10}$ is H or methyl-H). In some embodiments, $X_{11}$ is V, alpha methyl V, Chg, L I, or norvaline). In some embodiments, $X_{12}$ is Q, Aib, S, R, or N). In some embodiments, $X_{13}$ is R, K, citrulline, Orn, D, or E). In some embodiments, $X_{14}$ is V, I, L, or norvaline). In some embodiments, $X_{15}$ is W, Y, or F). In some embodiments, $X_{16}$ is R, G, or null. In some embodiments, R is NH2, acetylation, stearic acid, palmitic acid, myristic acid, lauric acid, a C1-C8 hydrocarbon, a C1-C8 fatty acid, or null; $X_1$ is M, G, beta alanine, norleucine, norvaline, or null; $X_2$ is W, N-methyl W, R, Y, F, citrulline, or K; $X_3$ is P, W, N-methyl-W, N-ethyl-W, N-methyl A, N-ethyl A, L, Pip, Aib, Y, or F; $X_4$ is E, Q, N, or D; $X_5$ is S, alpha methyl S, K, D, Orn, T, or E; $X_6$ is I, Chg, H, or L; $X_7$ is L or I; $X_8$ is D, N, E, or Q; $X_9$ is D, E, K, Q, or Orn; $X_{10}$ is H or methyl-H; $X_{11}$ is V, alpha methyl V, Chg, L I, or norvaline; $X_{12}$ is Q, Aib, S, R, or N; $X_{13}$ is R, K, citrulline, Orn, D, or E; $X_{14}$ is V, I, L, or norvaline; $X_{15}$ is W, Y, or F; and $X_{16}$ is R, G, or null.

In some cases, polar or charged groups can be removed from a peptide to increase affinity or permeability. For example, leucine or isoleucine can often be replaced with cyclohexylglycine.

In some embodiments, the peptide can be from 3 to 80 amino acids in length. In some embodiments, the peptide is at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, or at least 81 amino acid residues in length.

In some embodiments, the peptide is less than 4, less than 5, less than 6, less than 7, less than 8, less than 9, less than 10, less than 11, less than 12, less than 13, less than 14, less than 15, less than 16, less than 17, less than 18, less than 19, less than 20, less than 21, less than 22, less than 23, less than 24, less than 25, less than 26, less than 27, less than 28, less than 29, less than 30, less than 31, less than 32, less than 33, less than 34, less than 35, less than 36, less than 37, less than 38, less than 39, less than 40, less than 41, less than 42, less than 43, less than 44, less than 45, less than 46, less than 47, less than 48, less than 49, less than 50, less than 51, less than 52, less than 53, less than 54, less than 55, less than 56, less than 57, less than 58, less than 59, less than 60, less than 61, less than 62, less than 63, less than 64, less than 65, less than 66, less than 67, less than 68, less than 69, less than 70, less than 71, less than 72, less than 73, less than 74, less than 75, less than 76, less than 77, less than 78, less than 79, less than 80, or less than 81 amino acid residues in length.

In some embodiments, peptides can show homology with TCF4. In some embodiments, peptides show from about 10% to about 100% homology with TCF4. In some embodiments, peptides show about 10%, about 20%, about 30%, about 40%, about 50%, about 60%, about 70%, about 80%, about 90%, or about 100% homology with TCF4.

In some embodiments, peptides can show homology with axin. In some embodiments, peptides show from about 10% to about 100% homology with axin. In some embodiments, peptides show about 10%, about 20%, about 30%, about 40%, about 50%, about 60%, about 70%, about 80%, about 90%, or about 100% with homology axin.

a. Peptide Synthesis Methods

The peptides described herein can be produced by synthetic methods.

For example, Solid-Phase Peptide Synthesis (SPPS) allows the rapid assembly of a peptide chain through successive reactions of amino acid derivatives on an insoluble porous support.

The solid support often includes small, polymeric resin beads functionalized with reactive groups (such as amine or hydroxyl groups) that link to the nascent peptide chain. Since the peptide remains covalently attached to the support throughout the synthesis, excess reagents and side products can be removed by washing and filtration.

Each amino acid to be coupled to the peptide chain N-terminus can be protected on its N-terminus and side chain using appropriate protecting groups such as Boc (acid-labile) or Fmoc (base-labile), depending on the side chain and the protection strategy used (see below).

The general SPPS procedure is usually one of repeated cycles of alternate N-terminal deprotection and coupling reactions. The resin can be washed between each step. First, an amino acid is often coupled to the resin. Subsequently, the amine is usually deprotected, and then coupled with the free acid of the second amino acid. This cycle can repeat until the desired sequence has been synthesized. SPPS cycles may also include capping steps that can block the ends of unreacted amino acids from reacting. At the end of the synthesis, the crude peptide can be cleaved from the solid support. This step can often include simultaneously removing all protecting groups using a strong acid like trifluoroacetic acid or a nucleophile. The crude peptide can be precipitated from a non-polar solvent like diethyl ether in order to remove organic soluble by products. The crude peptide can be purified using reversed-phase HPLC. Byproducts may be removed using continuous chromatography processes such as MCSGP to maximize the yield without sacrificing on purity levels.

b. Methods for Cyclizing Peptides

The peptides described herein can be cyclic peptides. Cyclic peptides are often stable peptide analogues with strong conformational stability and biostability. Cyclic peptides can offer several advantages in certain circumstances. For example, cyclic peptides often metabolize slower due to their higher resistance toward proteases than non-cyclic counterparts; on the other hand, they have longer-acting depot effect than their corresponding linear counterparts. They can be used to mimic the structure of biologically active peptides (e.g., peptide hormones) and are able to bind drug targets in vivo.

1) Disulfide Bridge Cys-Cys Thiol Oxidation

The peptides described herein can by cyclized using a disulfide bridge. Peptide disulfide bridge can link two thiol (SH) groups from the side chain of cysteines or cysteine analogues. Undesired linkage can be prevented by using appropriate protecting group chemistry to effect either specific intra- or intermolecular oxidation. In general, a disulfide bridge can be formed as follows: intermolecular (two peptide molecules are linked via the disulfide bridge), resulting in either: homodimers (two identical peptides) or heterodimers (two different peptides), or intramolecular (cyclization within one peptide molecule).

2) Amide Bond formation, Lactam Formation

Cyclic peptides can also be synthesized by linking the amino (N) terminus of the peptide to the carboxyl (C) terminus via an amide bond. The amino side chains of Lys and Orn and the carboxyl side chains of Asp and Glu can also be used to construct cyclic peptides via an amide bond. Depending on functional groups of a peptide, cyclic peptide synthesis often uses one of four different methods: head-to-tail between N-terminus and C-terminus; head-to-side chain between N-terminus and an internal COOH (e.g. the β-COOH-group of Asp or γ-COOH-group of Glu); side chain-to-tail between internal NH2s and C-terminus (e.g. the ε-NH2-group of Lys); and side-chain-to-side-chain between an internal NH2 and an internal COOH (e.g. the ε-NH2-group of Lys with either the β-COOH-group of Asp or γ-COOH-group of Glu).

3) Stapled Peptide Synthesis

The peptides described herein can be cyclized using stapled peptide synthesis. Peptide stapling is typically achieved by incorporating α, α disubstituted non-natural amino acids bearing terminal olefin tethers of varying length. Subsequent olefin metathesis creates carbon-carbon bond tethers between amino acid side chains to cyclize the peptide. Alternatively, stapled peptides can be generated using Fmoc solid-phase synthesis chemistry as is generally known in the art. Stapled peptides have a chemically-locked conformational structure that can mimic the molecular structures that are typically found at the interface of protein-protein interactions. When locked into this stable configuration, constraint peptides are able to penetrate cells and can exert their effect on intracellular protein targets. The large surface area of the peptides gives them advantages over small molecules in their ability to disrupt specific signaling pathways by inhibiting targeted protein-protein interactions.

4) Click Chemistry for Peptide Cyclization

The peptides described herein can also by cyclized using click chemistry. Clickable functional groups can be incorporated into peptides at time of synthesis using different combinations of protected amino acids modified with an alkyne group, followed by click reaction with an azido-acid. The resulting peptides are detached off the resin to give triazole-containing peptides. These functional groups can also be introduced via post synthesis modification to produce structurally constrained peptides.

c. Methods to Increase Peptide Stability

The peptides described herein can have modifications to increase stability. It has been generally shown that N-methyl modifications can increase function and stability of peptide ligands (Fiacco et al., Chembiochem 2008, 9(14): 2200; Fiacco et al., Chembiochem 2016, 17(17): 1643, each of which is incorporated by reference herein for such disclosure). In some embodiments described herein, peptides are modified with one or more N-methyl analogues to natural amino acids. Incorporation of one or more N-methyl amino acids can increase proteolytic resistance form 10-fold to 10000-fold over resistance of peptide consisting of natural residues. In some embodiments, the proteolytic resistance of peptides containing one or more N-methyl amino acids is at least 10-fold, at least 20-fold, at least 30-fold, at least 40-fold, at least 50-fold, at least 60-fold, at least 70-fold, at least 80-fold, at least 90-fold, at least 100-fold, at least 200-fold, at least 400-fold, at least 500-fold, at least 600-fold, at least 700-fold, at least 800-fold, at least 900-fold, at least 1000-fold, at least 2000-fold, at least 3000-fold, at least 4000-fold, at least 5000-fold, at least 6000-fold, at least 7000-fold, at least 8000-fold, at least 9000-fold, at least 10,000-fold over resistance of the peptide consisting of natural residues.

III. CHARACTERIZATION ASSAYS

A. Surface Plasmon Resonance

Surface plasmon resonance (SPR) is an optical phenomenon that enables detection of unlabeled interactants in real time. The SPR-based biosensors, such as the Biacore® T100 system (Biacore®, Uppsala, Sweden), can be used in determination of active concentration as well as characterization of molecular interactions in terms of both affinity and chemical kinetics. The maximum binding capacity of the surface (response at saturation) can be calculated using the Biacore® system (GE) instructions. The binding levels are determined over a range of analyte concentrations of at least from 20% to 80% saturation of the surface. On rates, off rates, and KD calculated using Biacore® Insight Evaluation SoOftware (GE). The concentration at saturation of 50% is calculated from these series of dilutions and presented as $K_D50$. Binding kinetics and thermodynamics of selected peptides from libraries described herein are displayed in Table 5. Exemplary methodology is described in Example 11.

In some instances, peptides described herein comprise a binding affinity ($K_D$) greater than about 30 uM. In some instances, peptides described herein comprise a binding affinity ($K_D$) less than about 30 uM, less than about 10 uM, less than about 5 uM, less than about 1 uM, less than about 500nm, less than about 400 nM. less than about 300 nM, less than about 200 nM, less than about 150 nM, less than about 100 nM, less than about 50 nM, or less than about 10 nM.

B. Fluorescence Polarization (FP)

Fluorescence polarization (FP) is another method used to analyze protein-ligand interactions. This methodology measures the change in fluorescence light emitted by a labelled compound free vs. conjugated to another compound in solution. Upon binding of the fluorescent molecule to a complex, polarization increases because of limited rotation of the fluorescent tracer. Competitive FP is often utilized in drug screens as it is formatted for high throughput screens in a plate format. This immunoassay is performed by introducing a non-conjugated drug to compete for binding to the labelled competitor-ligand complex, leading to a reduction in polarization. TCF4 protein is utilized for the competitive assay as (1) this protein influences the full activation of the Wnt pathway and (2) shares homology with the β-catenin inhibitors. Exemplary methodology is described in Example 13. Data were analyzed and plotted in Microsoft Excel (Microsoft, Redmond, WA.). The resulting KD50 was calculated as shown in Table 5.

C. Wnt-Dependent Luciferase Reporter Assay

The luciferase reporter assay is commonly used as a tool to study gene expression at the transcriptional level. Peptides from libraries described herein were characterized for ability to suppress transcription in cells with luciferase expression controlled by a Wnt-responsive promoter. Peptides were added to cells transfected with luciferase gene downstream of a Wnt-responsive promoter. Cells were stimulated with Wnt3a protein and incubated with peptides from libraries described herein. Luminescence was recorded to determine the peptides with the highest β-catenin-inhibiting activity. EC50 values were calculated based on the inhibition of luminescence and expressed as concentration (uM) in Table 5.

D. Cell Proliferation Assay

Peptides inhibiting β-catenin cause decreased cell viability in a colon cancer cell line (SW480) and endometriosis lesions excised from a disease animal model. Peptides from libraries described herein are characterized in their effect on cell viability, as measured using a luminescent cell viability assay (Cell Titer-Glo®, Promega, Madison, WI.) and expressed as $IC_{50}$ in Table 5.

In some instances, peptides described herein comprise an $IC_{50}$ greater than 30 uM. In some instances, peptides described herein comprise an $IC_{50}$ less than about 30 uM, less than about 25 uM, less than about 22.5 uM, less than about 20 uM, less than about 15 uM, less than about 10 uM, less than about 7.5 uM, less than about 5 uM, or less than about 1 uM.

IV. ADMINISTRATION

A. Methods of Dosing and Treatment Regimens

In one embodiment, the inhibitor compositions described herein are used in the preparation of medicaments for the treatment of diseases, conditions, or symptoms in a mammal that would benefit from administration of a β-catenin-inhibitor. Methods for treating any of the diseases or conditions described herein in a mammal in need of such treatment involve administration of pharmaceutical compositions that include at least one inhibitor described herein in therapeutically effective amounts to said mammal.

Diseases, conditions, or symptoms that may benefit from treatment with compositions as described herein include, but are not limited to, endometriosis, endometriosis lesions, endometriomas, superficial endometriotic implants, deeply infiltrating endometriosis, chronic pain, central sensitization, myofascial pain, adnexal masses, infertility, dysmenorrhea, genetic predisposition, nonmenstrual pelvic-abdominal pain, dyspareunia, bowel symptoms (diarrhea, cramping, constipation), defecation pain (dyschezia), ovarian mass or tumor, painful bladder symptoms, and dysuria.

In certain embodiments, the compositions containing the inhibitor(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patients health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the inhibitors described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising an inhibitor described herein in order to prevent a return of the symptoms of the disease or condition.

In certain embodiments, wherein the patient's condition does not improve, upon the doctor's discretion, the inhibitors are administered chronically, that is, for an extended period of time, including throughout the duration of the patient's life in order to ameliorate or otherwise control or limit the symptoms of the patient's disease or condition.

In certain embodiments, wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular inhibitor, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, doses employed for adult human treatment are typically in the range of from about 0.01 mg to about 5000 mg per day. In some aspects, doses employed for adult human treatment are from about 0.01 mg to about 1000 mg per day. In some embodiments, the desired dose is conveniently presented in a single dose or in divided doses administered simultaneously or at appropriate intervals, for example as two, three, four or more sub-doses per day. In other embodiments, the composition described herein is formulated for extended release over a period of hours, days or months. In some embodiments, the composition is formulated for delivery over 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 18 hours, 19 hours, 20 hours, 21 hours, 22 hours, 23 hours, 24 hours, 1 day, 2 days, 3 days, 4 days, 5 days, 6 days, 7 days, 1 week, 2 weeks, 3 weeks, 4 weeks, 1 month, 2 months, 3 months, 4 months, 5 months, 6 months, 7 months, 8 months, 9 months, 10 months, 11 months, 12 months, 1 year, 2 years, 3 years, 4 years, 5 years, 6 years, 7 years, 8 years, 9 years, 10 years, 11 years, or 12 years.

In some embodiments, the daily dosages appropriate for the inhibitor described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the inhibitor used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the inhibitors described herein lies within a range of circulating concentrations that include the ED50 with minimal toxicity. In certain embodiments, the daily dosage range and/or the unit dosage amount varies within this range depending upon the dosage form employed and the route of administration utilized.

In any of the aforementioned aspects are further embodiments in which the effective amount of the inhibitor described herein is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the inhibitor, including further embodiments in which (i) the inhibitor is administered once a day; or (ii) the inhibitor is administered to the mammal multiple times over the span of one day. In additional aspects are embodiments wherein the inhibitor is administered continuously over a period of time.

In any of the aforementioned aspects are further embodiments comprising multiple administrations of the effective amount of the inhibitor, including further embodiments in which (i) the inhibitor is administered continuously or intermittently: as in a single dose; (ii) the time between multiple administrations is every 6 hours; (iii) the inhibitor is administered to the mammal every 8 hours; (iv) the inhibitor is administered to the mammal every 12 hours; (v) the inhibitor is administered to the mammal every 24 hours.

In any of the aforementioned aspects are further embodiments comprising the inhibitor incorporated in to a delivery vehicle to provide sustained delivery of the inhibitor. In some embodiments, the delivery is sustained for about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 18 hours, 19 hours, 20 hours, 21 hours, 22 hours, 23 hours, 24 hours, 1 day, 2 days, 3 days, 4 days, 5 days, 6 days, 7 days, 1 week, 2 weeks, 3 weeks, 4 weeks, 1 month, 2 months, 3 months, 4 months, 5 months, 6 months, 7 months, 8 months, 9 months, 10 months, 11 months, 12 months, 1 year, 2 years, 3 years, 4 years, 5 years, 6 years, 7 years, 8 years, 9 years, 10 years, 11 years, or 12 years. In some embodiments, the inhibitor is incorporated in to a transdermal patch, a tape, a suppository, a vaginal suppository, vaginal tampon, vaginal ring, vaginal strip, vaginal capsule, vaginal tablet, vaginal pessary, vaginal cup, vaginal sponge, or an intrauterine device.

In further or alternative embodiments, the method comprises a drug holiday, wherein the administration of the inhibitor is temporarily suspended or the dose of the inhibitor being administered is temporarily reduced; at the end of the drug holiday, dosing of the inhibitor is resumed. In one embodiment, the length of the drug holiday varies from 2 days to 1 year.

In certain instances, it is appropriate to administer at least one inhibitor described herein in combination with one or more other therapeutic agents. Exemplary additional therapeutic agents may include, but are not limited to, hormonal therapeutic agents, including birth control, combination birth control, selective progesterone receptor antagonists, selective progesterone receptor agonists, gonadotropin-releasing hormone receptor antagonists, gonadotropin-releasing hormone receptor agonists, antiretroviral agents, antineoplastic agents, anti-inflammatories, nonsteroidal anti-inflammatories, or any combination thereof.

In one embodiment, the therapeutic effectiveness of one of the inhibitors described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the inhibitors described herein with another agent (which also includes a therapeutic regimen) that also has therapeutic benefit.

In one specific embodiment, an inhibitor described herein is co-administered with a second therapeutic agent. In some cases, the inhibitor described herein and the second therapeutic agent modulate different aspects of the disease, disorder or condition being treated, thereby providing a greater overall benefit than administration of either therapeutic agent alone. In any case, regardless of the disease, disorder or condition being treated, the overall benefit experienced by the patient may be additive of the two therapeutic agents or the patient may experience a synergistic benefit.

In certain embodiments, different therapeutically-effective dosages of the inhibitors disclosed herein will be utilized in formulating pharmaceutical composition and/or in treatment regimens when the inhibitors disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of an inhibitor described herein is initiated prior to, during, or after treatment with a second agent described herein, and continues until any time during treatment with the second agent or after termination of treatment with the second agent. It also includes treatments in which an inhibitor described herein and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought can be modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered inhibitors vary depending on the type of co-drug employed, on the specific drug employed, on the disease or condition being treated and so forth. In additional embodiments, when co-administered with one or more other therapeutic agents, the inhibitor provided herein is administered either simultaneously with the one or more other therapeutic agents, or sequentially.

In combination therapies, the multiple therapeutic agents (one of which is one of the inhibitors described herein) are administered in any order or even simultaneously. If administration is simultaneous, the multiple therapeutic agents are, by way of example only, provided in a single, unified form, or in multiple forms (e.g., as a single pill or as two separate pills).

The inhibitors described herein, as well as combination therapies, are administered before, during or after the occurrence of a disease or condition, and the timing of administering the composition containing an inhibitor varies. Thus, in one embodiment, the inhibitors described herein are used as a prophylactic and are administered continuously to subjects with a propensity to develop conditions or diseases in order to prevent the occurrence of the disease or condition. In another embodiment, the inhibitors and compositions are administered to a subject during or as soon as possible after the onset of the symptoms. In specific embodiments, an inhibitor described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, an inhibitor described herein or a formulation containing the inhibitor is administered for at least 2 weeks, about 1 month to about 5 years.

B. Pharmaceutical Composition

In some embodiments, the inhibitors described herein are formulated into pharmaceutical compositions. Pharmaceutical compositions are formulated in a conventional manner using one or more pharmaceutically acceptable inactive ingredients that facilitate processing of the active inhibitors into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

In some embodiments, the inhibitors described herein are administered either alone or in combination with pharmaceutically acceptable carriers, excipients or diluents, in a pharmaceutical composition. Administration of the inhibitors and compositions described herein can be affected by any method that enables delivery of the inhibitors to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal, and intrauterine) administration, although the most suitable route may depend upon for example the condition and disorder of the recipient. By way of example only, inhibitors described herein can be administered locally to the area in need of treatment, by for example, local infusion during surgery, topical application such as creams or ointments, injection, catheter, implant, or inserted device. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions that can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered inhibitor moistened with an inert liquid diluent. In some embodiments, the tablets are coated or scored and are formulated so as to provide slow or controlled release of the active ingredient therein. All formulations for oral administration can be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active inhibitors may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active inhibitor doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active inhibitors which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the inhibitors to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the inhibitors may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal or vaginal compositions such as suppositories or retention enemas, e.g., containing conventional suppository bases such as cocoa butter, polyethylene glycol, or other glycerides. When inserted, the suppository base liquefies or becomes water-miscible at body temperature so as to allow the components to become in contact with the mucous membrane for a sufficient period of time to have a therapeutic effect. The weight percent of the suppository base is dependent upon the size of the bodily orifice of the human and/or the animal, the dosage composition necessary to have a therapeutic effect, and its physiochemical characteristics that allow it to remain solid at or below room temperature. In some embodiments, the suppository comprises from about 50% to greater than 99%, or about 75% to greater than 99% by weight of the suppository base. In some embodiments, the suppository comprises about 75% to about 98% by weight polyethylene glycol. In some embodiments, the suppository comprises about 2% to about 25% by weight polysorbate. The suppository base has a molecular weight in the range of about 400 to about 5000, or about 950 to about 3700 (US 2009/0311290, incorporated by reference herein for such disclosure).

In some cases, the pharmaceutical composition comprises an absorption enhances, such as sodium caprate. Some of such cases include compositions and dosage forms for use in the rectum or vagina as described herein.

Pharmaceutical compositions may be administered topically or rectally, that is, by non-systemic administration. This includes the application of an inhibitor of the present disclosure externally to the epidermis or the buccal cavity and the instillation of such an inhibitor into the rectum or vagina such that the inhibitor does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin such as solutions, lotions, shake lotions, creams, ointments, gels, foams, transdermal patches, powders, solids, sponges, tapes, vapors, pastes, tinctures, microparticles, microcapsules, nanoparticles, liposomes, or emulsions, including those suitable for delivery to the vagina or rectum. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the inhibitor and a suitable powder base such as lactose or starch. The powder composition may be presented in unit dosage form, in for example, capsules, cartridges, gelatin or blister packs from which the powder may be administered with the aid of an inhalator or insufflator.

In some embodiments, an inhibitor disclosed herein is formulated in such a manner that delivery of the inhibitor to a particular region of the gastrointestinal tract is achieved. For example, an inhibitor disclosed herein is formulated for oral delivery with bioadhesive polymers, pH-sensitive coatings, time dependent, biodegradable polymers, microflora activated systems, and the like, in order to effect delivering of the inhibitor to a particular region of the gastrointestinal tract.

In some embodiments, an inhibitor disclosed herein is formulated in such a manner that delivery of the inhibitor to a particular region of the urogenital or anorectal mucosa is achieved. For example, an inhibitor disclosed herein is formulated for intravaginal delivery with bioadhesive polymers, pH-sensitive coatings, time dependent, biodegradable polymers, microflora activated systems, and the like, in order to effect delivering of the inhibitor to a particular region of the urogenital system. In some embodiments, an inhibitor disclosed herein is formulated to provide a controlled release of the inhibitor. Controlled release refers to the release of the inhibitor described herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

Approaches to deliver the intact therapeutic inhibitor to the particular regions of the urogenital system (such as the vagina) or gastrointestinal tract (e.g. such as the colon), include:

(i) Coating with polymers: The intact molecule can be delivered to the colon without absorbing at the upper part of the intestine by coating of the drug molecule with the suitable polymers, which degrade only in the colon. In addition, coating with polymers can provide protection or controlled-release profile for vaginal formulations.

(ii) Coating with pH-sensitive polymers: Enteric, colon, and vaginal targeted delivery systems can be based on the coating of tablets or pellets, which are filled into conventional hard gelatin capsules. Most commonly used pH-dependent coating polymers are methacrylic acid copolymers, commonly known as Eudragit® S, more specifically Eudragit® L and Eudragit® S. Eudragit® L100 and S 100 are copolymers of methacrylic acid and methyl methacrylate.
(iii) Coating with biodegradable polymers;
(iv) Embedding in matrices;
(v) Embedding in biodegradable matrices and hydrogels;
(vi) Embedding in pH-sensitive matrices;
(vii) Timed release systems;
(viii) Redox-sensitive polymers;
(ix) Bioadhesive systems;
(x) Coating with microparticles;
(xi) Osmotic controlled drug delivery;

Another approach towards vaginal- and colon-targeted drug delivery or controlled-release systems includes embedding the drug in polymer matrices to trap it and release it in the vagina or colon. These matrices can be pH-sensitive or biodegradable. Matrix-Based Systems, such as multi-matrix (MMX)-based delayed-release tablets, ensure the drug release in the vagina or colon.

C. Dosage Forms

The compositions and methods described herein can include delivering the therapeutic agents via a variety of dosage forms and devices, including those described below. Many of the dosage forms described below provide for several advantages. These can include local delivery of the therapeutic inhibitors. Local delivery can reduce the side effects that can sometimes be associated with systemic delivery and off-target effects. In some cases, the dosage forms and devices described herein can increase patient compliance including, for example, by providing long-term or continuous delivery of the inhibitors described herein. In some cases, these dosage forms and devices can also increase tolerability and safety.

1. Intravaginal Ring

Peptides and compositions described herein can be incorporated in an intravaginal ring for delivery. Delivery of therapeutic via intravaginal ring (IVR) allows for local delivery, increasing safety and tolerability of the therapeutic substance. IVRs additionally can offer multiple advantages: bypass gastrointestinal absorption and hepatic/renal first-pass metabolism, lower effective dosage, continuous delivery and/or controlled release profiles, extended time between doses, reduced side effects, low serum drug concentrations, patient self-administration, and improved patient satisfaction. IVRs can successfully deliver drugs, including hydrophilic and macromolecular agents, to organs affected by EMS, including deep infiltrating EMS (DIE). The biodistribution of the vaginal ring delivery system is via tissue absorption rather than serum and can reach all organs that are affected by EMS in the peritoneal cavity.

Vaginal rings usually consist of an inert elastomer ring coated by another layer of elastomer containing the drug to be delivered. The rings can be easily inserted, left in place for the desired period of time, then removed by the user. The ring may be solid or hollow containing the therapeutic component, or it may be a porous material releasing the drug therefrom. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered. In some cases, the IVR can comprise silicone, compressed tablets, or lyophilized gel.

Pessaries, cups, strips, tablets, and suppositories are other examples of drug delivery systems which can be used in the present disclosure. These systems have been used for delivery of vaginal contraceptives, and have been described extensively in the literature.

Another example of a delivery system is the vaginal sponge and foams. The desired pharmaceutical agent can be incorporated into a silicone matrix which is coated onto a cylindrical drug-free polyurethane vaginal sponge, as described in the literature.

In some embodiments, the IVR comprises peptides or compositions as described herein, formulated as a suppository, solution, lotion, shake lotion, cream, ointment, gel, foam, transdermal patch, powder, solid, sponge, tape, paste, tincture, emulsion, microparticle, microcapsule, nanoparticle, liposome or a capsule containing microparticles, microcapsules, nanoparticles, or liposomes. IVRs have further been modified to comprise a variety of delivery vehicles, such as silicone inserts, compressed tablets, or lyophilized gel, to optimize the release profile of hydrophilic or high molecular weight inhibitors such as peptides, proteins, or antibodies (Morrow, et. al., *Eur J Pharm Biopharm*, 2011 January; 77(1): 3-10, incorporated by reference herein for such disclosure). IVRs can also comprise one or more absorption enhancers, such as sodium caprate.

In some embodiments, IVRs described herein are formulated to comprise from about 0.01 mg to about 5000 mg inhibitor. In some embodiments, the IVR can contain about 0.01 mg, about 0.05 mg, about 0.1 mg, about 0.5 mg, about 1 mg, about 5 mg, about 10 mg, about 20 mg, about 40 mg, about 60 mg, about 80 mg, about 100 mg, about 150 mg, about 200 mg, about 400 mg, about 600 mg, about 800 mg, about 1000 mg, about 1200 mg, about 1400 mg, about 1600 mg, about 1800 mg, about 2000 mg, about 2500 mg, about 3000 mg, about 3500 mg, about 4000 mg, about 4500 mg, or about 5000 mg inhibitor.

In some embodiments, IVRs described herein are formulated to deliver from about 0.01 mg to about 1000 mg inhibitor/day. In some embodiments, the IVR is formulated to deliver about 0.01 mg, about 0.05 mg, about 0.1 mg, about 0.5 mg, about 1 mg, about 5 mg, about 10 mg, about 20 mg, about 40 mg, about 60 mg, about 80 mg, about 100 mg, about 150 mg, about 200 mg, about 400 mg, about 600 mg, about 800 mg, or about 1000 mg inhibitor/day.

2. Vaginal Tampon

Peptides and compositions described herein can be incorporated in a tampon device for delivery. A tampon device typically comprises a vaginal tampon having a proximal end and a distal end. A cup-shaped porous foam portion at the distal end fits around the cervix and contains a peptide or composition as described herein for delivery. The device may also include a nonabsorbing axial tube having a distal opening and extending through the porous foam cup into the tampon for conducting blood flow to the absorbent material. Optionally, a retrieval string or tape connected to the tampon device is also included. The absorbent vaginal tampon contains peptides or compositions as described herein or may be coated with the peptides or compositions as described herein and be used as a medicated tampon for delivery.

3. Pessary/Suppository/Compressed Tablets

Peptides and compositions described herein may be incorporated in to a solid for local delivery. A solid may be in the form of a pessary or vaginal or rectal suppository. The solid dosage form may melt when it reaches body temperature. Alternatively, the solid may retain its structure and release incorporated compositions as described herein. The solid may be a pessary designed to provide support within the vagina. A vaginal sponge may be embedded with a composition described herein for intravaginal delivery.

4. Topical Medication

Peptides and compositions described herein can be incorporated in a topical formulation for delivery. A topical medication is applied to a body surface, such as the skin or a mucous membrane. In some instances, the body surface includes, without limitation, epithelial tissue, mucosal tissue, peritoneum, perimetrium, and endometrium. Inhibitor is absorbed through the body surface to achieve a local or systemic effect. Topical medications are optionally formulated in the following classes: a topical solution; a lotion; a shake lotion; a cream; an ointment; a gel; a foam; a transdermal patch; a powder; a solid; sponge; tape; vapor; paste; or tincture. A topical solution may be administered as a rinse, spray, or drop, typically with low viscosity with water or alcohol in the base. A lotion can be thicker and more emollient than a solution. It is usually an oil mixed in water and may have less alcohol than a solution. A shake lotion is a mixture that separates into two or three parts with time. It may be an oil mixed with a water-based solution that needs to be shaken into suspension prior to use. A cream is an emulsion of oil and water in approximately equal proportions. An ointment is a homogeneous, viscous, semi-solid preparation, most commonly a greasy, thick oil (oil 80%-water 20%) with a high viscosity. An ointment may comprise a hydrocarbon base, an absorption base, a water-soluble base, an emulsifying base, or a vegetable oil, or any combination thereof. An ointment is formulated in a base which may include, but is not limited to, a hydrocarbon base, such as hard paraffin, soft paraffin, microcrystalline wax, or ceresine; absorption bases, such as wool fat or beeswax; water-soluble bases, such as macrogols 200, 300, or 400; emulsifying bases, such as emulsifying wax or cetrimide; or vegetable oils, such as olive oil, coconut oil, sesame oil, almond oil, or peanut oil.

A gel is a semisolid emulsion. Non-limiting examples of useful emulsifiers include acrylic acid polymers (such as carbomer brand thickeners e.g. Carbomer 934P, manufactured by Voveon, Inc.), polyoxyethylene-10-stearyl ether, polyoxyethylene-20-stearyl ether, cetostearyl alcohol, cetyl alcohol, cholesterol, diglycol stearate, glyceryl monostearate, glyceryl stearate, polygeyceryl-3-oleate, hydroxypropyl cellulose, hydroxypropylmethyl cellulose, lanolin, polyoxyethylene lauryl ether, methyl cellulose, polyoxyethylene stearate, polysorbate, propylene glycol monostearate, sorbitan esters, stearic acid or mixtures of two or more thereof.

The amount of emulsifier in the topical formulation can range from about 1 to about 40 weight percent, and in some embodiments from about 5 to about 30 weight percent, on a basis of total weight of the topical formulation.

The gel formulations as described herein may include one or more gelling agents. Non-limiting examples of useful gelling agents include carboxylic acid polymers including acrylic acid polymers crosslinked with cross links such as allyl ethers of sucrose (e.g. carbomer brand thickeners), cetostearyl alcohol, hydroxymethyl cellulose, polyoxyethylene-polyoxypropylene copolymer, sodium carboxymethylcellulose, polyvinyl pyrrolidone, or mixtures of two or more thereof The amount of gelling agent in the topical gel formulation can range from about 0.1 to about 10 weight percent, and in some embodiments from about 0.1 to about 1 weight percent, on a basis of total weight of the topical formulation.

The gel formulations described herein can further comprise one or more alkalinizers, for example sodium hydroxide, in amount of less than about 2 weight percent as activators of gelling.

The formulations can contain one or more additional excipients well known in the art, for example water and a thickening agent such as colloidal silicon dioxide.

A thermoreversible gel is a liquid formulation that turns to gel once inserted in to the rectum or vagina. A thermoreversible gel allows for easier administration and positioning than conventional suppositories or pessaries and can prevent dosage form leakage. It is formulated as a polymer solution consisting of thermoreversible polymers (e.g., poloxamers, in combination with mucoadhesive polymers that enable gel attachment to the mucosa). In situ thermoreversible liquid-gel formulations, also called thermoreversible "liquid suppositories", are liquid at low temperatures (<10C) and turn to gel at body temperature.

Active agent can be incorporated in to a surgical tape for an occlusive dressing. Medication can be applied as an ointment or gel, to reach a mucous membrane through vaporization. A paste combines oil, water, and a powder. A tincture typically contains a high percentage of alcohol for application to the skin.

5. Transdermal Patch and Films

Peptides and compositions described herein can be incorporated in a transdermal patch delivery. A transdermal patch provides a controlled release of medication either through a porous membrane covering a reservoir of medication or through body heat melting thin layers of medication embedded in the patch adhesive.

Compositions described herein may be incorporated in a film for delivery. Films are thin, small polymeric formulations that can be easily inserted into the vaginal cavity without an applicator and without causing discomfort. Vaginal films are easier to apply than other types of vaginal formulations such as pessaries, foams and gels (Rohan L C et al., AAPS Journal 2009; 11:78-87, incorporated by reference herein for such disclosure).

6. Intrauterine Device

Peptides and compositions described herein can be incorporated in an intrauterine device (IUD), a small often T-shaped device that is inserted into the uterus for delivery. IUDs typically contain copper, progestogen, or levonorgestrel. Compositions as described herein are incorporated in to an IUD device to be released slowly over time.

7. Systemic Delivery (Injection)

Peptides and compositions as described herein can be formulated for systemic delivery.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of a peptide described herein in water soluble form. Suspensions of peptides described herein can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility and/or reduce the aggregation of such peptides described herein to allow for the preparation of highly concentrated solutions. Alternatively, the peptides described herein can be lyophilized or in powder form for re-constitution with a suitable vehicle, e.g., sterile pyrogen-free water, before use. In some embodiments, a purified peptide is administered intravenously.

8. Pills

Peptides and compositions described herein can be formulated for oral delivery. Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered inhibitor moistened with an inert liquid diluent. In some embodiments, the tablets are coated or scored and are formulated so as to provide slow or controlled release of the active ingredient therein. Formulations for oral administration may be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active inhibitors may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active inhibitor doses.

Additional pharmaceutical approaches to targeted delivery of therapeutics to particular regions of the gastrointestinal tract are known. Chourasia M K, Jain S K, Pharmaceutical approaches to colon targeted drug delivery systems., J Pharm Sci. 2003 January-April; 6(1):33-66. Patel M, Shah T, Amin A. Therapeutic opportunities in colon-specific drug-delivery systems Crit Rev Ther Drug Carrier Syst. 2007; 24(2):147-202. Kumar P, Mishra B. Colon targeted drug delivery systems—an overview. Curr Drug Deliv. 2008 July; 5(3):186-98. Van den Mooter G. Colon drug delivery. Expert Opin Drug Deliv. 2006 January; 3(1):111-25. Seth Amidon, Jack E. Brown, and Vivek S. Dave, Colon-Targeted Oral Drug Delivery Systems: Design Trends and Approaches, AAPS Pharm Sci Tech. 2015 August; 16(4): 731-741. Each of these references is incorporated by reference herein for such disclosure.

It should be understood that in addition to the ingredients particularly mentioned above, the inhibitors and compositions described herein may include other agents conventional in the art having regard to the type of formulation in question. For example, agents suitable for oral administration may include flavoring agents.

D. Formulation

Peptides and compositions described herein may contain additional excipients to improve performance of the therapeutic. Compositions may contain absorption enhancers, or permeation enhancers, to improve absorption across the epidermal or mucosal surface and membrane permeation. Enhancers formulated in compositions described herein may include, but are not limited to, sulphoxides, such as dimethyl sulphoxides (DMSO); laurocapran (1-dodecylazacycloheptan-2-one); pyrrolidones, such as n-methyl-2-pyrrolidone; terpenes and terpenoids; essential oils; oxazolidinones, such as 4-decycloxazolidin-2-one; urea; cyclopentadecalactone; sodium N-[8-(2-hydroxylbenzoyl)amino] caprylate (SNAC); 8-(N-2-hydroxy-5-chloro-benzoyl)-amino-caprylic acid (5-CNAC); medium chain fatty acids, salts, and derivatives; sodium caprate; sodium caprylate; protease inhibitor and omega-3 fatty acid; liquid mixed-micelle spray; lipid polymer micelle; alkylglycosides; chitosan; dodecyl-2-N,N-dimethylamino propionate (DDAIP); cell-membrane-lipid components; nanoparticles; liposomes, ligands; and lipophilic modifications.

Peptides and compositions described herein may be formulated as a solution, a lotion, a shake lotion, a cream, an ointment, a gel, a foam, a mucoadhesive composition, an emulsion, liposomes, a coating, a core, a matrix, a lyophilisate.

E. Conditions Treated

Methods described herein may be used to treat or prevent a tissue-infiltrating condition. As used herein, a tissue-infiltrating condition comprises any disease, disorder, malignancy, metastasis, mutation, condition, etc. wherein cells migrate, infiltrate, metastasize, or in some way grow in a location or to an extent that is in some way pathogenic or otherwise detrimental to the subject in which the cells grow. In some embodiments, the tissue-infiltrating condition comprises endometriosis. In further embodiments, the tissue-infiltrating condition comprises a cancer. The cancer can comprise colorectal carcinoma, squamous cell carcinoma, head and neck cancer, pancreatic cancer, breast cancer, myeloid leukemia, basal cell carcinoma, synovial sarcoma, non-small cell lung cancer, a solid tumor, or prostate cancer. In additional embodiments, the tissue-infiltrating condition comprises a fibrosis. The fibrosis can comprise Hepatitis A, Hepatitis B, Hepatitis C, adenomyosis, pulmonary fibrosis, cystic fibrosis, idiopathic pulmonary fibrosis, radiation-induced lung injury, liver cirrhosis, atrial fibrosis, endomyocardial fibrosis, old myocardial infarction, glial scar, arterial stiffness, arthrofibrosis, Chron's disease, Dupuytren's contracture, keloid, mediastinal fibrosis, myelofibrosis, Peyronie's disease, nephrogenic systemic fibrosis, progressive massive fibrosis, retroperitoneal fibrosis, scleroderma/systemic sclerosis, or adhesive capsulitis.

F. Co-Administration

Peptides and compositions described herein may be co-administered with other therapeutic agents. In embodiments described herein, a circular peptide composition may be administered with a medication to treat osteoporosis including, but not limited to, alendronate, ibandronate, risedronate, zoledronic acid, denosumab, calcitonin, estrogen, raloxifene, bazodoxifene, teriparatide, abaloparatide, or any combination thereof.

V. EXEMPLARY EMBODIMENTS

1. A peptide comprising an amino acid sequence having the formula $X_1$—$X_2$—$X_3$—$X_4$—$X_5$—$X_6$—$X_7$—$X_8$—$X_9$—$X_{10}$—$X_{11}$—$X_{12}$—$X_{13}$—$X_{14}$—$X_{15}$—$X_{16}$, wherein: $X_1$ is M or null; $X_2$ is S, I, G, T, A, L, or null; $X_3$ is R, K or null; $X_4$ is a positively-charged amino acid, citrulline, Orn, D, E, 8-aminooctanoic acid, or an amino carboxylic acid with between 4 and 12 carbons; $X_5$ is M, Norleucine, Orn, D, E, K, H, R, K, 8-aminooctanoic acid, an amino carboxylic acid with between 4 and 12 carbons or null; $X_6$ is W, Y, F, or N-methyl A; $X_7$ is F, I, L, Chg, Cha, or Tle; $X_8$ is L, I, or A; $X_9$ is L, I, or A; $X_{10}$ is C, S, A, Abu, C(me), or S(Bzl); $X_{11}$ is F, H, A, K, E, Chg, Cng, or Orn; $X_{12}$ is W, Y, A, or F; and $X_{13}$ is G, GABA, or null.

2. A peptide comprising an amino acid sequence having the formula R—$X_1$—$X_2$—$X_3$—$X_4$—$X_5$—$X_6$—$X_7$—$X_8$—$X_9$—$X_{10}$—$X_{11}$—$X_{12}$—$X_{13}$—$X_{14}$—$X_{15}$—$X_{16}$, wherein: R is NH$_2$, acetylation, stearic acid, palmitic acid, myristic acid, lauric acid, a $C_1$-$C_8$ hydrocarbon, a $C_1$-$C_8$ fatty acid, or null; $X_1$ is M, G, beta alanine, norleucine, norvaline, or null; $X_2$ is W, N-methyl W, R, Y, F, citrulline, or K; $X_3$ is P, W, N-methyl-W, N-ethyl-W, N-methyl A, N-ethyl A, L, Pip, Aib, Y, or F; $X_4$ is E, Q, N, or D; $X_5$ is S, alpha methyl S, K, D, Orn, T, or E; $X_6$ is I, Chg, H, or L; $X_7$ is L or I; $X_8$ is D, N, E, or Q; $X_9$ is D, E, K, Q, or Orn; $X_{10}$ is H or methyl-H; $X_{11}$ is V, alpha methyl V, Chg, L I, or norvaline; $X_{12}$ is Q, Aib, S, R, or N; $X_{13}$ is R, K, citrulline, Orn, D, or E; $X_{14}$ is V, I, L, or norvaline; $X_{15}$ is W, Y, or F; and $X_{16}$ is R, G, or null.

3. A peptide comprising an amino acid sequence of any one of SEQ ID NO: 1-SEQ ID NO: 500.

4. A peptide comprising an amino acid sequence having at least 80%, 85%, 90%, 95%, 96%, 97%, 98%, 99%, or 100% sequence identity to any one of SEQ ID NO: 1-SEQ ID NO: 500. 5. The peptide of embodiments 1-4, wherein the peptide binds to β-catenin. 6. The peptide of embodiments 1-4, wherein the peptide is a β-catenin inhibitor. 7. The peptide of embodiments 1-4, wherein the peptide is an inhibitor of β-catenin translocation to the nucleus. 8. The peptide of embodiments 1-4, wherein the peptide prevents β-catenin acting as a transcription factor to oncogenes, Matrix Metalloproteinase 9 (MMP9), or Chloride C3 Channel (ClC-3). 9. The peptide of embodiments 1-4, wherein the peptide prevents transformation, invasion, migration, fibrogenesis, or any combination thereof, of EMS cells. 10. The peptide of embodiments 1-4, wherein the peptide prevents β-catenin from binding to estrogen receptor (ESR1). 11. The peptide of embodiments 1-4, wherein the peptide does not affect membrane activity of β-catenin. 12. The peptide of embodiments 1-4, wherein the peptide does not affect β-catenin E-cadherin binding. 13. The peptide of embodiments 1-4, wherein the peptide prevents oncogenic transcription factor activity. 14. The peptide of embodiments 1-13, wherein the peptide inhibits Wnt pathway activity with an $EC_{50}$ of less than 50 uM, less than 30uM, less than 10uM, 5 uM EC50, 1 uM, 500 nM, 400 nM, 300 nM, 200 nM, 100 nM, 50 nM, 30 nM, 10 nM, 5 nM, 3 nM, 1 nM, 800 pM, 600 pM, 400 pM, 200 pM, 100 pM, 50 pM, 30 pM, 20 pM, 10 pM, or 5 pM or less than about 10 uM, about 5 uM, about 1 uM, about 500 nM, about 400 nM, about 300 nM, about 200 nM, about 100 nM, about 50 nM, about 30 nM, about 10 nM, about 5 nM, about 3 nM, about 1 nM, about 800 pM, about 600 pM, about 400 pM, about 200 pM, about 100 pM, about 50 pM, about 30 pM, about 20 pM, about 10 pM, or about 5 pM and/or wherein the peptide binds β-catenin with a $KD_{50}$ binding affinity of less than about 50uM, about 30uM, 10 uM, about 5 uM, about 1 uM, about 500 nM, about 400 nM, about 300 nM, about 200 nM, about 100 nM, about 50 nM, about 30 nM, about 10 nM, about 5 nM, about 3 nM, about 1 nM, about 800 pM, about 600 pM, about 400 pM, about 200 pM, about 100 pM, about 50 pM, about 30 pM, about 20 pM, about 10 pM, or about 5 pM or less than 10 uM, 5 uM, 1 uM, 500 nM, 400 nM, 300 nM, 200 nM, 100 nM, 50 nM, 30 nM, 10 nM, 5 nM, 3 nM, 1 nM, 800 pM, 600 pM, 400 pM, 200 pM, 100 pM, 50 pM, 30 pM, 20 pM, 10 pM, or 5 pM. 15. The peptide of any of the preceding embodiments, wherein the peptide is non-naturally occurring. 16. The peptide of any of the preceding embodiments, wherein the peptide is a circularized peptide. 17. The peptide of embodiments 1-15, wherein the peptide is a bicyclic peptide. 18. The peptide of any one of embodiments 16 or 17, wherein the peptide is circularized with a Cys-Cys disulfide bond. 19. The peptide of any one of embodiment 16 or 17, wherein the peptide is circularized with an amide bond. 20. The peptide of embodiment 19, wherein the amide bond is head-to-tail between N-terminus and C-terminus. 21. The peptide of embodiment 19, wherein the amide bond is head-to-side chain between N-terminus and an internal COOH. 22. The peptide of embodiment 19, wherein the amide bond is side chain-to-tail between an internal NH2 and C-terminus. 23. The peptide of embodiment 19, wherein the amide bond is side chain-to-side chain between an internal NH2 and an internal COOH. 24. The peptide of embodiment 16 or 17, wherein the peptide is circularized using hydrocarbon stapling. 25. The peptide of embodiment 16 or 17, wherein the peptide is circularized using click chemistry. 26. The peptide of any one of the preceding embodiments, wherein the peptide is at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, or at least 81 amino acid residues. 27. The peptide of any one of the preceding embodiments, wherein the peptide is less than 4, less than 5, less than 6, less than 7, less than 8, less than 9, less than 10, less than 11, less than 12, less than 13, less than 14, less than 15, less than 16, less than 17, less than 18, less than 19, less than 20, less than 21, less than 22, less than 23, less than 24, less than 25, less than 26, less than 27, less than 28, less than 29, less than 30, less than 31, less than 32, less than 33, less than 34, less than 35, less than 36, less than 37, less than 38, less than 39, less than 40, less than 41, less than 42, less than 43, less than 44, less than 45, less than 46, less than 47, less than 48, less than 49, less than 50, less than 51, less than 52, less than 53, less than 54, less than 55, less than 56, less than 57, less than 58, less than 59, less than 60, less than 61, less than 62, less than 63, less than 64, less than 65, less than 66, less than 67, less than 68, less than 69, less than 70, less than 71, less than 72, less than 73, less than 74, less than 75, less than 76, less than 77, less than 78, less than 79, less than 80, or less than 81 amino acid residues. 28. The peptide of any one of the preceding embodiments, wherein the peptide comprises one or more non-natural amino acids. 29. The peptide of embodiment 28, wherein the one or more non-natural amino acids are N-methyl amino acids.
30. A pharmaceutical composition comprising: a β-catenin inhibitor; and a pharmaceutically acceptable carrier.
31. A pharmaceutical composition comprising: a peptide comprising binding specificity to β-catenin; and a pharmaceutically acceptable carrier.
32. A pharmaceutical composition comprising: a β-catenin inhibitor comprising a peptide; and a pharmaceutically acceptable carrier.
33. A pharmaceutical composition comprising: the peptide of any one of embodiments 1-29; and a pharmaceutically acceptable carrier. 34. The pharmaceutical composition of any one of embodiments 30-33, wherein the peptide is a circularized peptide. 35. The pharmaceutical composition of embodiments 30-33, wherein the composition comprises an absorption or permeation enhancer. 36. The pharmaceutical composition of embodiment 35, wherein the absorption enhancer comprises one or more of, sulphoxides, such as dimethyl sulphoxides (DMSO); laurocapran (1-dodecylaza-cycloheptan-2-one); pyrrolidones, such as n-methyl-2-pyrrolidone; terpenes and terpenoids; essential oils; oxazolidinones, such as 4-decycloxazolidin-2-one; urea; cyclopentadecalactone; sodium N-[8-(2-hydroxylbenzoyl) amino] caprylate (SNAC); 8-(N-2-hydroxy-5-chloro-benzoyl)-amino-caprylic acid (5-CNAC); medium chain fatty acids, salts, and derivatives; sodium caprate; sodium caprylate; protease inhibitor and omega-3 fatty acid; liquid mixed-micelle spray; lipid polymer micelle; alkylglycosides; chitosan; dodecyl-2-N,N-dimethylamino propionate (DDAIP); cell-membrane-lipid components; nanoparticles; liposomes; ligands; and lipophilic modifications. 37. The pharmaceutical composition of embodiment 36, wherein the absorption enhancer is sodium caprate.
38. A formulation comprising the peptide of any one of embodiments 1-29 or the pharmaceutical composition of any one of embodiments 30-37, wherein the formulation comprises a solution, lotion, shake lotion, cream, ointment, gel, foam, powder, solid, paste, tincture, microparticle, microcapsule, nanoparticle, liposome, emulsion, or lyophilisate. 39. The formulation of embodiment 38, wherein the gel is a thermoreversible gel. 40. The formulation of embodiment 38, wherein the formulation comprises one or more mucoadhesive polymers. 41. The formulation of embodiment 38, wherein the formulation is for topical administration. 42. An intravaginal device comprising the peptide of any one of embodiments 1-29 or the pharmaceutical composition of any one of embodiments 30-37. 43. The intravaginal device of embodiment 42, wherein the intravaginal device is a suppository, transdermal patch, sponge, tape, film, intravaginal ring, vaginal tampon, vaginal ring, vaginal strip, vaginal capsule, vaginal tablet, vaginal pessary, vaginal cup, vaginal sponge, or intrauterine device. 44. The intravaginal device of embodiment 42, wherein the peptide or the pharmaceutical composition is formulated as a formulation selected from the group consisting of a solution, lotion, shake lotion, cream, ointment, gel, foam, mucoadhesive composition, coating, core, matrix, emulsion, liposomes, or lyophilisate, wherein the intravaginal device comprises the formulation. 45. The intravaginal device of embodiment 42, wherein the intravaginal device comprises from about 0.01 mg to about 5000 mg of inhibitor. 46. The intravaginal device of embodiment 42, wherein the intravaginal device comprises about 0.01 mg, about 0.05 mg, about 0.1 mg, about 0.5 mg, about 1 mg, about 5 mg, about 10 mg, about 20 mg, about 40 mg, about 60 mg, about 80 mg, about 100 mg, about 150 mg, about 200 mg, about 400 mg, about 600 mg, about 800 mg, about 1000 mg, about 1200 mg, about 1400 mg, about 1600 mg, about 1800 mg, about 2000 mg, about 2500 mg, about 3000 mg, about 3500 mg, about 4000 mg, about 4500 mg, or about 5000 mg inhibitor. 47. The intravaginal device of embodiment 42, wherein the intravaginal device is configured to deliver the inhibitor transmucosally. 48. The intravaginal device of embodiment 42, wherein the intravaginal device is configured to deliver inhibitor over 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 18 hours, 19 hours, 20 hours, 21 hours, 22 hours, 23 hours, 24 hours, 1 day, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 1 month, 2 months, 3 months, 4 months, 5 months, 6 months, 7 months, 8 months, 9 months, 10 months, 11 months, 12 months, 1 year, 2 years, 3 years, 4 years, 5 years, 6 years, 7 years, 8 years, 9 years, 10 years, 11 years, or 12 years. 49. The intravaginal device of embodiment 42, wherein the intravaginal device is configured to deliver from about 0.01 mg to about 1000 mg inhibitor/day. 50. The intravaginal device of embodiment 42, wherein the intravaginal device is configured to deliver about 0.01 mg, about 0.05 mg, about 0.1 mg, about 0.5 mg, about 1 mg, about 5 mg, about 10 mg, about 20 mg, about 40 mg, about 60 mg, about 80 mg, about 100 mg, about 150 mg, about 200 mg, about 400 mg, about 600 mg, about 800 mg, or about 1000 mg inhibitor/day. 51. The intravaginal device of embodiment 43, wherein the device is the suppository. 52. The intravaginal device of embodiment 43, wherein the device is the transdermal patch. 53. The intravaginal device of embodiment 43, wherein the device is the sponge. 54. The intravaginal device of embodiment 43, wherein the device is the tape. 55. The intravaginal device of embodiment 43, wherein the device is the intravaginal ring. 56. The intravaginal device of embodiment 55, wherein the intravaginal ring comprises a silicone insert, a compressed tablet, or a lyophilized gel. 57. The intravaginal device of embodiment 56, wherein the peptide or the composition is incorporated throughout the silicone insert, the compressed tablet, or the lyophilized gel. 58. The intravaginal device of embodiment 43, wherein the device is the vaginal tampon. 59. The intravaginal device of embodiment 43, wherein the device is the vaginal ring. 60. The intravaginal device of embodiment 43, wherein the device is the vaginal strip. 61. The intravaginal device of embodiment 43, wherein the device is the vaginal capsule. 62. The intravaginal device of embodiment 43, wherein the device is the vaginal tablet. 63. The intravaginal device of embodiment 43, wherein the device is the vaginal pessary. 64. The intravaginal device of embodiment 43, wherein the device is the vaginal cup.

65. The intravaginal device of embodiment 43, wherein the device is the vaginal sponge. 66. The intravaginal device of embodiment 43, wherein the device is the intrauterine device.

67. A formulation comprising the peptide of any one of embodiments 1-29 or the pharmaceutical composition of any one of embodiments 30-37, wherein the formulation is for oral administration. 68. The formulation of embodiment 67, wherein the formulation is a tablet or capsule. 69. The formulation of embodiment 67, wherein the formulation is a liquid.

70. A method of inhibiting β-catenin in a subject comprising inserting the device of any one of embodiments 42-66 into the vagina of the subject.

71. A method of inhibiting β-catenin comprising contacting a cell with the peptide of any one of embodiments 1-29 or the pharmaceutical composition of any one of embodiments 30-37.

72. A method of treating endometriosis comprising administering a therapeutically effective amount of the peptide of any one of embodiments 1-29 or the pharmaceutical composition of any one of embodiments 30-37 to a subject in need thereof.

73. A method of reducing symptoms associated with endometriosis comprising administering a therapeutically effective amount of the peptide of any one of embodiments 1-29 or the pharmaceutical composition of any one of embodiments 30-37 to a subject in need thereof. 74. The method of embodiment 73, wherein the symptoms comprise at least one selected from the group consisting of chronic pain, central sensitization, myofascial pain, adnexal masses, infertility, dysmenorrhea, genetic predisposition, nonmenstrual pelvic-abdominal pain, dyspareunia, bowel symptoms (diarrhea, cramping, constipation), defecation pain (dyschezia), ovarian mass or tumor, painful bladder symptoms, and dysuria.

75. A method of treating a condition comprising administering to a subject a therapeutically effective amount of the peptide of any one of embodiments 1-29 or the pharmaceutical composition according to any one of embodiments 30-37. 76. The method of embodiment 75, wherein the condition is a tissue-infiltration condition, a tissue migration condition, a tissue invasion condition, or a combination thereof. 77. The method of embodiment 75, wherein the condition comprises a cancer. 78. The method of embodiment 77, wherein the cancer comprises colorectal carcinoma, squamous cell carcinoma, head and neck cancer, pancreatic cancer, breast cancer, myeloid leukemia, basal cell carcinoma, synovial sarcoma, non-small cell lung cancer, a solid tumor, or prostate cancer. 79. The method of embodiment 75, wherein the condition comprises endometriosis. 80. The method of any one of embodiments 71-79, wherein the peptide binds to β-catenin. 81. The method of any one of embodiments 71-80, wherein the peptide inhibits β-catenin. 82. The method of embodiment 80, wherein the peptide binds to cytoplasmic β-catenin. 83. The method of embodiment 82, wherein the peptide binds to cytoplasmic β-catenin to inhibit translocation of β-catenin to a nucleus of a cell. 84. The method of embodiment 82, wherein the peptide binds to cytoplasmic β-catenin to decrease an amount of free nuclear β-catenin. 85. The method of embodiment 82, wherein the peptide binds to cytoplasmic β-catenin to prevent β-catenin acting as a transcription factor to oncogenes, Matrix Metalloproteinase 9 (MMP9), or Chloride C3 Channel (ClC-3). 86. The method of embodiment 82, wherein the peptide binds to cytoplasmic β-catenin to prevent transformation, invasion, migration, fibrogenesis, or any combination thereof, of EMS cells. 87. The method of embodiment 82, wherein the peptide binds to cytoplasmic β-catenin to prevent β-catenin from binding to estrogen receptor (ESR1). 88. The method of embodiment 82, wherein the peptide binds to cytoplasmic β-catenin and membrane activity of β-catenin is not decreased. 89. The method of embodiment 82, wherein the peptide binds to cytoplasmic β-catenin and β-catenin-E-cadherin binding is not decreased. 90. The method of embodiment 76, wherein the peptide prevents oncogenic transcription factor activity. 91. The method of embodiment 84, wherein the amount of membrane β-catenin in a cell of the subject is increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or at least 100%. 92. The method of embodiment 91, wherein the increase in membrane β-catenin is relative to a cell of a control subject who was not administered the therapeutically effective amount of the pharmaceutical composition. 93. The method of embodiment 91, wherein the increase in membrane cytoplasmic β-catenin is relative to a cell of the subject taken prior to the subject developing the condition. 94. The method of embodiment 91, wherein the increase in membrane β-catenin is relative to a cell from the subject taken at a different timepoint. 95. The method of any one of embodiments 72 to 94, wherein the therapeutically effective amount is from about 0.01 mg to about 1000 mg.

96. A method of preventing a condition comprising administering to a subject a therapeutically effective amount of the peptide of any one of embodiments 1-29 or the pharmaceutical composition according to any one of embodiments 30-37. 97. The method of embodiment 96, wherein the condition is a tissue-infiltration condition, a tissue migration condition, a tissue invasion condition, or a combination thereof. 98. The method of embodiment 96, wherein the condition comprises a cancer. 99. The method of embodiment 98, wherein the cancer comprises colorectal carcinoma, squamous cell carcinoma, head and neck cancer, pancreatic cancer, breast cancer, myeloid leukemia, basal cell carcinoma, synovial sarcoma, non-small cell lung cancer, a solid tumor, or prostate cancer. 100. The method of embodiment 98, wherein the condition comprises endometriosis. 101. The method of any one of embodiments 96-100, wherein the peptide binds to β-catenin. 102. The method of any one of embodiments 96-101, wherein the peptide inhibits β-catenin. 103. The method of embodiment 101, wherein the peptide binds to cytoplasmic β-catenin. 104. The method of embodiment 103, wherein the peptide binds to cytoplasmic β-catenin to inhibit translocation of β-catenin to a nucleus of a cell. 105. The method of embodiment 103, wherein the peptide binds to cytoplasmic β-catenin to decrease an amount of free nuclear β-catenin. 106. The method of embodiment 103, wherein the peptide binds to cytoplasmic β-catenin to prevents β-catenin acting as a transcription factor to oncogenes, Matrix Metalloproteinase 9 (MMP9), or Chloride C3 Channel (ClC-3). 107. The method of embodiment 103, wherein the peptide prevents transformation, invasion, migration, fibrogenesis, or any combination thereof, of EMS cells. 108. The method of embodiment 103, wherein the peptide prevents β-catenin from binding to estrogen receptor (ESR1). 109. The method of embodiment 103, wherein the peptide binds to cytoplasmic β-catenin and membrane activity of β-catenin is not decreased. 110. The method of embodiment 103, wherein the peptide binds to cytoplasmic β-catenin and β-catenin-E-cadherin binding is not affected. 111. The method of embodiment 96, wherein the peptide prevents oncogenic transcription factor activity. 112. The method of embodiment 105, wherein the amount of free nuclear β-catenin in a cell of the subject is reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or at least 100%. 113. The method of embodiment 112, wherein the reduction in free cytoplasmic β-catenin is relative to a cell of a control subject who was not administered the therapeutically effective amount of the pharmaceutical composition. 114. The method of embodiment 112, wherein the reduction in free nuclear β-catenin is relative to a cell of the subject taken prior to the subject developing the endometriosis or tissue-infiltrating condition. 115 The method of embodiment 112, wherein the reduction in free cytoplasmic β-catenin is relative to a cell from the subject taken at a different timepoint. 116. The method of any one of embodiments 96 to 115, wherein the therapeutically effective amount is from about 0.01 mg to about 1000 mg. 117. The method of any one of embodiments 72-116, wherein the peptide or pharmaceutical composition is administered intravenously. 118. The method of any one of embodiments 72-116, wherein the peptide or pharmaceutical composition is administered intramuscularly. 119. The method of any one of embodiments 72-116, wherein the peptide or pharmaceutical composition is administered concurrently to administration of a medication to treat osteoporosis. 120. The method of embodiment 119 wherein the medication to treat osteoporosis comprises alendronate, ibandronate, risedronate, zoledronic acid, denosumab, calcitonin, estrogen, raloxifene, bazodoxifene, teriparatide, abaloparatide, or any combination thereof. 121. The method of embodiment 119, wherein the medication to treat osteoporosis is zoledronic acid.

VI. EXAMPLES

The following examples are included for illustrative purposes only and are not intended to limit the scope of the disclosure.

Example 1 Peptide Synthesis

Antisense Met-$X_1$—$X_2$—$X_3$—$X_4$—$X_5$—$X_6$—$X_7$—$X_8$—$X_9$—$X_{10}$-Lys single-stranded DNA template was synthesized at the Keck Oligonucleotide Synthesis Facility (Yale) and the sequence is 5' . . . GCCAGACCCCGAT-TTSNNSNNSNNSNNSNNSNNSNNSNNSNNSNNCAT-TGTAATT GTAAATAGTAATTG . . . 3' (SEQ ID NO:499), where N=A, T, C, G and S=G, C. The reagent bottle used for the "N" positions was made by mixing A:C:G:T in the ratio 3:3:2:2. The reagent bottle for "S" positions was made by mixing C:G in a 3:2 ratio. MX10K library double-stranded DNA was amplified by five cycles of polymerase chain reaction (PCR) using the forward primer Gen-FP (5'-TAATACGACTCACTATAGGGACAATTACTATTTA-CAATTACA-3') (SEQ ID NO: 500) and the reverse primer $MK_{10}K$-RP (5'-ACCGCTGCCAGACCCCGATTT-3') (SEQ ID NO: 501). The Round 0 mRNA pool was generated by T7 runoff transcription and purified by urea-PAGE. The purified mRNA was ligated to F30P (5'-dA21[C9]3dAdCdC-P; C9=tri-(ethylene glycol) phosphate(Glen Research), P=puromycin (Glen Research)), via an oligonucleotide splint ($MX_{10}$K-splint: 5' . . . TTTTTTTTTTTT-TACCGCTGCCAGAC . . . 3') (SEQ ID NO: 503). Following PAGE purification of the ligation reaction, the template was dissolved in water and quantitated by absorbance at 260 nm.

Example 2 Synthesis and Cyclization of Peptides

Increased protease resistance is shown in peptides containing N-methyl amino acids. Additionally, cyclization of peptides has been shown to increase binding affinity of ligand peptides.

All solvents were purchased from Sigma. All peptides except N-Me-L14 were synthesized by manual solid-phase peptide synthesis with preloaded Leu-2-chlorotrityl resin (250 mg, 0.15mmol; Anaspec). N-Me-L14 was synthesized after loading 2-chlorotrityl resin (Anaspec) with Fmoc-N-methyl leucine (Fmoc=9-fluorenylmethoxycarbonyl; Anaspec). Five N-terminal Asn residues were added to enhance peptide solubility. Loading was accomplished by adding FmocN-Me-L14to 2-chlorotrityl resin (5 equiv; 250 mg, 0.35 mmol) in DMF with N,N diisopropylethylamine (DIEA; 5 equiv) for 2 h. Standard couplings were carried out with monomer (5 equiv; Novabiochem) in HATU (2 mL, 0.6 mmol; Novabiochem), HOAt (1.2 mmol; Genescript) in DMF with DIEA (1.8 mmol) at room temperature for 15 min. Coupling to an N-methyl amino acid followed the same procedure with a 30 min coupling time. Fmoc deprotection was carried out with 20% piperidine (Anaspec) at room temperature for 15 min. Following, deprotection, cleavage with 95% TFA, filtration and ether extraction, the crude product was purified on a Vydac C-18 reversed-phase column using gradient elution (0% B for 5 min, 10-50% B in 40 min. Solvent A: H2O with 0.1% TFA, Solvent B: CH3CN with0.035% TFA). Lyophilized solid was reconstituted in DMSO and quantitated by absorbance at 280 nm (ε280=12490 L mol-1 cm-1). Yield=20-25%.

Peptides were cyclized by adding 190 μL of dT-purified fusions in 50mM phosphate buffer (pH=8) to 50 μL of DSG (1 mg/mL in DMF). The reaction was allowed to proceed for 1 h, and the fusions were repurified by dT-cellulose and ethanol precipitated. This process yields cyclic peptides.

Example 3 Nuclear β-Catenin Inhibition and Wnt Signaling

Figure 2A:
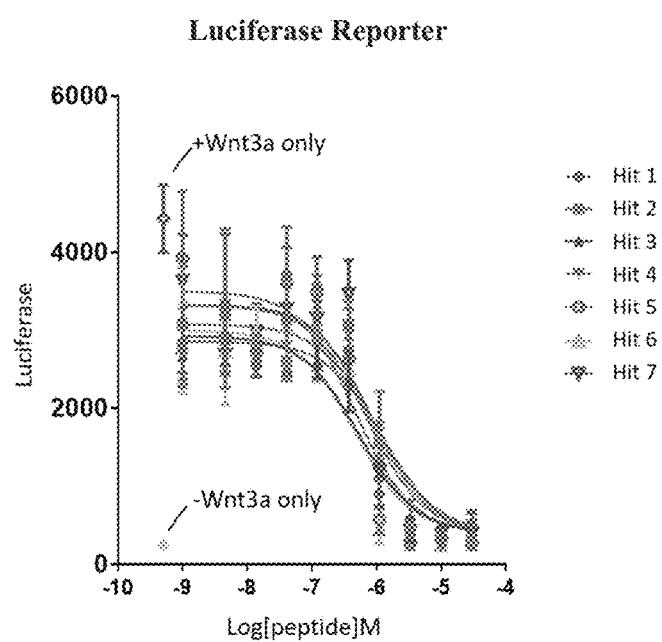
FIG. 2A shows luciferase expression in transfected reporter cells controlled by a Wnt-responsive promoter incubated with β-catenin-inhibiting peptides.

Peptides were assessed for their ability to inhibit Wnt signaling. Murine 3T3 fibroblasts that express luciferase under a Wnt-responsive promoter (TCF/LEF) (Enzo Life Sciences, Farmingdale, NY) were stimulated with Wnt3a in the presence of increasing concentrations of peptide inhibitor (Hit 1: SEQ ID NO:217, Hit 2: SEQ ID NO:224, Hit 3: SEQ ID NO:228, Hit 4: SEQ ID NO:227, Hit 5: SEQ ID NO:220, Hit 6: SEQ ID NO:168. Hit 7: SEQ ID NO:226) or with vehicle control (FIG. 2A). Optimized compounds showed $EC_{50}$ values in the 500-999 nM range and luciferase levels reduced to that of unstimulated (−Wnt3a) control. Luciferase activity was not affected by addition of a scrambled peptide (containing the same amino acids in a scrambled manner), a non-functional peptide (peptide does not target β-catenin), or a non-permeable peptide (peptide without permeability-enhancing features). Results indicate a concentration-dependent suppression of Wnt-responsive promoter with peptides described herein. conc dep supp.

Figure 3:
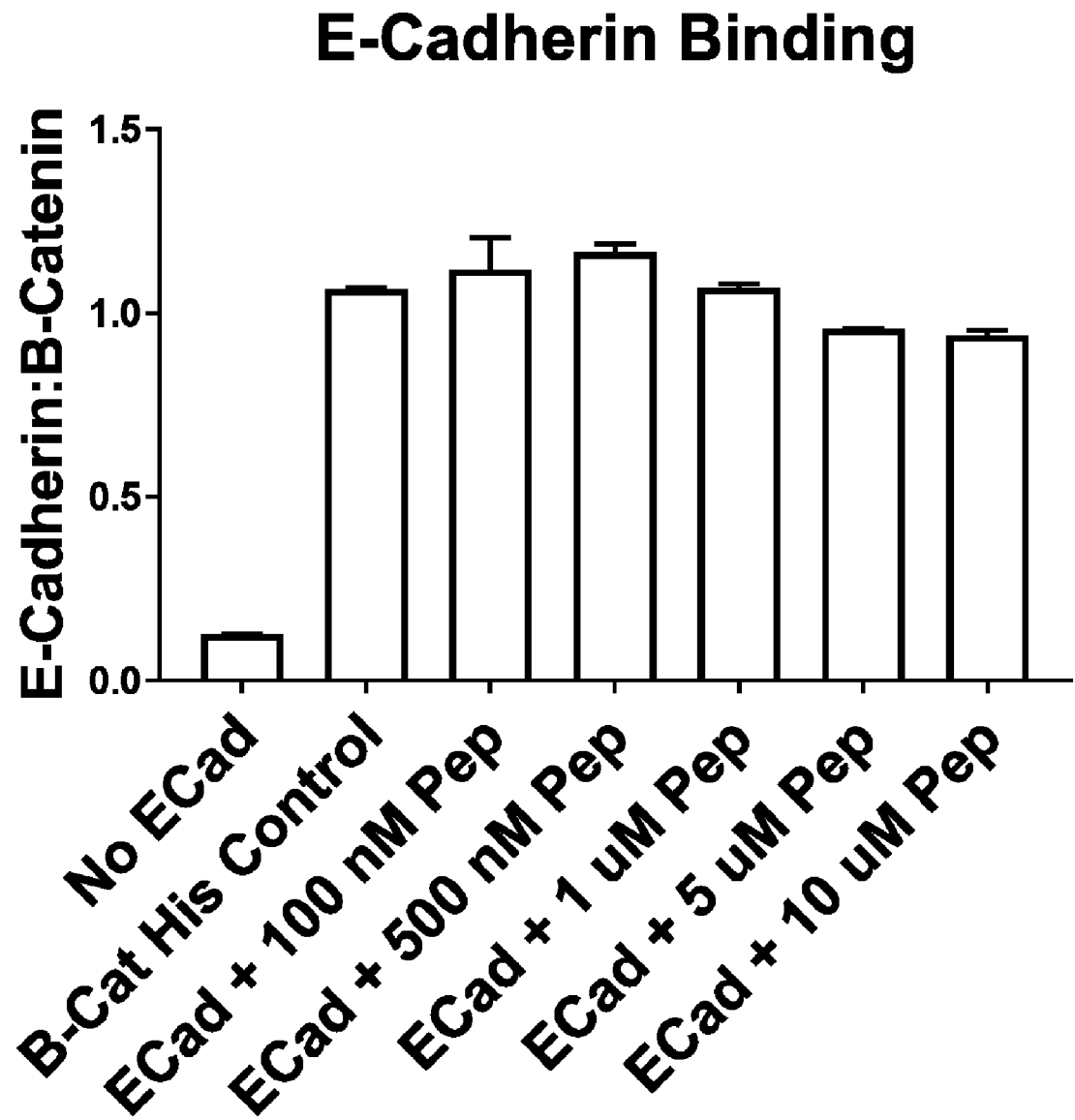
FIG. 3 shows E-Cadherin binding in the presence of β-catenin-inhibiting peptide corresponding to SEQ ID NO: 42.

Example 4 Peptides Do Not Inhibit Membrane Bound β-Catenin or Block Access to Binding Site on E-Cadherin Competitive binding assays were performed (FIG. 3) wherein biotinylated β-catenin was immobilized on streptavidin plates and 50 nM E-Cadherin-FC fusion was added in the presence of varying amounts of the peptide inhibitors (SEQ ID NO: 42). None of the doses tested inhibited the β-catenin and E-Cadherin interaction. The results show that the peptides do not inhibit membrane bound β-catenin or block access to binding site on E-cadherin.

Example 5 β-Catenin Inhibitors Cause Lesion Regression

A study was conducted to assess the impact of β-catenin on mouse models of endometriosis. Lesions were established in an EMS mouse model of endometriosis by intraperitoneal injection of minced GFP+ uterine tissue from a mouse into wild-type c57/b16 mice. Lesions from this mouse model mimic sites of attachment found in humans. The lesions are organized with defined epithelial glandular structures, organized stroma, and hemosiderin-laden macrophages. The lesions respond to hormones and express β-catenin, MMPs, Wnt4, PGR, and ESRs. Endometrial disease was established in the mice and allowed to progress for three weeks prior to the initiation of therapy.

Figure 4A:
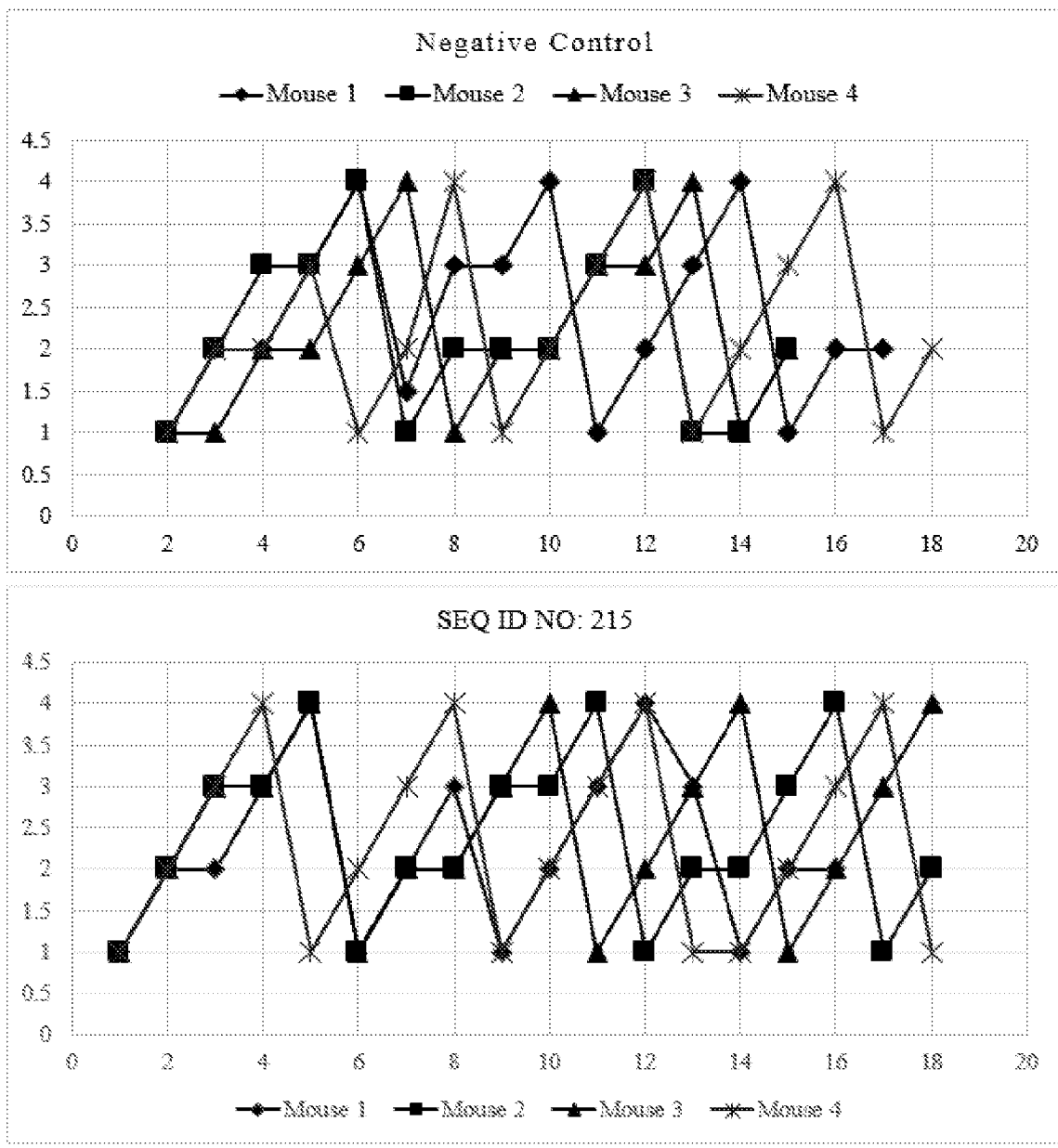
FIGS. 4A-4C show peptide inhibitors to β-catenin cause lesion regression.

After this establishment phase, mice were treated IP daily for three weeks with either vehicle (PBS+0.5% DMSO negative control) or the macrocyclic peptide Cyclo-acetyl-K*Nle-W-3-cyclohexyl-L-alanine-LI-(amino butyric acid-AWD*-COOH) (SEQ ID NO: 215), "Peptide 2," (PBS+5 mg/kg Peptide 2 in 0.5% DMSO). Vaginal smears were taken daily, which demonstrated that mice treated with either vehicle or Peptide 2 progressed through 4 stages of the estrous cycle. FIG. 4A shows that mice cycle every 4-5 days through proestrus (P), estrus (E), diestrus (D), and metestrus (M) stages. Estrous patterns for vehicle and Peptide 2 are normal. No adverse effects on the uterus of the hypothalamic gonadal axis were indicated.

Figure 4B:
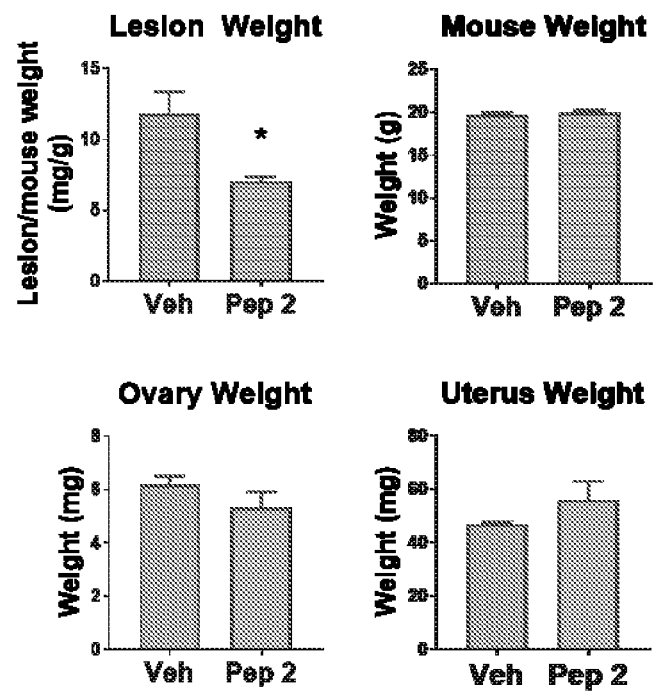
Figure 4C:
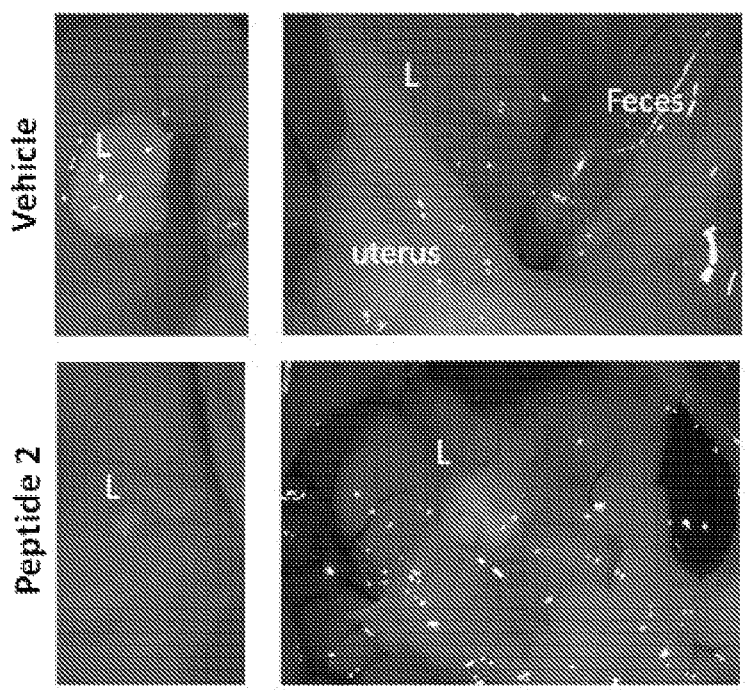
Figure 5A:
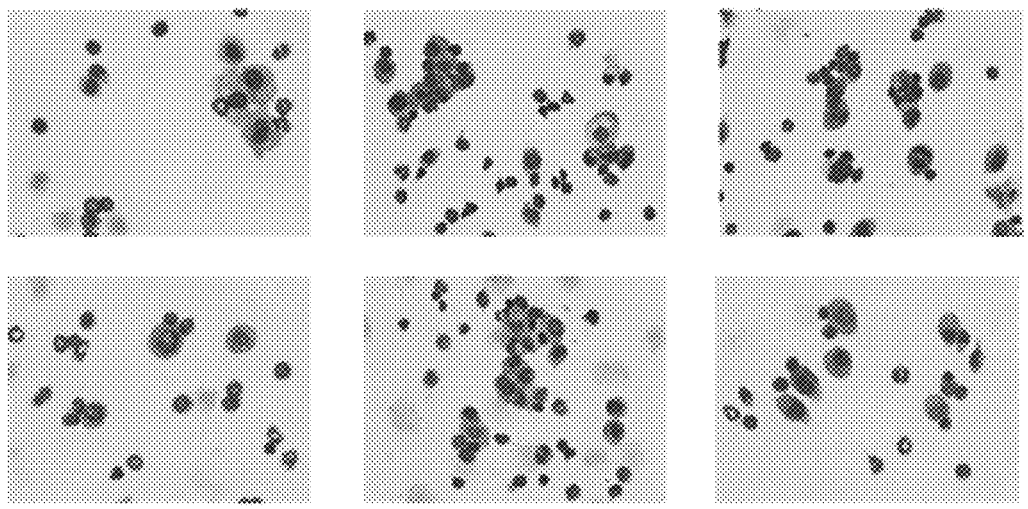
FIG. 5A shows histology of samples taken from EMS lesions in mice treated with vehicle alone.
Figure 5B:
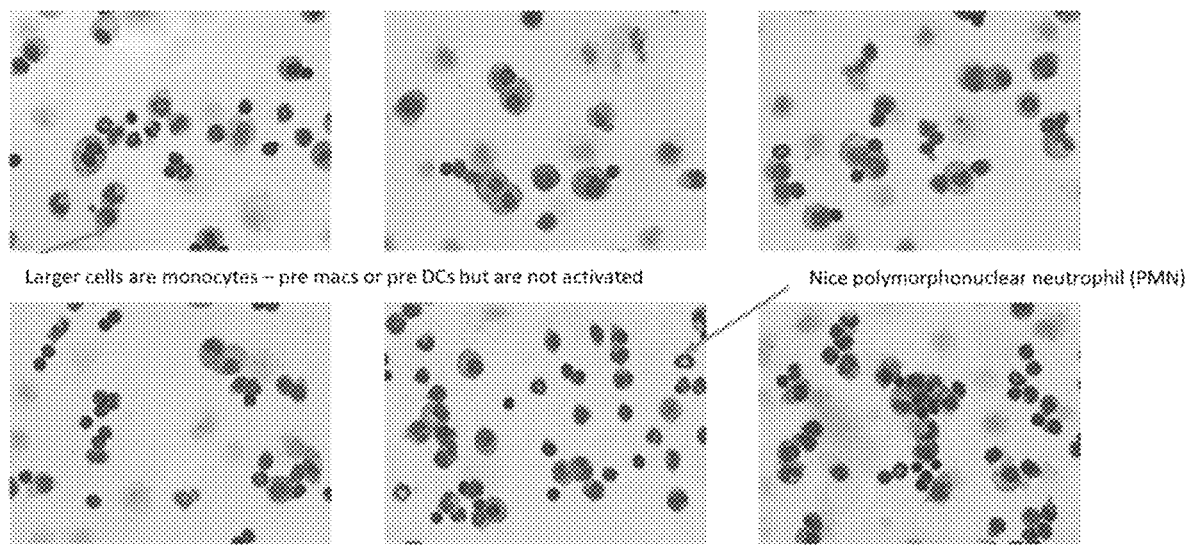
FIG. 5B shows histology of samples taken from EMS lesions in mice treated with Peptide 2.

Mice were then euthanized during estrus; mouse weight, ovary weight, and uterus weight were measured and determined to be consistent across treatment regimens (FIG. 4B). EMS lesions were reduced in size in Peptide 2-treated mice when compared to vehicle alone (FIG. 4B and FIG. 4C). A relative increase in activated macrophages was also observed in Peptide 2-treated mice when compared to vehicle alone. FIG. 5 shows an increase in the relative numbers of activated macrophages, foam cells, polymorphonuclear neutrophils, B cells, and T cells at the site of lesions treated with Peptide 2 (SEQ ID NO: 215) compared to vehicle alone as assessed by histology. Without wishing to be bound by theory, these results may suggest that the immune cells are phagocytosing the uterine tissue.

From this experiment, it can be concluded that Peptide 2, which is an inhibitor of β-catenin, causes lesion regression without altering estrous cyclicity, mouse weight, ovarian weight, or uterus weight. Together, these data demonstrate that Peptide 2 (1) is membrane-permeable and interferes with β-catenin's nuclear transcriptional function in a dose-dependent manner, (2) exhibits stability against proteases and sustained half-life, (3) does not affect β-catenin membrane binding to E-cadherin, (4) inhibits cell proliferation in cells with pathological and aberrant Wnt-dependent growth, (5) does not affect growth in healthy cells or disrupt membrane-bound β-catenin activity, and (6) regresses EMS lesions without altering uterine cyclicity or uterine weight.

Example 6 Therapeutic Potency of Peptides

Peptide inhibitors are tested for their ability to inhibit cellular proliferation across a panel of cell types including human endometrial stromal cells (HESCs) and/or primary EMS cells from different lesion subtypes (based on location and severity). Mouse uterine cells derived from mouse uterus are used as a control cell line to demonstrate the peptides do not inhibit normal cellular behavior. Primary EMS cells are excised from different patients and collected in accordance to the World Endometriosis Research Foundation Endometriosis Phenome and Biobanking Harmonization Project (EPHect) standard protocols. All cell lines are plated (5-10×10$^4$ cells/24 well plate in quadruplicate) and each peptide is administered daily for 5 days at 10 different concentrations (10-50,000 nM) along with a series of controls (see Table 2). After Day 5, the CellTiter-Glo® Luminescent Cell Viability Assay (Promega) is used to detect viable cells. IC50 values are graphed and calculated using Prism software (GraphPad) based on the cell viability readouts.

TABLE 2

Treatment and concentration ranges

| Treatment | Concentration |
| --- | --- |
| Macrocyclic peptides | 10-50,000 nM |
| Controls | |
| Scrambled peptide | 50,000 nM |
| Non-functional peptide | 50,000 nM |
| Positive control (ICG001) | 50,000 nM |
| Vehicle (DMSO in PBS) | 0.5% |

Example 7 Therapeutic Inhibition of Cellular Migration and Invasion In Vitro

In vitro cell migration and invasion of HESC, mouse EMS lesion cells, and human EMS lesion cells are analyzed using uncoated or Matrigel-coated 24-well chambers or microfilters (Becton Dickinson), respectively, as outlined by Matsuzaki et al., C. PLoS One 8, e61690. Upon stimulation and subsequent administration of compounds determined optimal in Examples 3 and 6 using the same controls, cell motility and migration are calculated by the number of cells that migrate to the unpopulated area of the chamber in 24 h, and cell invasion is calculated by the number of cells that invade the micropore filter in 24 h. These experiments are performed in quadruplicate and analyzed quantitatively with a computerized light microscope. The results are used to assess the ability of peptides to inhibit cellular migration and invasion.

Example 8 Confirmation of On-Target Activity of Therapeutic Molecules in Cell Lines On-target activity of each peptide is assessed by the transcriptional activity of >80 WNT pathway genes using Human WNT Signaling Pathway RT$^2$ Profiler PCR Array (Qiagen, Venlo, Netherlands). Primary cells are administered 500 nM of the selected peptide for 48 h. RNA is extracted from the harvested cells and profiled on the array using rtPCR. Included in the array are 84 genes related to Wnt-mediated signal transduction, comprising ligands, receptors, downstream signaling molecules, and regulators of the Wnt canonical pathway, two non-canonical pathways, planar cell polarity, and a calcium ion-dependent pathway. Western blot analysis of ClC-3 and zymography for MMP-9 activity are used to confirm selected proteins have decreased by ≥50% of initial levels. Cells are stained for β-catenin localization by immunofluorescence. Controls are as listed in Table 2.

Example 9 Therapeutic Regression of Lesions In Vivo

Compounds are selected for further testing of their therapeutic potential using mouse models of EMS. Mice are induced with EMS according to Burns, et al., *Endocrinology* 153, 3960-3971. Hormonally intact syngeneic mice are synchronized with pregnant mare serum gonadotropin (PMSG-5 IU). The uterus is removed after 41 h, when hormone levels and vaginal histology mimic metestrus/diestrus (data not shown). The outer myometrium and attached blood supply is peeled away, the uterus is slit longitudinally, and minced into 1-2 mm pieces in sterile saline. Minced uterine tissue is injected through a 5 mm dorsal lateral hole into the peritoneal cavity (Day 0). Minced uterine tissue is allowed to attach and grow for 3 weeks prior to intraperitoneal introduction of peptides. Mice are treated with 5 mg/kg, 10 mg/kg, and 20 mg/kg of peptide daily for 6 weeks. Mice are euthanized in estrus the $9^{th}$ week following initiation of EMS. Previous data are used as preliminary estimates of means and standard deviations to determine numbers (Table 3).

At necropsy, peritoneal cells and fluid are collected by peritoneal lavage. Lesions are removed (weight, volume, and location recorded) with surrounding tissue for histology/immunohistochemistry (IHC) or without for gene expression analysis by real-time PCR. Mice are injected 20 min prior to necropsy with Lectin (100 µg) and heparin sulfate (100 U) in order to histologically visualize blood vessels. Lesions are analyzed histologically for blood vessel density, organization/collagen (Masson's Trichrome), infiltration of white blood cells (i.e. neutrophils by Ly6G, macrophage by F4/80), proliferation (Ki67), β-catenin localization, and Wnt signaling molecules. Lesions are further used to examine Wnt/ β-catenin levels, and matrix metalloproteinase (MMP) activity using MMP zymography. Peritoneal fluid cells are analyzed for macrophages and neutrophils. Lesions are analyzed using real time-PCR to target genes most affected in the Wnt Signaling PCR Array in Example 4. Lesions from control treatment serve as baseline.

Compounds that decrease Wnt signaling, decrease lesion weight or volume, decrease MMP activity levels, reduce fibrosis, increase the infiltration of white blood cells in lesions, reduce the amount of nuclear β-catenin relative to controls or any combination thereof will be selected for further testing.

TABLE 3

| Power Analysis Based on Preliminary Data 50% Lesion weight decrease | | |
|---|---|---|
| | 80% | 90% |
| 6 week vehicle | 16 | 22 |
| 6 week peptide | 18 | 24 |

Example 10 Immunohistochemistry of Localization

Endometriosis was established in a mouse model of disease. Mice were allowed to establish endometriosis for 3 weeks. After the first 3 weeks, mice were then intraperitoneally treated daily for 3 weeks with the therapeutic peptides corresponding to SEQ ID NOs: 215 or 393 or untreated negative control. To assess the localization of the peptides and β-catenin, lesions from the endometriosis mouse model were assessed. On the last day of treatment, in order to visualize the peptide localization to the lesion(s), mice were dosed with a biotinylated tagged peptide therapeutic or control. Mice were euthanized, lesions were removed, and fixed in formalin for histology and immunohistochemistry. Fixed and sectioned lesions were incubated with antibodies specific for β-catenin (Cell Signaling, 1:100, Secondary: Fisher Scientific, Goat anti-Rabbit-647 1:200), streptavidin for biotinylated-therapeutic (Fisher Scientific, SA-405 1:100), and Sytox green for nucleus (Fisher Scientific, 1:300). Immunohistochemical negative controls were performed on lesion sections from all treatment groups using IgG non-specific antibodies (Rabbit-IgG, AbCam 1:100).

Figure 6A:
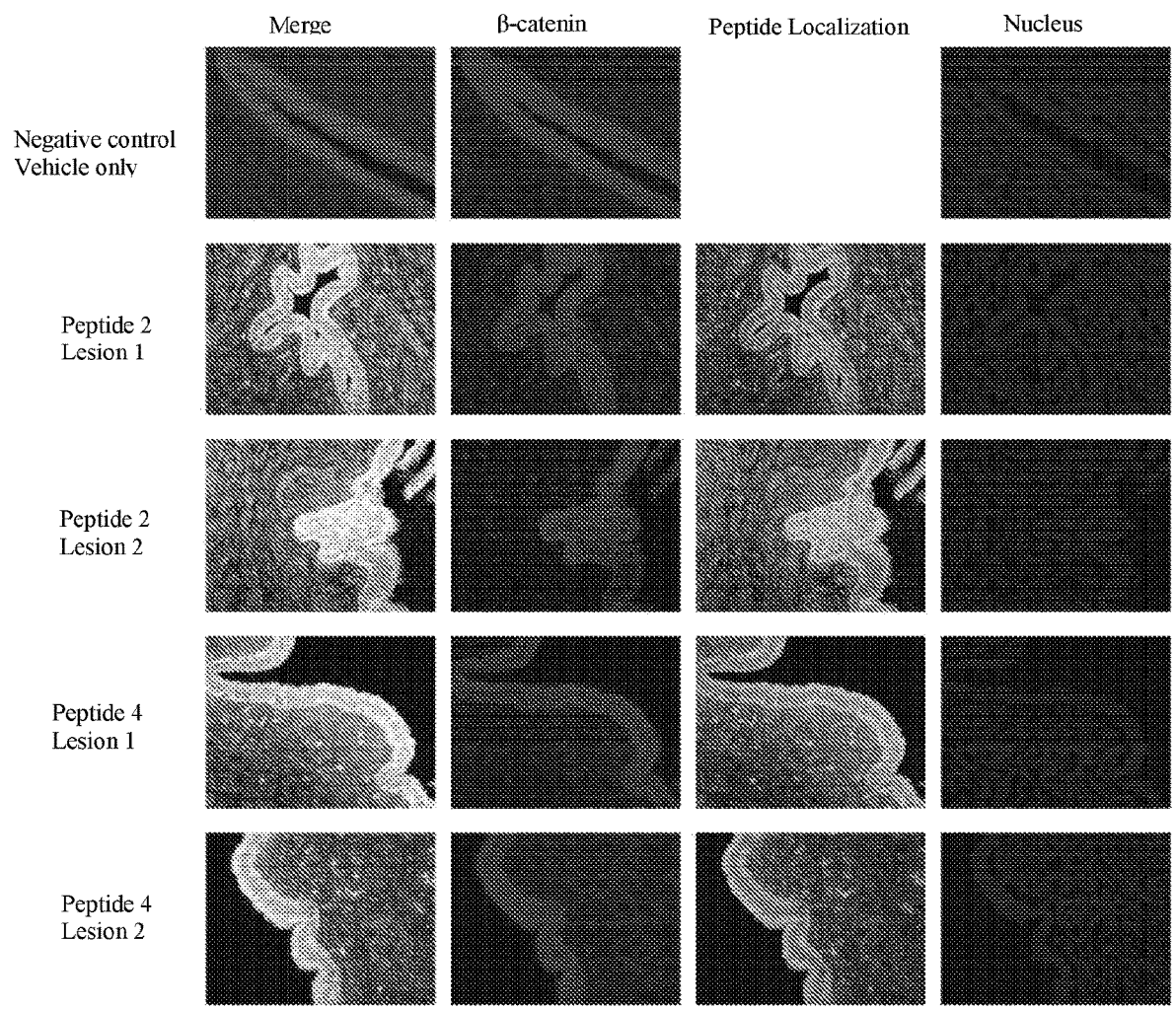
FIG. 6A shows representative slides at 20× magnification of mouse model endometriosis lesions stained to show β-catenin is not localized to the nucleus following treatment with therapeutic peptide and that peptide inhibitor follows b-catenin localization pattern.

Qualitatively, as shown in FIG. 6A, it is apparent that the targetβ-catenin is not localized to the nucleus when treated with the therapeutic peptides. Additionally, the therapeutic peptide also follows the localization pattern of β-catenin, which is decreased in the nucleus and is maintained/increased in the membrane. This implies that the peptide is membrane soluble, binds to cytoplasmic β-catenin, and does not disrupt the binding between β-catenin in the membrane. The therapeutic peptide binding may increase binding affinity of β-catenin to E-cadherin. Conversely, lesions that were control treated had more diffuse staining across the membrane, cytosol, and the nucleus. Additionally, as shown in FIG. 6B, the orthogonal slices show that the β-catenin in the peptide treated lesions are more membranous compared to control treated lesions. Localization of the therapeutic peptides correlate with β-catenin staining, as expected. In peptide treated lesions, localization of the peptide was visualized predominantly across the membrane.

Quantification ofβ-catenin localization was performed using the Zeiss Blue Software via thresholding. Thresholding allows the software to calculate the area of staining using pixel intensity; therefore, a quantitative number for staining can be extrapolated for the different cellular compartments (See Table 6).

TABLE 6

| Staining area threshold data | | |
|---|---|---|
| | % membrane bound | % nuclear |
| Vehicle only | | |
| Pep1 NE L1 | 22.1 | 1.2 |
| Pep1 NE L1_2 | 21.4 | 0.9 |
| Pep1 NE L5 | 5.0 | |

TABLE 6-continued

Staining area threshold data

|  | % membrane bound | % nuclear |
| --- | --- | --- |
| pep1 LE L1 | 4.6 | 4.3 |
| Pep1 LE L1_2 | 14.8 | 1.1 |
| pep1 BE L1 | 9.5 | 3.8 |
| Average | 12.9 | 2.3 |
| Standard deviation | 7.1 | 1.5 |
| Peptide 2 (SEQ ID NO: 215) | | |
| Pep2 RE L1_2 |  | 0.8 |
| pep2 LE L1 | 70.2 | 1.2 |
| Pep2 BE L1 | 22.7 | 1.1 |
| Average | 46.4 | 1.0 |
| Standard deviation | 23.8 | 0.2 |
| Peptide 4 (SEQ ID NO: 393/500) | | |
| pep4 NE L1 | 23.3 |  |
| pep4 NE L1_2 | 20.5 | 1.2 |
| pep 4 NE L4 | 39.5 | 0.2 |
| Pep4 NE L4_2 | 22.0 | 0.6 |
| pep4 RE L2 |  | 0.2 |
| pep 4 LE L1 | 15.3 | 0.4 |
| pep4 LE L2 | 25.8 | 0.7 |
| Average | 24.4 | 0.5 |
| Standard deviation | 7.4 | 0.3 |

Figure 7A:
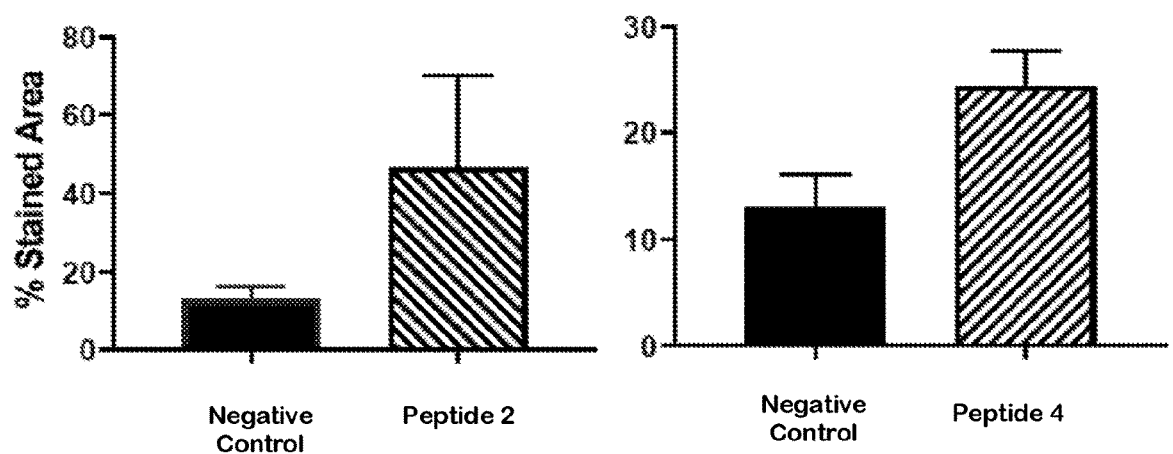
FIG. 7A compares quantification of membrane bound β-catenin in lesions treated with therapeutic peptide versus untreated control.
Figure 7B:
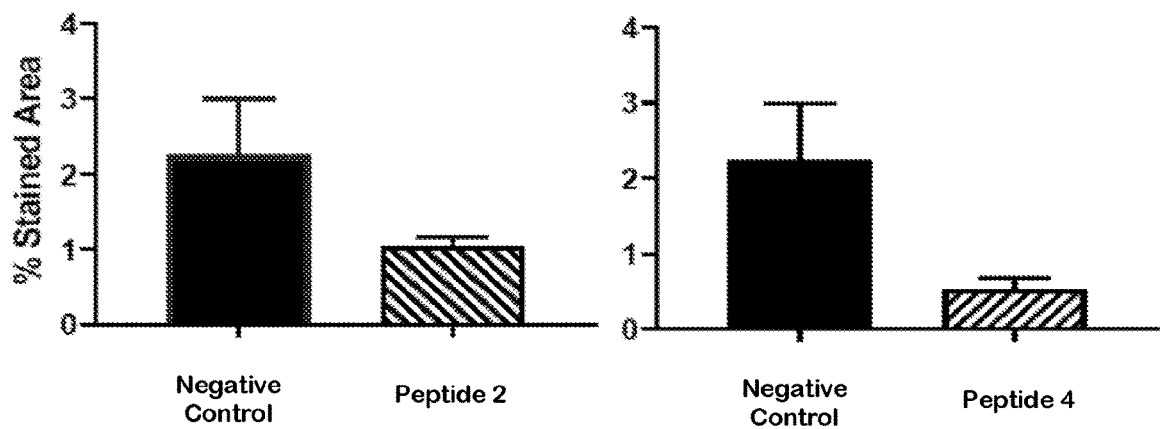
FIG. 7B compares quantification of nuclear β-catenin in lesions treated with therapeutic peptide versus untreated control.

Compiled area thresholding data show that β-catenin, from lesions receiving therapeutic treatment, is more membrane bound (See, FIG. 7A) when compared to control treated lesions. Additionally, nuclear β-catenin levels are decreased in lesions treated with therapeutic in comparison to control treated lesions (See, FIG. 7B).

Together, these data show that the therapeutic peptide maintains or increases β-catenin binding to the membrane and inhibits nuclear β-catenin localization.

Example 11 KD50 Measurement Using Surface Plasmon Resonance (SPR)

Biotinylated protein (beta catenin) was immobilized on a high-affinity streptavidin (SA) sensor chip (GE). Peptide at increasing concentrations was flowed over in HBS EP+ buffer at room temperature according to manufacturer's instructions. The maximum binding capacity of the surface (response at saturation) was calculated using the Biacore® system (GE) instructions and binding was measured at each concentration as a data point. The binding levels were determined over a range of analyte concentrations of at least from 20% to 80% saturation of the surface. On rates, off rates, and KD were calculated using Biacore® Insight Evaluation Software software (GE). The concentration at saturation of 50% was calculated from these series of dilutions and presented as KD50 in Table 5. qPCR confirmed on-target activity of therapeutic molecules in cell lines On-target activity of each peptide was assessed by the transcriptional activity of WNT pathway genes using Qiagen's Human WNT Signaling Pathway RT² Profiler PCR Array). Primary cells were administered the therapeutic peptide corresponding to SEQ ID NO: 42 for 48 h. RNA was extracted from the harvested cells and profiled on the array using rtPCR. The array contains 84 genes related to Wnt-mediated signal transduction, including ligands, receptors, downstream signaling molecules, and regulators of the Wnt canonical pathway, two non-canonical pathways, planar cell polarity, and a calcium ion-dependent pathway, 38 of which were assessed here. Positive control of ICG001, a known Wnt inhibitor, was also run on the RNA array to be used as a comparison.

Figure 8A:
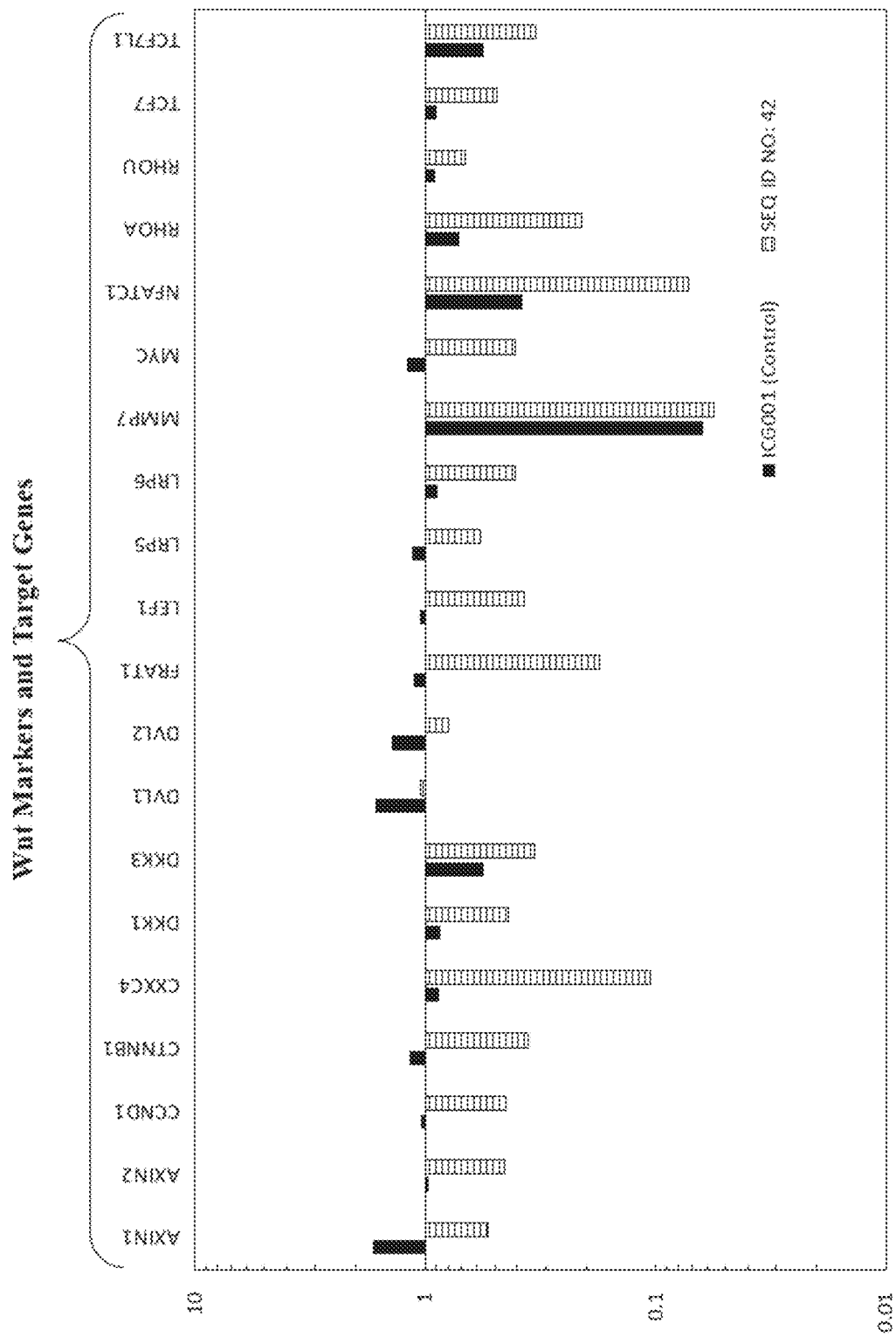
FIGS. 8A and 8B show therapeutic peptide inhibits gene transcripts in the Wnt pathway to a greater degree than a known positive control (ICG001).
Figure 8B:
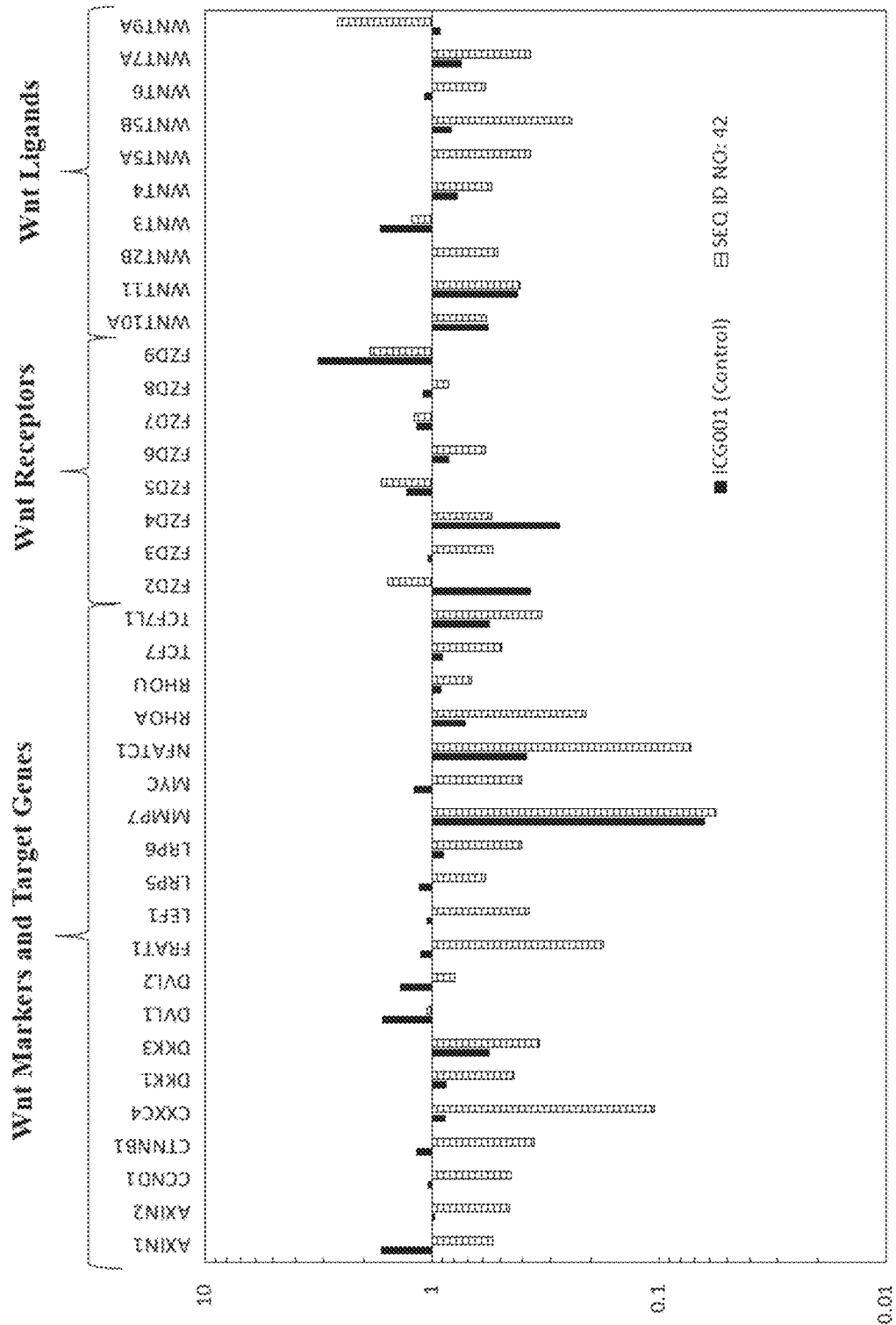

Results depicted in FIG. 8A and FIG. 8B show the therapeutic peptide corresponding to SEQ ID NO: 42 out-performed the known positive control by inhibiting several key gene transcripts within the Wnt pathway. Specifically, downstream Wnt marker and target genes, including AXIN1, AXIN2, CCND1, CTNNB1, CXXC4, DKK1, DKK3, DVL1, DVL2, FRAT1, LEF1, MMP7, MYC, NFATC1, RHOA, RHOU, TCF7, TCF7L1, WNT9A, and Wnt receptors and ligands, including FZD3, FZD4, FZD6, FZD8, WNT10A, WANT11, WANT2B, WNT4, WNT5A, WNT5B, WNT6, WNT7A were downregulated when a therapeutic peptide was administered. (See FIGS. 8A and 8B) The downregulation of these key transcripts may contribute to the anti-proliferative effects of the therapeutic observed in the endometriosis cells. Additionally, several Wnt receptors and ligands are upregulated, which is may be the result of apoptosis in these treated cells. Upregulated Wnt receptors and ligands include FZD5, FZD9, WNT3. Together, these results show that the therapeutic peptide corresponding to SEQ ID NO: 42 is a potent and specific Wnt inhibitor.

Example 12 KD50 Measurement Using Fluorescence Polarization (FP)

Figure 9:
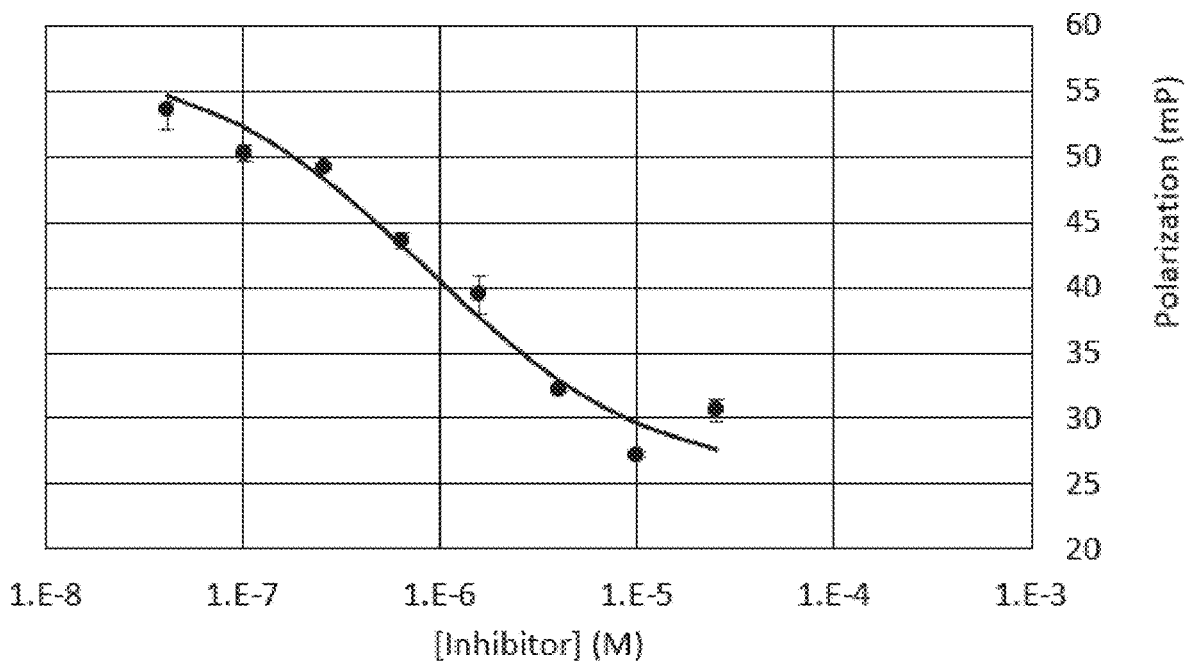
FIG. 9 shows the results of a fluorescence polarization assay using a peptide having SEQ ID NO: 404.

5nM of labelled TCF4 protein was added to solution of 100nM of β-catenin and incubated at room temperature in 96-well plates (Greiner 96 Flat transparent plates, Millipore Sigma, Carlsbad CA). Varying concentrations of β-catenin inhibitor candidate (SEQ ID NO: 404) were then added in a series of serial dilutions from 10nM to 30uM of inhibitor in different wells of the plate. The fluorescence polarization was read by Infinite M1000 (Tecan, Baldwin Park CA) at excitation wavelength of 470 nm and measured at emission wavelength of 520 nm. The corrected polarization measurements for background noise from the blank resulted in polarization intensity readings for each data point. The experiments were performed three times and data were analyzed and plotted in Microsoft Excel (Microsoft, Redmond, WA). An example showing the results for SEQ ID NO: 404 is shown in FIG. 9. The results show that the inhibitor binds β-catenin in a concentration-dependent anner.

Example 13 Peptide Effect on Cell Proliferation

Peptide inhibitors were tested for their ability to inhibit cellular proliferation across 2 different β-catenin expressing pathogenic cell lines: a colon cancer cell line (SW480) and/or mouse EMS lesion cells derived from mouse model of disease. Both cells lines are naturally known to express high levels of β-catenin. Cell lines were incubated with varying concentrations of peptide concentration and assessed for viability after day 5 and 7 days. The CellTiter-Glo® Luminescent Cell Viability Assay (Promega) is used to detect viable cells. IC50 values are graphed and calculated using Prism software (GraphPad) based on the cell viability readouts. IC50 is used to assess inhibition of cell proliferation by peptide concentration and is used to calculate the inhibitory effect of each peptide across each line. The results are used to assess the therapeutic potency of the peptides.

Figure 2B:
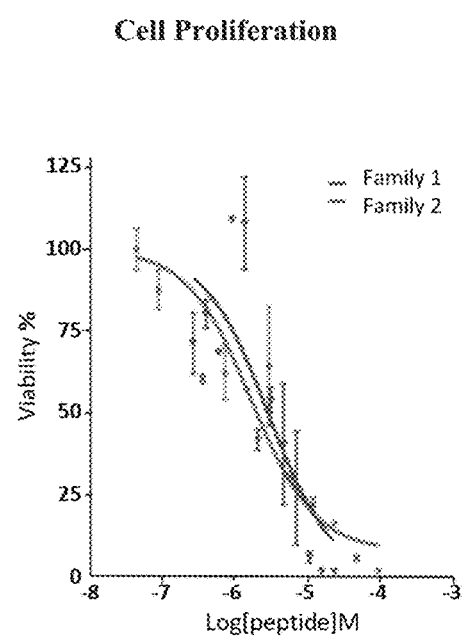
FIG. 2B shows cell proliferation in a β-catenin-expressing cell line after incubation with β-catenin-inhibiting peptides (SEQ ID NO: 264 and SEQ ID NO: 396).

In the SW480 cell line, peptide inhibitors from Family 1 (SEQ ID NO:264) and Family 2 (SEQ ID NO:396) were added daily to the cell growth medium. After 7 days, cell viability was assessed with the Cell-Titer Glo kit (Promega, Madison, WI). Both peptides inhibited cell growth after 7 days (FIG. 2B) in a concentration-dependent manner. In mouse EMS lesion cells derived from mouse model of disease, peptide inhibitor (SEQ ID NO:465) was added daily to the cell growth medium at concentrations of 25 uM, 12.5 uM, 6.25 uM, 3.125 uM, 1.56 uM, 0.78 uM, 0.39 uM, 0.195 uM, 0.098 uM, 0.049 uM, 0.024 uM, and 0 uM (negative control). After 5 days, cell viability was assessed and the peptide inhibited cell growth after 5 days in a dose-dependent manner. $IC_{50}$ was calculated for peptides based on the concentration at which 50% viability was observed (Table 5).

Example 14 Illustrative Compounds
Illustrative peptides are shown below. The peptides were synthesized as described in Example 1 and Example 2.
(SEQ ID NO: 33)
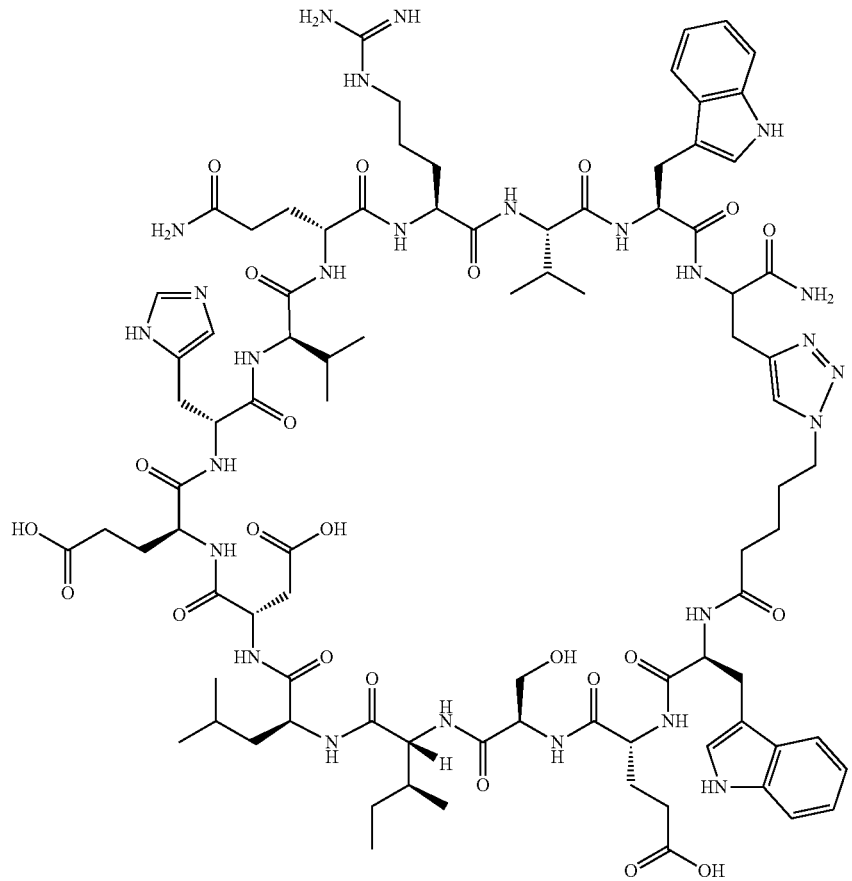
Peptide 33: cyclo-N3*-WESILDEHVQRVW-Pra*-CONH2
(SEQ ID NO: 148)
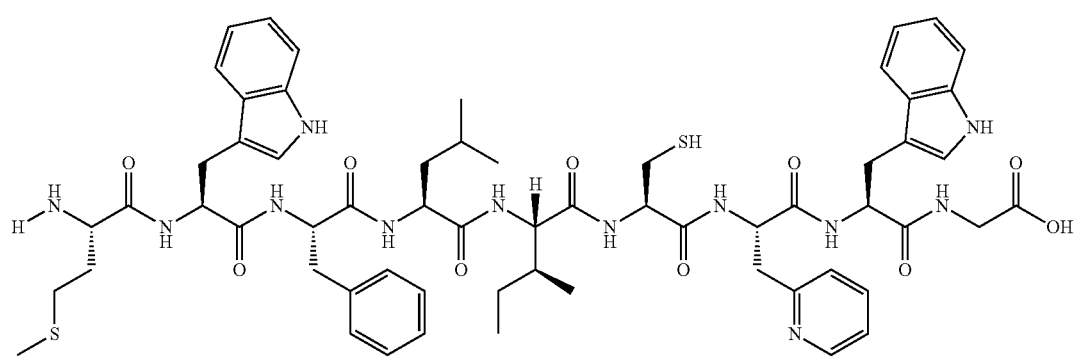
Peptide 148: H2N-MWFLICA(2-Pyr)WG-COOH -continued
(SEQ ID NO: 190)
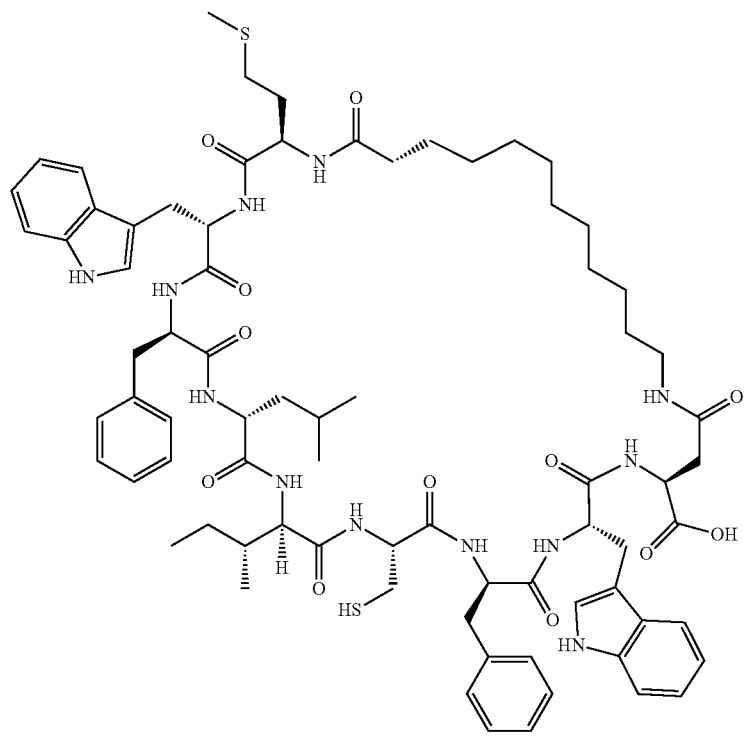
Peptide 190: cyclo-Ado*-MWFLICFWD*-COOH
(SEQ ID NO: 193)
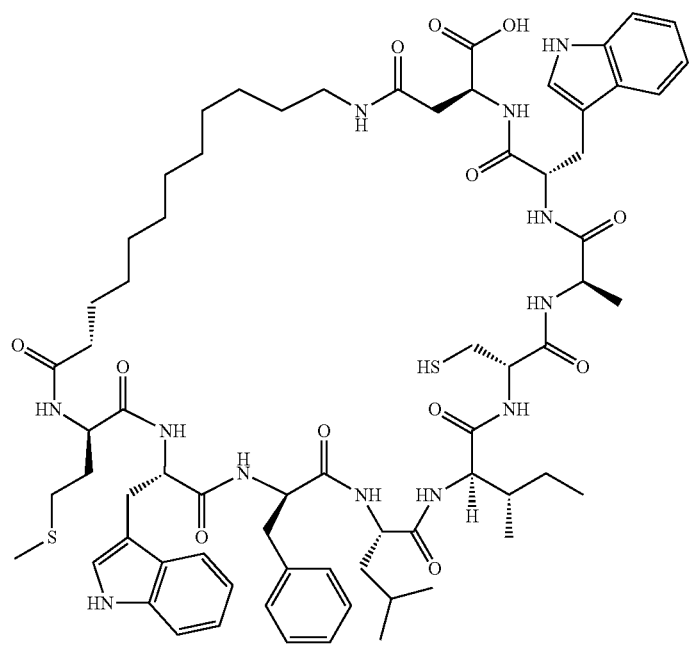
Peptide 193: cyclo-Ado*-MWFLICAWD*-COOH (SEQ ID NO: 224)
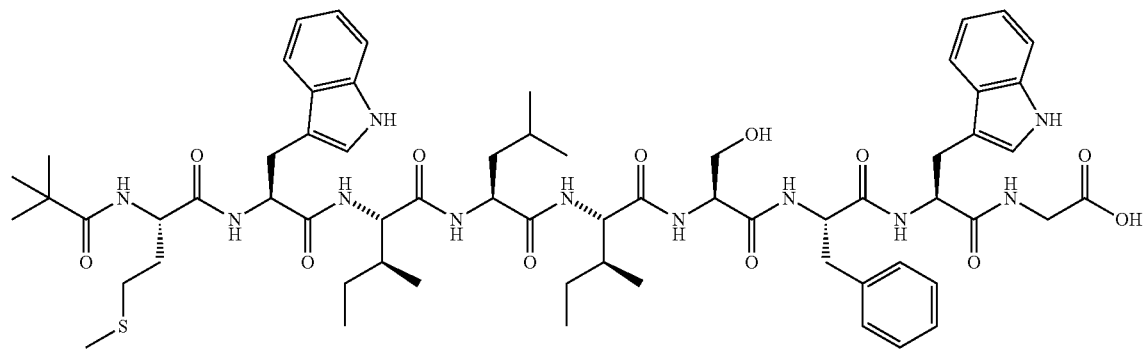
Peptide 224: (Ppa-MWILISFWG-COOH
(SEQ ID NO: 264)
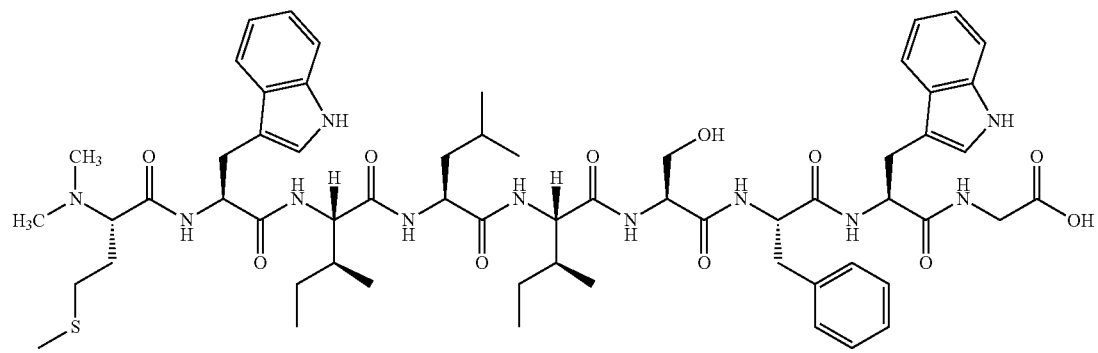
Peptide 264: Me2N-MWILISFWG-COOH
(SEQ ID NO: 144)
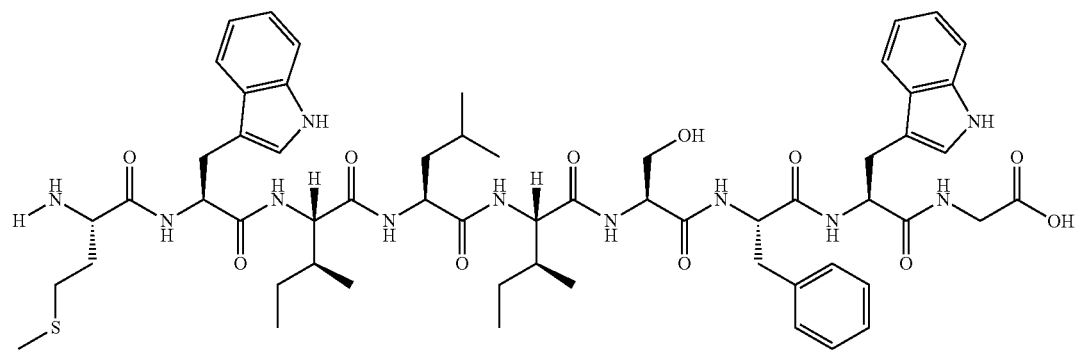
Peptide 144: H2N-MWILI-hS-FWG-COOH (SEQ ID NO: 242)
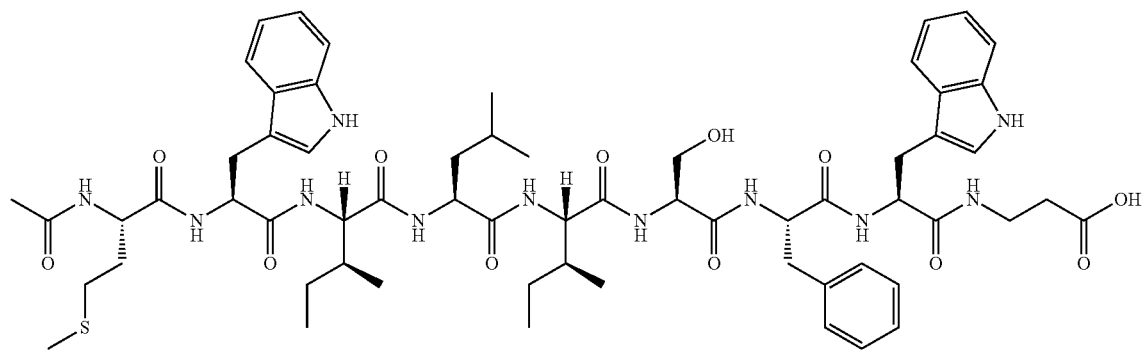
Peptide 242: Ac-MWILISFW-Aβ-COOH
(SEQ ID NO: 234)
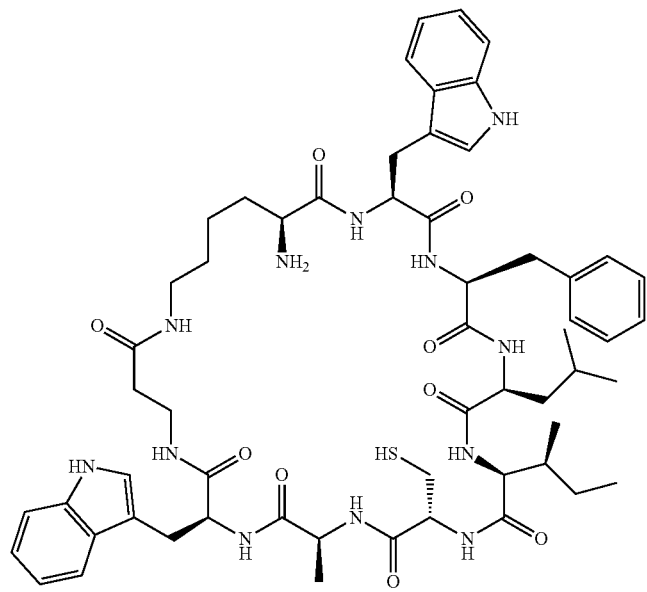
Peptide 234: cyclo-H2N-K*WFLICAW-Aβ*
(SEQ ID NO: 235)
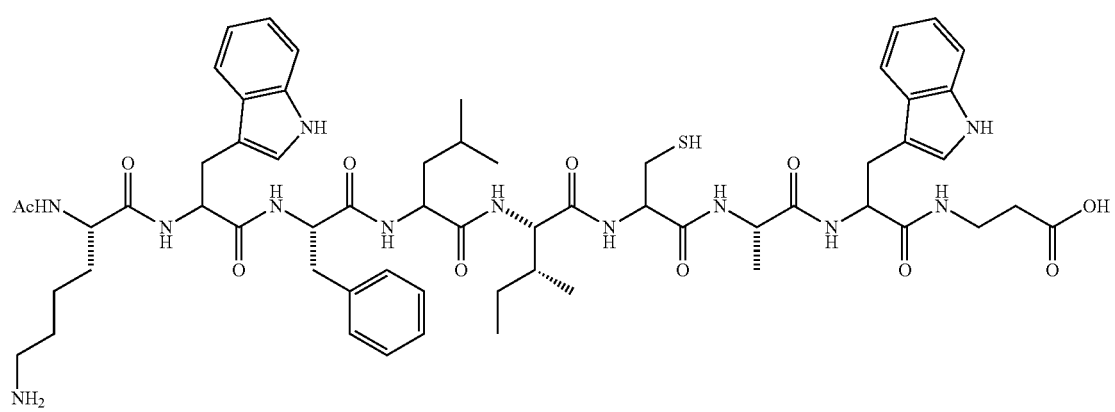
Peptide 235: Ac-KWFLICAW-Aβ

-continued

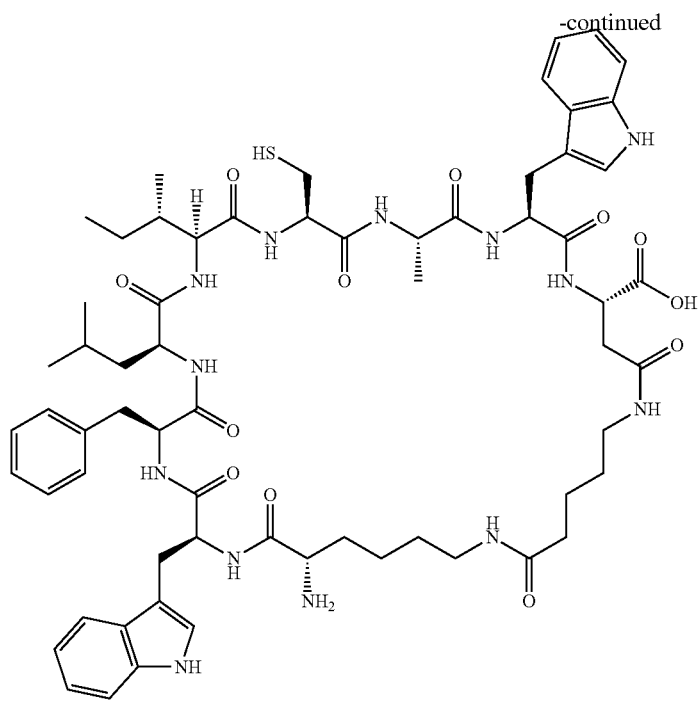

Peptide 248: cyclo-H2N-K(Ava*)WFLICAWD*-COOH( (SEQ ID NO: 249)

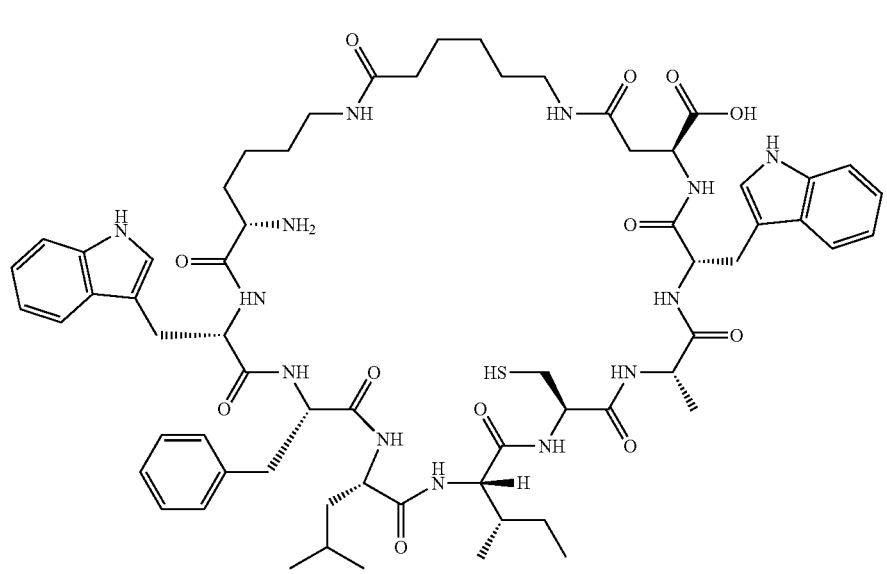

Peptide 249: cyclo-H2N-K(Ahx*)WFLICAWD*-COOH

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

TABLE 4

SEQUENCES

| SEQ ID NO | Family | Sequence |
|---|---|---|
| 1 | 2 | My-GW-NMeW-ESILDEHVQRVWG-COOH |
| 2 | 2 | St-GW-NMeW-ESILDEHVQRVWG-COOH |
| 3 | 3 | cyclo-glutaryl-*MM-NMeNva-QSLF-NMeNva-PP-NMeNva-K*-CONH2 |
| 4 | 3 | cyclo-glutaryl-*MM-NMeNva-QSLF-NMeNva-PP-NMeNva-K*-CONH2 |
| 5 | 4 | cyclo-glutaryl-*MW-NMeNva-WLSRQWIVK*-CONH2 |
| 6 | 1 | H2N-MSRMWFLISFWK-CONH2 |
| 7 | 1 | H2N-MWFLISFWA-COOH |
| 8 | 1 | H2N-MWFLISFAG-COOH |
| 9 | 1 | H2N-MWFLISAWG-COOH |
| 10 | 1 | H2N-MWFLIAFWG-COOH |
| 11 | 1 | H2N-MWFLASFWG-COOH |
| 12 | 1 | H2N-MWFAISFWG-COOH |
| 13 | 1 | H2N-MWALISFWG-COOH |
| 14 | 1 | H2N-MSRMWFLISFWMG-COOH |
| 15 | 1 | H2N-MIRMWFLISFWG-COOH |
| 16 | 1 | H2N-MSRMWFLISFW-NmeA-G-COOH |
| 17 | 1 | H2N-MWFLISFWG-COOH |
| 18 | 2 | cyclo-H2N-K*-NmeA-ESILDEHVQRVWG* |
| 19 | 2 | cyclo-H2N-K*-NmeA-QSILDEHVQRVWG* |
| 20 | 2 | cyclo-H2N-K*W-NMeA-QSILNQHVQRVWG* |
| 21 | 1 | cyclo-H2N-K(Aoc*)MIRM-NmeW-FLISFWG* |
| 22 | 2 | H2N-MWESILDEHVQRVWG-COOH |
| 23 | 2 | H2N-MWESILDEHMQRVWRG-COOH |
| 24 | 1 | cyclo-H2N-K*MSRMWFLISFWRG* |
| 25 | 1 | cyclo-H2N-K*MSRMWLLISFWG* |
| 26 | 1 | cyclo-H2N-K*MWFLISFWG* |
| 27 | 1 | cyclo-H2N-K*MSRMWYLISFWG* |
| 28 | 1 | cyclo-H2N-K*MSRMWFLISLWG* |
| 29 | 3 | cyclo-H2N-K*MPL-NmeA-ISWFEHIG* |
| 30 | 2 | cyclo-H2N-K*M-NmeA-ESILDEHVQRVWG* |
| 31 | 1 | cyclo-H2N-K*MSRMWYLISFW* |
| 32 | 1 | cyclo-H2N-K*SRMWYLISFW* |
| 33 | 2 | cyclo-N3*-WESILDEHVQRVW-Pra*-CONH2 |
| 34 | 2 | H2N-MWESILDEH-aMeV-QRVWG-CONH2 |
| 35 | 2 | H2N-MWE-aMeS-ILDEHVQRVWG-CONH2 |
| 36 | 2 | H2N-W-NmeW-ESILDEHVQRVWG-CONH2 |
| 37 | 2 | H2N-NmeW-NmeW-ESILDEHVQRVWG-CONH2 |
| 38 | 2 | H2N-W-NmeW-E-aMeS-ILDEH-aMeV-QRVWG-CONH2 |

TABLE 4-continued

SEQUENCES

| SEQ ID NO | Family | Sequence |
|---|---|---|
| 39 | 2 | H2N-W-NmeW-ESILDEH-aMeV-QRVWG-CONH2 |
| 40 | 2 | H2N-W-NmeW-E-aMeS-ILDEHVQRVWG-CONH2 |
| 41 | 1 | H2N-MSRMWFLISFWG-COOH |
| 42 | 1 | H2N-MWFLICFWG-COOH |
| 43 | 1 | H2N-MWILISFWG-COOH |
| 44 | 1 | H2N-MSRMWFLISFWTG-COOH |
| 45 | 1 | H2N-MWFLISFW-NmeA-G-COOH |
| 46 | 1 | H2N-MSRMWFLICFWG-COOH |
| 47 | 1 | H2N-MWFLISFWEG-COOH |
| 48 | 1 | H2N-MSRTWFLISFWG-COOH |
| 49 | 1 | H2N-MWFLISFWRG-COOH |
| 50 | 1 | H2N-MSRM-NmeA-FLISFWG-COOH |
| 51 | 1 | H2N-MSRMWILISFWG-COOH |
| 52 | 1 | H2N-MSRMLFLISFWG-COOH |
| 53 | 1 | H2N-MIRM-NmeW-FLISFWG-COOH |
| 54 | 1 | H2N-MSRMWFLISSWG-COOH |
| 55 | 1 | H2N-MSRIWFLISFWG-COOH |
| 56 | 1 | H2N-MSRMWFLVSFWG-COOH |
| 57 | 1 | H2N-MSRMWFLISFWEG-COOH |
| 58 | 1 | H2N-MSRMWFLISFWRG-COOH |
| 59 | 1 | H2N-MSRKWFLISFWG-COOH |
| 60 | 1 | H2N-MSRMWLLISFWG-COOH |
| 61 | 1 | H2N-MNRMWFLISFWG-COOH |
| 62 | 1 | H2N-MSRMWFLTSFWG-COOH |
| 63 | 1 | H2N-MSRMWFLFSFWG-COOH |
| 64 | 1 | H2N-MSRVWFLISFWG-COOH |
| 65 | 1 | H2N-MSRMWFPISFWG-COOH |
| 66 | 1 | H2N-MSRMWYLISFWG-COOH |
| 67 | 1 | H2N-MGRMWFLISFWG-COOH |
| 68 | 1 | H2N-MSRMWFLISLWG-COOH |
| 69 | 1 | H2N-MSRMWFLISFRG-COOH |
| 70 | 1 | H2N-MSRMWFLNSFWG-COOH |
| 71 | 1 | cyclo-H2N-K*MWILISFWG* |
| 72 | 1 | H2N-MSRMWFLISFW-CONH2 |
| 73 | 1 | H2N-MTRMWFLISFW-CONH2 |
| 74 | 1 | H2N-MQRMWFLISFW-CONH2 |
| 75 | 1 | H2N-MSRRWFLISFW-CONH2 |

TABLE 4-continued

SEQUENCES

| SEQ ID NO | Family | Sequence |
|---|---|---|
| 76 | 1 | H2N-MSRTWFLISFW-CONH2 |
| 77 | 1 | H2N-MSRFWFLISFW-CONH2 |
| 78 | 1 | H2N-MSRWWFLISFW-CONH2 |
| 79 | 1 | H2N-WSRMWFLISFW-CONH2 |
| 80 | 1 | H2N-MSRMWWLISFW-CONH2 |
| 81 | 1 | H2N-FSRMWFLISFW-CONH2 |
| 82 | 1 | H2N-YSRMWFLISFW-CONH2 |
| 83 | 1 | H2N-KSRMWFLISFW-CONH2 |
| 84 | 1 | H2N-RSRMWFLISFW-CONH2 |
| 85 | 1 | H2N-DSRMWFLISFW-CONH2 |
| 86 | 1 | H2N-ESRMWFLISFW-CONH2 |
| 87 | 1 | H2N-MSRKWFLISFW-CONH2 |
| 88 | 1 | H2N-MSRHWFLISFW-CONH2 |
| 89 | 1 | H2N-HSRMWFLISFW-CONH2 |
| 90 | 1 | H2N-WSRKWFLISFW-CONH2 |
| 91 | 1 | H2N-WSRHWFLISFW-CONH2 |
| 92 | 1 | H2N-WSRWWFLISFW-CONH2 |
| 93 | 1 | H2N-KSRKWFLISFW-CONH2 |
| 94 | 1 | H2N-KSRHWFLISFW-CONH2 |
| 95 | 1 | H2N-KSRWWFLISFW-CONH2 |
| 96 | 1 | H2N-MWFLISSW-COOH |
| 97 | 1 | H2N-WFLISSW-COOH |
| 98 | 1 | H2N-WFLISFW-CONH2 |
| 99 | 1 | H2N-MSRMWFLISSW-COOH |
| 100 | 1 | H2N-WFLITTW-COOH |
| 101 | 1 | H2N-WFLISS(Bzl)W-COOH |
| 102 | 1 | H2N-NmeW-FLISFW-CONH2 |
| 103 | 1 | H2N-WFLISTW-COOH |
| 104 | 1 | H2N-WFLISS(Et)W-COOH |
| 105 | 1 | H2N-MSRMWFLISS(Et)W-COOH |
| 106 | 1 | H2N-MSRMWFLISS(Bzl)W-COOH |
| 107 | 1 | H2N-MWFLISFW-CONH2 |
| 108 | 1 | H2N-MWFLISFWG-CONH2 |
| 109 | 1 | H2N-WFLISYW-COOH |
| 110 | 1 | H2N-WFLISFW-COOH |
| 111 | 1 | H2N-NmeW-FLISFW-COOH |
| 112 | 1 | H2N-MWFLISFW-COOH |
| 113 | 1 | H2N-KMWILICFWG-COOH |

TABLE 4-continued

SEQUENCES

| SEQ ID NO | Family | Sequence |
|---|---|---|
| 114 | 1 | H2N-HMWILICFWG-COOH |
| 115 | 1 | H2N-RMWILICFWG-COOH |
| 116 | 1 | H2N-MWILICFWG-COOH |
| 117 | 1 | H2N-KWILICFWG-COOH |
| 118 | 1 | H2N-HWILICFWG-COOH |
| 119 | 1 | H2N-RWILICFWG-COOH |
| 120 | 1 | cyclo-H2N-K*WILICFWD*-COOH |
| 121 | 1 | H2N-MWILIC-aMeF-WG-COOH |
| 122 | 1 | H2N-KMWILISFWG-COOH |
| 123 | 1 | H2N-HMWILISFWG-COOH |
| 124 | 1 | H2N-RMWILISFWG-COOH |
| 125 | 1 | H2N-KWILISFWG-COOH |
| 126 | 1 | H2N-HWILISFWG-COOH |
| 127 | 1 | H2N-WWILISFWG-COOH |
| 128 | 1 | H2N-MWILIS-aMeF-WG-COOH |
| 129 | 1 | H2N-MWILISSWG-COOH |
| 130 | 1 | H2N-MWI-aMeL-ICFWG-COOH |
| 131 | 1 | H2N-MW-aMeF-LICFWG-COOH |
| 132 | 1 | H2N-M-aMeW-ILICFWG-COOH |
| 133 | 1 | H2N-MW-aMeF-LISFWG-COOH |
| 134 | 1 | H2N-M-aMeW-ILISFWG-COOH |
| 135 | 1 | H2N-MWFLICH(3-Me)WG-COOH |
| 136 | 1 | H2N-MWILI-aMeS-FWG-COOH |
| 137 | 1 | H2N-MWILI-dT-FWG-COOH |
| 138 | 1 | H2N-MWI-aMeL-ISFWG-COOH |
| 139 | 1 | H2N-2Aoc-WFLICFWG-COOH |
| 140 | 1 | H2N-MWFLICH(1-Me)WG-COOH |
| 141 | 1 | H2N-Nva-WFLICFWG-COOH |
| 142 | 1 | H2N-DWFLICFWG-COOH |
| 143 | 1 | H2N-MWFLIQFWG-COOH |
| 144 | 1 | H2N-MWILI-hS-FWG-COOH |
| 145 | 1 | H2N-MWFLICHWG-COOH |
| 146 | 1 | H2N-MWILIS(Bzl)FWG-COOH |
| 147 | 1 | cyclo-GABA*-MWFLICFWD*-COOH |
| 148 | 1 | H2N-MWFLICA(2-Pyr)WG-COOH |
| 149 | 1 | H2N-MWFLIQFYG-COOH |
| 150 | 1 | H2N-MWILITFWG-COOH |

TABLE 4-continued

SEQUENCES

| SEQ ID NO | Family | Sequence |
|---|---|---|
| 151 | 1 | H2N-MWFLIKFYG-COOH |
| 152 | 1 | H2N-MWILISYWG-COOH |
| 153 | 1 | H2N-MWFLICFW-GABA-COOH |
| 154 | 1 | H2N-MWFLICFWG-COOH |
| 155 | 1 | H2N-MWILISFWG-COOH |
| 156 | 1 | H2N-MWALISFWG-COOH |
| 157 | 1 | H2N-MWFAISFWG-COOH |
| 158 | 1 | H2N-MWFLASFWG-COOH |
| 159 | 1 | H2N-MWFLIAFWG-COOH |
| 160 | 1 | H2N-MWFLISAWG-COOH |
| 161 | 1 | H2N-MWFLISFAG-COOH |
| 162 | 1 | H2N-MWFLISFWA-COOH |
| 163 | 1 | H2N-MWFLIHFWG-COOH |
| 164 | 1 | H2N-Nle-WFLICFWG-COOH |
| 165 | 1 | Ac-MWILISFWG-COOH |
| 166 | 1 | H2N-MIRMWFLICAWG-COOH |
| 167 | 1 | cyclo-H2N-K*MWFLICAWD*-COOH |
| 168 | 1 | cyclo-H2N-K*WFLICAWD*-COOH |
| 169 | 1 | cyclo-Ac-K*WFLICAWD*-COOH |
| 170 | 1 | cyclo-H2N-K*MWFLICFWD*-COOH |
| 171 | 1 | cyclo-H2N-K*MWFLISFWD*-COOH |
| 172 | 1 | cyclo-H2N-K*WFLICFWD*-COOH |
| 173 | 1 | cyclo-H2N-K*WFLICE*WG-COOH |
| 174 | 1 | cyclo-H2N-K(G*)WFLICFWE*G-COOH |
| 175 | 1 | cyclo-Ac-D*WFLICFWK*G-COOH |
| 176 | 1 | cyclo-H2N-D*WFLICFWK*G-COOH |
| 177 | 1 | cyclo-H2N-D*MWFLICFWK*G-COOH |
| 178 | 1 | cyclo-H2N-D*WFLICAWK*G-COOH |
| 179 | 1 | cyclo-H2N-K*WFLICFWE*-COOH |
| 180 | 1 | cyclo-H2N-K*MWFLICE*WG-COOH |
| 181 | 1 | cyclo-H2N-K*WFLICE*WG-COOH |
| 182 | 1 | cyclo-H2N-K*WILISFWE*-COOH |
| 183 | 1 | cyclo-H2N-K*WFLISAWE*-COOH |
| 184 | 1 | cyclo-H2N-K*WILISAWE*-COOH |
| 185 | 1 | cyclo-Ac-K*WFLICFWE*-COOH |
| 186 | 1 | cyclo-Ac-K*MWFLICFWE*-COOH |
| 187 | 1 | cyclo-Ac-K*WFLISAWE*-COOH |
| 188 | 1 | cyclo-Ac-K*WILISAWE*-COOH |

TABLE 4-continued

SEQUENCES

| SEQ ID NO | Family | Sequence |
|---|---|---|
| 189 | 1 | cyclo-Ahx*-MWFLICFWD*-COOH |
| 190 | 1 | cyclo-Ado*-MWFLICFWD*-COOH |
| 191 | 1 | cyclo-GABA*-MWFLICAWD*-COOH |
| 192 | 1 | cyclo-Ahx*-MWFLICAWD*-COOH |
| 193 | 1 | cyclo-Ado*-MWFLICAWD*-COOH |
| 194 | 1 | Ac-WFLICFWG-COOH |
| 195 | 1 | Ac-WILISFWG-COOH |
| 196 | 1 | Ac-WFLIAFWG-COOH |
| 197 | 1 | Ac-MWFLICFW-GABA-COOH |
| 198 | 1 | Ac-MWFLICFWG-COOH |
| 199 | 1 | cyclo-Ac-K*WFLISFWE*-COOH |
| 200 | 1 | cyclo-Ac-K*WFLIAFWE*-COOH |
| 201 | 1 | cyclo-H2N-K*WFLIAFWE*-COOH |
| 202 | 1 | cyclo-H2N-K*WFLISAWD*-COOH |
| 203 | 1 | cyclo-H2N-K*W-Cha-LISAWD*-COOH |
| 204 | 1 | cyclo-H2N-K*W-Chg-LISAWD*-COOH |
| 205 | 1 | cyclo-H2N-K*W-Tle-LISAWD*-COOH |
| 206 | 1 | cyclo-H2N-K*WLLISAWD*-COOH |
| 207 | 1 | cyclo-H2N-K(G*)WFLICAWD*-COOH |
| 208 | 1 | cyclo-H2N-K*WFE*ISFWG-COOH |
| 209 | 1 | H2N-AWFLISFWG-COOH |
| 210 | 1 | H2N-MAFLISFWG-COOH |
| 211 | 1 | H2N-MWFLICAWG-COOH |
| 212 | 1 | H2N-MWFLIAAWG-COOH |
| 213 | 1 | H2N-MWFLICFW-NmeG-COOH |
| 214 | 1 | H2N-MWFLIC(Me)FWG-COOH |
| 215 | 1 | Cyclo-Ac-K*Nle-W-Cha-LI-Abu-AWD*-COOH |
| 216 | 1 | Ac-MW-Cha-LISFWG-COOH |
| 217 | 1 | Ac-MW-Chg-LISFWG-COOH |
| 218 | 1 | Ac-MWLLISFWG-COOH |
| 219 | 1 | Ac-MWFLISFWG-COOH |
| 220 | 1 | Ac-WFLISFWG-COOH |
| 221 | 1 | Ac-MWILISFW-NmeG-COOH |
| 222 | 1 | Ac-MWILISFWG-OMe |
| 223 | 1 | Bz-MWILISFWG-COOH |
| 224 | 1 | Ppa-MWILISFWG-COOH |
| 225 | 1 | Piv-MWILISFWG-COOH |

TABLE 4-continued

SEQUENCES

| SEQ ID NO | Family | Sequence |
|---|---|---|
| 226 | 1 | cyclo-H2N-K*WFLISFWE*-COOH |
| 227 | 1 | cyclo-H2N-K*WFLISFE*G-COOH |
| 228 | 1 | cyclo-H2N-K*WFLISE*WG-COOH |
| 229 | 1 | cyclo-H2N-K*WFLIE*FWG-COOH |
| 230 | 1 | cyclo-H2N-MWK*LIE*FWG-COOH |
| 231 | 1 | cyclo-H2N-K*WFLE*SFWG-COOH |
| 232 | 1 | cyclo-H2N-K*WE*LISFWG-COOH |
| 233 | 1 | cyclo-H2N-D*WFLICAWK*-COOH |
| 234 | 1 | cyclo-H2N-K*WFLICAW-Ap* |
| 235 | 1 | Ac-KWFLICAW-A* |
| 236 | 1 | cyclo-H2N-K*WFLICAWD*-CONH2 |
| 237 | 1 | H2N-LISFWG-COOH |
| 238 | 1 | Ac-LISFWG-COOH |
| 239 | 1 | Ac-FLISFWG-COOH |
| 240 | 1 | Ac-MWILISFW-GABA-COOH |
| 241 | 1 | H2N-FLISFWG-COOH |
| 242 | 1 | Ac-MWILISFW-AP-COOH |
| 243 | 1 | cyclo-Ac-K*WFLIAbuAWD*-COOH |
| 244 | 1 | cyclo-H2N-K*WFLIAbuAWD*-COOH |
| 245 | 1 | cyclo-Ahx*-WFLICAWD*-COOH |
| 246 | 1 | cyclo-Ahx*-WFLIAbuAWD*-COOH |
| 247 | 1 | cyclo-H2N-K(GABA*)WFLICAWD*-COOH |
| 248 | 1 | cyclo-H2N-K(Ava*)WFLICAWD*-COOH |
| 249 | 1 | cyclo-H2N-K(Ahx*)WFLICAWD*-COOK |
| 250 | 1 | cyclo-Adc*-WFLICAW* |
| 251 | 1 | cyclo-H2N-K*LIAFWD*-COOH |
| 252 | 1 | cyclo-Ac-K*LIAFWD*-COOH |
| 253 | 1 | cyclo-H2N-K*FLIAFWD*-COOH |
| 254 | 1 | cyclo-Ac-K*FLIAFWD*-COOH |
| 255 | 1 | cyclo-Ac-K*WChaLISAWD*-COOH |
| 256 | 1 | H2N-MWFLI-Ava-WG-COOH |
| 257 | 1 | Ac-MWFLI-Ava-WG-COOH |
| 258 | 1 | H2N-MWFLI-Abu-FW-NmeG-COOH |
| 259 | 1 | Ac-MWFLI-Abu-FW-NmeG-COOH |
| 260 | 1 | cyclo-H2N-K(Ap*)WFLICAWD*-COOH |
| 261 | 1 | cyclo-Ac-K*W-Cha-LI-Abu-AWD*-COOH |
| 262 | 1 | cyclo-Ac-K*W-Chg-LI-Abu-AWD*-COOH |
| 263 | 1 | Ac-WILIAFWG-COOH |

TABLE 4-continued

SEQUENCES

| SEQ ID NO | Family | Sequence |
|---|---|---|
| 264 | 1 | Me2N-MWILISFWG-COOH |
| 265 | 1 | H2N-WILIAFWG-COOH |
| 266 | | H2N-Tcf4(7-51)-K-CONH2 |
| 267 | | H2N-Tcf4(7-51)-K(FITC)-CONH2 |
| 268 | | H2N-E-Cadherin(819-873)-K-CONH2 |
| 269 | | H2N-E-Cadherin(819-873)-K(FITC)-CONH2 |
| 270 | | Ac-Bcl9(347-381)-AβAβK-CONH2 |
| 271 | | Ac-Bcl9(347-381)-AβAβK(FITC)-CONH2 |
| 272 | 1 | cyclo-H2N-K*WFLICFWE*G-COOH |
| 273 | 1 | cyclo-H2N-K(G*)WFLICFWE*G-COOH |
| 274 | 1 | Ac-MWFLIAFWG-COOH |
| 275 | 1 | H2N-RSRHWFLISFW-CONH2 |
| 276 | 1 | H2N-RSRWWFLISFW-CONH2 |
| 277 | 1 | cyclo-H2N-O*SRMWYLISFW* |
| 278 | 1 | cyclo-H2N-K*SRMWFLISFWG* |
| 279 | 1 | cyclo-H2N-K*-Aβ-SRMWFLISFW* |
| 280/491 | 1 | H2N-RKKRRQRRR-Peg2-MWFLICFWG-COOH |
| 281/492 | 1 | H2N-RKKRRQRRR-Peg2-MWILISFWG-COOH |
| 282/493 | 1 | H2N-RKKRRQRRR-Peg2-KW-Cha-LI-Abu-AWD-COOH |
| 283/494 | 1 | cyclo-H2N-PKKKRKV-Peg2-K*W-Cha-LI-Abu-AWD*-COOH |
| 284 | 1 | cyclo-NH2-K*WFLICAW-N(CH2CO2H)*-G |
| 285/495 | 1 | H2N-PKKKRKV-Peg2-MWFLICFWG-COOH |
| 286/496 | 1 | H2N-PKKKRKV-Peg2-MWILISFWG-COOH |
| 287/497 | 1 | H2N-PKKKRKV-Peg1-MWFLICFWG-COOH |
| 288 | 1 | H2N-PKKKRKVGMWFLICFWG-COOH |
| 289/498 | 1 | H2N-PKKKRKV-Peg1-MWILISFWG-COOH |
| 290 | 1 | H2N-PKKKRKVGMWILISFWG-COOH |
| 291 | 1 | cyclo-NH2-K*MSRMDYLISFW* |
| 292 | 1 | cyclo-NH2-K*MSRMDELISFW* |
| 293 | 1 | cyclo-NH2-K*DFLIAFWD*-COOH |
| 294 | 1 | cyclo-NH2-K*DELIAFWD*-COOH |
| 295 | 1 | H2N-MDFLISFWG-COOH |
| 296 | 1 | H2N-MDELISFWG-COOH |
| 297 | 1 | H2N-MW-NmeA-WLSRQWIVG-COOH |
| 298 | 2 | H2N-M-NmeA-ESILDEHVQRVWG-COOH |
| 299 | 2 | H2N-MYESILDEHMQRVWG-COOH |
| 300 | 2 | H2N-MPESILDEHVQRVWG-COOH |

TABLE 4-continued

SEQUENCES

| SEQ ID NO | Family | Sequence |
|---|---|---|
| 301 | 2 | H2N-MWESILDEHMQRVWG-COOH |
| 302 | 2 | H2N-MYESILDEHVQRVWGILR-COOH |
| 303 | 2 | H2N-MWESILDEHVQRVWGILR-COOH |
| 304 | 2 | H2N-MYESILDEHVQRVWG-COOH |
| 305 | 2 | H2N-MWESILDEHVKRVWG-COOH |
| 306 | 2 | H2N-MWESILDEHVQRVWG-COOH |
| 307 | 1 | cyclo-H2N-K*MSRMWFLISFWG* |
| 308 | 1 | cyclo-H2N-K*MWFLICFWG* |
| 309 | 1 | cyclo-H2N-K*MSRMWFLISFWTG* |
| 310 | 1 | cyclo-H2N-K*MWFLISFW-NmeA-G* |
| 311 | 1 | cyclo-H2N-K*MSRMWFLICFWG* |
| 312 | 1 | cyclo-H2N-K*MWFLISFWEG* |
| 313 | 1 | cyclo-H2N-K*MSRTWFLISFWG* |
| 314 | 1 | cyclo-H2N-K*MWFLISFWRG* |
| 315 | 1 | cyclo-H2N-K*MSRM-NmeA-FLISFWG* |
| 316 | 1 | cyclo-H2N-K*MSRMWILISFWG* |
| 317 | 1 | cyclo-H2N-K*MSRMWFLISFWMG* |
| 318 | 1 | cyclo-H2N-K*MSRMLFLISFWG* |
| 319 | 1 | cyclo-H2N-K*MIRMWFLISFWG* |
| 320 | 1 | cyclo-H2N-K*MSRMWFLISSWG* |
| 321 | 1 | cyclo-H2N-K*MSRMWFLISFW-NmeA-G* |
| 322 | 1 | cyclo-H2N-K*MSRIWFLISFWG* |
| 323 | 1 | cyclo-H2N-K*MSRMWFLVSFWG* |
| 324 | 1 | cyclo-H2N-K*MSRMWFLISFWEG* |
| 325 | 1 | cyclo-H2N-K*MSRKWFLISFWG* |
| 326 | 1 | cyclo-H2N-K*MNRMWFLISFWG* |
| 327 | 1 | cyclo-H2N-K*MSRMWFLTSFWG* |
| 328 | 1 | cyclo-H2N-K*MSRMRFLISFWG* |
| 329 | 1 | cyclo-H2N-K*MSRMWFLFSFWG* |
| 330 | 1 | cyclo-H2N-K*MSRVWFLISFWG* |
| 331 | 1 | cyclo-H2N-K*MSRMWFPISFWG* |
| 332 | 1 | cyclo-H2N-K*MGRMWFLISFWG* |
| 333 | 1 | cyclo-H2N-K*MSRMWFLISFRG* |
| 334 | 1 | cyclo-H2N-K*MSRMWFLNSFWG* |
| 335 | 3 | cyclo-H2N-K*MPSFIIVLTVIG* |
| 336 | 3 | cyclo-H2N-K*MPSFIIVLTLIG* |
| 337 | 3 | cyclo-H2N-K*MPSYIIVLTVIG* |
| 338 | 3 | cyclo-H2N-K*MPCFIIVLTVIG* |

TABLE 4-continued

SEQUENCES

| SEQ ID NO | Family | Sequence |
|---|---|---|
| 339 | 3 | cyclo-H2N-K*MPSFVIVLTVIG* |
| 340 | 3 | cyclo-H2N-K*MPSLIIVLTVIG* |
| 341 | 3 | cyclo-H2N-K*MPSFIIVLTVIRG* |
| 342 | 3 | cyclo-H2N-K*MPSFIIVLSVIG* |
| 343 | 3 | cyclo-H2N-K*MPSFIIVLTVIEG* |
| 344 | 3 | cyclo-H2N-K*MPSFIVVLTVIG* |
| 345 | 3 | cyclo-H2N-K*MPSFIIVLTVI-NmeA-G* |
| 346 | 3 | cyclo-H2N-K*MPSSIIVLTVIG* |
| 347 | 3 | cyclo-H2N-K*MWL-NmeA-TSIPTAAG* |
| 348 | 3 | cyclo-H2N-K*MWL-NmeA-TSIPTASG* |
| 349 | 3 | cyclo-H2N-K*MWL-NmeA-TSIPAAAG* |
| 350 | 3 | cyclo-H2N-K*MWL-NmeA-TCIPTAAG* |
| 351 | 3 | cyclo-H2N-K*MWL-NmeA-TSIPTTAG* |
| 352 | 3 | cyclo-H2N-K*MWL-NmeA-TGIPTAAG* |
| 353 | 3 | cyclo-H2N-K*MRL-NmeA-TSIPTAAG* |
| 354 | 3 | cyclo-H2N-K*MPL-NmeA-ISRFEHIG* |
| 355 | 3 | cyclo-H2N-K*MPL-NmeA-ISRFEHLG* |
| 356 | 3 | cyclo-H2N-K*MPL-NmeA-ISKFEHIG* |
| 357 | 3 | cyclo-H2N-K*MPL-NmeA-ISRFEHIEG* |
| 358 | 3 | cyclo-H2N-K*MPL-NmeA-ISRFEHFG* |
| 359 | 3 | cyclo-H2N-K*MPL-NmeA-ISRIEHIG* |
| 360 | 3 | cyclo-H2N-K*MPL-NmeA-ISRFEHIRG* |
| 361 | 3 | cyclo-H2N-K*MPL-NmeA-IRRFEHIG* |
| 362 | 3 | cyclo-H2N-K*MPL-NmeA-NSRFEHIG* |
| 363 | 3 | cyclo-H2N-K*MPL-NmeA-ISRFEHVG* |
| 364 | 3 | cyclo-H2N-K*MPL-NmeA-IGRFEHIG* |
| 365 | 3 | cyclo-H2N-K*MPLQISRFEHIG* |
| 366 | 1 | cyclo-H2N-K*MW-NmeA-WLSRQWIVG* |
| 367 | 2 | cyclo-H2N-K*MYESILDEHMQRVWG* |
| 368 | 2 | cyclo-H2N-K*MPESILDEHVQRVWG* |
| 369 | 2 | cyclo-H2N-K*MWESILDEHMQRVWG* |
| 370 | 2 | cyclo-H2N-K*MYESILDEHVQRVWGILR* |
| 371 | 2 | cyclo-H2N-K*MWESILDEHVQRVWG* |
| 372 | 2 | cyclo-H2N-K*MWESILDEHVQRVWGILR* |
| 373 | 2 | cyclo-H2N-K*MWESILDEHMQRVWRG* |
| 374 | 2 | cyclo-H2N-K*MYESILDEHVQRVWG* |
| 375 | 2 | cyclo-H2N-K*MWESILDEHVKRVWG* |

TABLE 4-continued

SEQUENCES

| SEQ ID NO | Family | Sequence |
|---|---|---|
| 376 | 2 | cyclo-H2N-K*MWESILDEHVQRVWG* |
| 377/499 | 2 | cyclo-Az*-Peg8-WE-aMeS-ILDEH-aMeV-QRVW-Pra-CONH2 |
| 378 | 2 | cyclo-glutaryl*-ML-NmeNva-IDQVSVSRVWK*-CONH2 |
| 379 | 4 | cyclo-glutaryl*-M-NmeNva-RSSQELPVHRVWK*-CONH2 |
| 380 | 3 | cyclo-stearyl-GK*WL-NmeNva-TSIPTAA* |
| 381 | 3 | cyclo-H2N-K*WL-NmeNva-TSIPTAA* |
| 382 | 3 | cyclo-glutaryl*-MWL-NmeNva-TSIPTAAK*-CONH2 |
| 383 | 3 | cyclo-glutaryl*-MPL-NmeNva-ISRFEHIK*-CONH2 |
| 384 | 3 | cyclo-glutaryl*-MPL-NmeNva-ISRFEHIK*-CONH2 |
| 385 | 3 | cyclo-glutaryl*-MPL-NmeNva-ISRFEHIK*-CONH2 |
| 386 | 3 | cyclo-H2N-K*PPWVSPPMTM* |
| 387 | 2 | cyclo-glutaryl*-MM-NmeNva-QSLF-NmeNva-PP-NmeNva-K*-CONH2 |
| 388 | 4 | cyclo-glutaryl*-MW-NmeNva-WLSRQWIVLK*-CONH2 |
| 389 | 1 | cyclo-H2N-K(Aoc*)MIRMWFLISFWG* |
| 390 | 2 | Steaiyl-W-NmeW-E-aMeS-ILDEH-aMeV-QRVWG-COOH |
| 391 | 2 | Stearyl-betaA-W-NmeW-E-aMeS-ILDEH-aMeV-QRVWG-COOH |
| 392 | 2 | Stearyl-GABA-W-NmeW-E-aMeS-ILDEH-aMeV-QRVWG-COOH |
| 393/500 | 2 | *Stearyl-W-NmeW-E-aMeS-ILDEH-aMeV-QRVW-COOH* |
| 394 | 2 | Stearyl-betaA-W-NmeW-E-aMeS-ILDEH-aMeV-QRVW-COOH |
| 395 | 2 | Stearyl-GABA-W-NmeW-E-aMeS-ILDEH-aMeV-QRVW-COOH |
| 396 | 2 | Palmitoyl-W-NmeW-E-aMeS-ILDEH-aMeV-QRVWG-COOH |
| 397 | 2 | Palmitoyl-W-NmeW-E-aMeS-ILDEH-aMeV-QRVW-COOH |
| 398 | 2 | Palmitoyl-GW-NmeW-E-aMeS-ILDEH-aMeV-QRVW-COOH |
| 399 | 2 | Palmitoyl-betaA-W-NmeW-E-aMeS-ILDEH-aMeV-QRVW-COOH |
| 400 | 2 | Palmitoyl-GABA-W-NmeW-E-aMeS-ILDEH-aMeV-QRVW-COOH |
| 401 | 2 | cyclo-H2N-W-NmeA-QK*ILDE*HVQRVWG-NH2 |
| 402 | 2 | cyclo-AcNH-W-NmeA-QK*ILDE*HVQRVWG-NH2 |
| 403 | 2 | cyclo-H2N-W-NmeA-QK*ILDE*H-Chg-QRVWG-NH2 |
| 404 | 2 | cyclo-AcNH-W-NmeA-QK*ILDE*H-Chg-QRVWG-NH2 |
| 405 | 2 | cyclo-succinyl-NH-W-NmeA-QK*ILDE*H-Chg-QRVWG-NH2 |
| 406 | 2 | cyclo-H2N-W-NmeA-QK*I-Cha-DE*HVQRVWG-NH2 |
| 407 | 2 | cyclo-AcNH-W-NmeA-QK*I-Cha-DE*HVQRVWG-NH2 |
| 408 | 2 | cyclo-PhOCH2C(O)NH-W-NmeA-QK*I-Cha-DE*HVQRVWG-NH2 |
| 409 | 2 | cyclo-C8H15C(O)NH-W-NmeA-QK*I-Cha-DE*HVQRVWG-NH2 |
| 410 | 2 | H2N-BAla-RLPESILDEHVQRVWP-NH2 |
| 411 | 2 | AcNH-BAla-RLPESILDEHWQRVWP-NH2 |
| 412 | 2 | AcNH-BAla-EEDPQTILDDHLSRVLK-NH2 |
| 413 | 2 | Ac-BAla-RLPESILDEHVQRVWP-NH2 |

TABLE 4-continued

SEQUENCES

| SEQ ID NO | Family | Sequence |
|---|---|---|
| 414 | 2 | AcNH-W-NMeA-QK*ILDE*H-Chg-Aib-RVWG-NH2 |
| 415 | 2 | H2N-W-NMeA-QK*ILDE*H-Chg-SRVWG-NH2 |
| 416 | 2 | AcNH-W-NMeA-QK*ILDE*H-Chg-SRVWG-NH2 |
| 417 | 2 | H2N-W-NMeA-Aib-K*ILDE*H-Chg-QRVWG-NH2 |
| 418 | 2 | AcNH-W-NMeA-Aib-K*ILDE*H-Chg-QRVWG-NH2 |
| 419 | 2 | AcNH-βA-W-NMeA-QK*ILDE*H-Chg-QRVWG-NH2 |
| 420 | 2 | H2N-W-NMeA-QK*-Chg-LDE*HVQRVWG-NH2 |
| 421 | 2 | AcNH-W-NMeA-QK*-Chg-LDE*HVQRVWG-NH2 |
| 422 | 2 | H17C8C(O)NH-W-NMeA-QK*-Chg-LDE*HVQRVWG-NH2 |
| 423 | 2 | H2N-W-NMeA-QO*ILDE*H-Chg-QRVWG-NH2 |
| 424 | 2 | AcNH-W-NMeA-QO*ILDE*H-Chg-QRVWG-NH2 |
| 425 | 2 | H17C8C(O)NH-W-NMeA-QO*ILDE*H-Chg-QRVWG-NH2 |
| 426 | 2 | AcNH-W-NMeA-QE*ILDK*H-Chg-QRVWG-NH2 |
| 427 | 2 | H17C8C(O)NH-W-NMeA-QE*ILDK*H-Chg-QRVWG-NH2 |
| 428 | 2 | AcNH-RWPQK*ILDE*HVRRVWR-NH2 |
| 429 | 2 | AcNH-RRWPQK*ILDE*HVRRVWR-NH2 |
| 430 | 2 | AcNH-W-NMeA-QK*ILDD*H-Chg-QRVWG-NH2 |
| 431 | 2 | H17C8C(O)NH-W-NMeA-QK*ILDD*H-Chg-QRVWG-NH2 |
| 432 | 2 | H23CHC(O)NH-W-NMeA-QK*ILDD*H-Chg-QRVWG-NH2 |
| 433 | 2 | AcNH-NMeA-QK*ILNE*H-Chg-QRVWG-NH2 |
| 434 | 2 | H23CHC(O)NH-NMeA-QK*ILNE*H-Chg-QRVWG-NH2 |
| 435 | 2 | AcNH-W-NMeA-QK*ILNE*H-Chg-QRVWG-NH2 |
| 436 | 2 | H23C11C(O)NH-W-NMeA-QK*ILNE*H-Chg-QRVWG-NH2 |
| 437 | 2 | AcNH-W-NmeA-QSILDE*HVQK*VWG-NH2 |
| 438 | 2 | H17C8C(O)NH-W-NmeA-QSILDE*HVQK*VWG-NH2 |
| 439 | 2 | H23CHC(O)NH-W-NmeA-QSILDE*HVQK*VWG-NH2 |
| 440 | 2 | AcNH-QK*ILDE*H-Chg-QRVWG-NH2 |
| 441 | 2 | AcNH-WAQK*ILDE*H-Chg-QRVWG-NH2 |
| 442 | 2 | AcNH-W-Pip-QK*ILDE*H-Chg-QRVWG-NH2 |
| 443 | 2 | AcNH-W-Aib-QK*ILDE*H-Chg-QRVWG-NH2 |
| 444 | 2 | H23C11C(O)NH-EDPQK*ILDE*HLQRVLK-NH2 |
| 445 | 2 | AcNH-NMeA-QK*ILDE*H-Chg-QRVW-NH2 |
| 446 | 2 | AcNH-W-NMeA-QK*ILDE*H-Chg-QRVW-NH2 |
| 447 | 2 | H23CHC(O)NH-W-NMeA-QK*ILDE*H-Chg-QRVW-NH2 |
| 448 | 2 | AcNH-NMeA-QK*ILDE*H-Chg-QRVWR-NH2 |
| 449 | 2 | AcNH-W-NMeA-QK*ILDE*H-Chg-QRVWR-NH2 |
| 450 | 2 | AcNH-W-NMeA-E*SILK*EHVQRVWG-NH2 |

TABLE 4-continued

SEQUENCES

| SEQ ID NO | Family | Sequence |
|---|---|---|
| 451 | 2 | H23C11C(O)NH-W-NMeA-E*SILK*EHVQRVWG-NH2 |
| 452 | 2 | Ac-NH-W-NMeA-QK*ILND*H-Chg-QAV-NH2 |
| 453 | 2 | Lauroyl-NH-W-NMeA-QK*ILND*H-Chg-QAV-NH2 |
| 454 | 2 | Palmitoyl-NH-W-NMeA-QK*ILND*H-Chg-QAV-NH2 |
| 455 | 2 | Ac-NH-W-Aib-QK*ILND*H-Chg-QRVW-NH2 |
| 456 | 2 | Lauroyl-NH-W-Aib-QK*ILND*H-Chg-QRVW-NH2 |
| 457 | 2 | biotin-PEG2-NMeA-QK*ILDD*H-Chg-QRVWG-NH2 |
| 458 | 2 | Ac-NH-W-NMeA-QK*ILND*H-Chg-QAVW-NH2 |
| 459 | 2 | Lauroyl-NH-W-NMeA-QK*ILND*H-Chg-QAVW-NH2 |
| 460 | 2 | Ac-NH-W-NMeA-QSILDK*H-Chg-QD*VW-NH2 |
| 461 | 2 | Lauroyl-NH-W-NMeA-QSILDK*H-Chg-QD*VW-NH2 |
| 462 | 2 | Ac-NH-WPQSILDK*H-Chg-QD*VW-NH2 |
| 463 | 2 | Lauroyl-NH-WPQSILDK*H-Chg-QD*VW-NH2 |
| 464 | 2 | Ac-NH-W-NMeA-QK*ILDE*H-Chg-E*DVWK*-NH2 |
| 465 | 2 | Lauroyl-NH-W-NMeA-QK*ILDE*H-Chg-E*DVWK*-NH2 |
| 466 | 2 | Ac-NH-W-NMeA-QSILDE*H-Chg-QK*VW-NH2 |
| 467 | 2 | Lauroyl-NH-W-NMeA-QSILDE*H-Chg-QK*VW-NH2 |
| 468 | 2 | Ac-NH-WPQSILDE*H-Chg-QK*VW-NH2 |
| 469 | 2 | Lauroyl-NH-WPQSILDE*H-Chg-QK*VW-NH2 |
| 470 | 2 | Ac-NH-W-NMeA-QSILDE*H-Chg-QK*VWG-NH2 |
| 471 | 2 | Lauroyl-NH-W-NMeA-QSILDE*H-Chg-QK*VWG-NH2 |
| 472 | 2 | Ac-NH-WPQSILDE*H-Chg-QK*VWG-NH2 |
| 473 | 2 | Lauroyl-NH-WPQSILDE*H-Chg-QK*VWG-NH2 |
| 474 | | Palmitoyl-GW-NmeW-E-aMeS-ILDEH-aMeV-QRVW-COOH |
| 475 | | Ac-βA-ENPESILDEHVQRVMR |
| 476 | | Acetyl-NH-W-NMeA-QK*ILDE*H-Chg-E*AVWK* |
| 477 | | H23CHC(O)-NH-W-NMeA-QK*ILDE*H-Chg-E*AVWK* |
| 478 | | H23C11C(O)-W-NMeA-QK*ILDE*H-Chg-QRVWR-NH2 |
| 479 | | Ac-NMeA-Aib-K*ILDD*H-Chg-QRVW-NH2 |
| 480 | | H23C11C(O)-NMeA-Aib-K*ILDD*H-Chg-QRVW-NH2 |
| 481 | | H23CHC(O)-W-NMeA-Aib-K*ILDD*H-Chg-QRVW-NH2 |
| 482 | | Ac-NMeA-QD*ILDK*H-Chg-QRVWG-NH2 |
| 483 | | Ac-W-NmeA-QD*ILDK*H-Chg-QRVWG-NH2 |
| 484 | | H23CHC(O)-W-NMeA-QD*ILDK*H-Chg-QRVWG-NH2 |
| 485 | | Ac-PQK*ILDE*HVQRVMK-NH2 |
| 486 | | H23C11C(O)-PQK*ILDE*HVQRVMK-NH2 |
| 487 | | H31C15C(O)-PQK*ILDE*HVQRVMK-NH2 |
| 488 | | Ac-PQK*ILDE*H-Chg-QRVMK-NH2 |

TABLE 4-continued

SEQUENCES

| SEQ ID NO | Family | Sequence |
|---|---|---|
| 489 | | H23C11C(O)-PQK*ILDE*H-Chg-QRVMK-NH2 |
| 490 | | H31C15C(O)-PQK*ILDE*H-Chg-QRVMK-NH2<br>R-$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$<br>R-$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$ |

TABLE 5

Characterization

| | Surface | | | | | Proliferation | |
| | | | Plasmon Resonance (Biacore ®) | Wnt Reporter | | % Viability non-Wnt | Wnt dependent cells | Endo cells |
| | β-Cat FP | | | | | | | |
| SEQ ID NO. | $K_D$ (nM) | Hill slope | $K_D$ (nM) | $EC_{50}$ (uM) | Hill Slope | responsive cells | $IC_{50}$ (uM) | $IC_{50}$ (uM) |
|---|---|---|---|---|---|---|---|---|
| 1 | A | 0.8 | | | | | 18.5 | |
| 2 | A | 0.82 | | | | | | |
| 3 | D | 0.98 | | | | | | |
| 4 | E | 0.4 | | | | | | |
| 5 | C | 0.5 | | | | | | |
| 6 | E | ND | | | | | | |
| 7 | D | 0.5 | | | | | | |
| 8 | C | 1.7 | | | | | | |
| 9 | C | 0.51 | | | | | | |
| 10 | C | 0.73 | | | | | | |
| 11 | B | 1.31 | | | | | | |
| 12 | C | 0.5 | | | | | | |
| 13 | B | 0.86 | | | | | | |
| 14 | E | | 250 | | F | 98 | | |
| 15 | | | 130 | | F | 103 | | |
| 16 | E | | 120 | | H | 92 | | |
| 17 | B | 1.66 | 314 | | F | 98 | | |
| 18 | E | | 76 | | J | 90.16 | | |
| 19 | E | | 59 | | J | 104.41 | | |
| 20 | E | | 48 | | J | 106.38 | | |
| 21 | E | | 337 | | J | 98.73 | | |
| 22 | | | 1370 | | J | 99.59 | | |
| 23 | A | 0.71 | 1588 | | J | 98.88 | | |
| 24 | A | 1 | 270 | | J | 96.75 | | |
| 25 | | | 112 | | G | 97 | | |
| 26 | | | 110 | | G | 88 | | |
| 27 | | | 515 | | J | 96 | | |
| 28 | | | 803 | | I | 91 | | |
| 29 | B | 1.72 | 1029 | | J | 107.34 | | |
| 30 | C | 0.7 | 123 | | J | 106.28 | | |
| 31 | | | | | J | 89 | | |
| 32 | E | | | | J | 93 | | |
| 33 | E | | | | J | | | |
| 34 | A | 0.92 | | | J | | | |
| 35 | A | 0.96 | | | J | | | |
| 36 | A | 0.87 | | | J | | | |
| 37 | A | 0.7 | | | J | | | |
| 38 | A | 0.9 | | | J | | | |
| 39 | A | 0.89 | | | J | | | |
| 40 | A | 0.88 | | | J | | | |
| 41 | E | ND | | | F | 96.12 | | |
| 42 | A | 0.96 | | | F | 108.69 | | |
| 43 | B | 0.92 | | | F | 98.97 | | |
| 44 | | | | | H | 102.16 | | |
| 45 | B | 0.9 | | | F | 101.07 | | |
| 46 | | | | | F | 100.91 | | |
| 47 | B | 2.29 | | | F | 102.51 | | |
| 48 | E | ND | | | G | 101.09 | | |
| 49 | E | ND | | | F | 102.51 | | |
| 50 | C | 0.76 | | | J | 96.72 | | |
| 51 | | | | | G | 98.53 | | |
| 52 | E | ND | | | H | 87.15 | | |

TABLE 5-continued

| | Characterization ||||||| 
|---|---|---|---|---|---|---|---|
| | Surface |||| Proliferation |||
| | β-Cat FP || Plasmon Resonance (Biacore ®) | Wnt Reporter || % Viability non-Wnt responsive cells | Wnt dependent cells | Endo cells |
| SEQ ID NO. | $K_D$ (nM) | Hill slope | $K_D$ (nM) | $EC_{50}$ (uM) | Hill Slope | | $IC_{50}$ (uM) | $IC_{50}$ (uM) |
| 53 | E | | | J | | 102.92 | | |
| 54 | C | 0.7 | | H | | 98.34 | | |
| 55 | E | ND | | F | | 100.79 | | |
| 56 | E | ND | | G | | 100.49 | | |
| 57 | C | 0.7 | | F | | 103.77 | | |
| 58 | E | ND | | I | | 105.82 | | |
| 59 | E | ND | | J | | 101.95 | | |
| 60 | E | ND | | G | | 101.21 | | |
| 61 | E | ND | | G | | 100.18 | | |
| 62 | E | ND | | J | | 104.21 | | |
| 63 | E | ND | | F | | 97.87 | | |
| 64 | C | 0.7 | | G | | 103.75 | | |
| 65 | C | 0.7 | | J | | 104.54 | | |
| 66 | D | 0.7 | | G | | 98.58 | | |
| 67 | C | 0.99 | | F | | 100.98 | | |
| 68 | E | ND | | G | | 91.24 | | |
| 69 | A | 1.64 | | J | | 99.68 | | |
| 70 | E | | | J | | 98.52 | | |
| 71 | E | | | J | | 93.73 | | |
| 72 | E | ND | | J | | 88.61 | | |
| 73 | E | ND | | J | | 97.26 | | |
| 74 | E | ND | | J | | 91.23 | | |
| 75 | E | ND | | J | | 99.23 | | |
| 76 | E | ND | | J | | 104.63 | | |
| 77 | E | ND | | J | | 106.64 | | |
| 78 | E | ND | | J | | 101.3 | | |
| 79 | E | ND | | J | | 98.85 | | |
| 80 | E | ND | | J | | 101.03 | | |
| 81 | E | ND | | J | | 90.65 | | |
| 82 | E | ND | | J | | 83.97 | | |
| 83 | E | ND | | J | | 90.89 | | |
| 84 | E | ND | | J | | 88.59 | | |
| 85 | E | ND | | J | | 107.37 | | |
| 86 | E | ND | | J | | 103.42 | | |
| 87 | E | ND | | J | | 114.33 | | |
| 88 | E | ND | | J | | 105.08 | | |
| 89 | E | ND | | J | | 106.59 | | |
| 90 | E | ND | | J | | 83.32 | | |
| 91 | E | ND | | J | | 84.62 | | |
| 92 | E | ND | | H | | 87.82 | | |
| 93 | E | ND | | J | | 94.04 | | |
| 94 | E | ND | | J | | 117.59 | | |
| 95 | E | ND | | J | | 108.74 | | |
| 96 | D | 0.7 | | G | | 97.29 | | |
| 97 | C | 2.45 | | I | | 101.82 | | |
| 98 | C | 1.02 | | J | | 95.96 | | |
| 99 | C | 0.7 | | I | | 97.29 | | |
| 100 | C | 2.8 | | G | | 102.3 | | |
| 101 | C | 3 | | G | | 105.89 | | |
| 102 | A | 0.7 | | H | | 101.4 | | |
| 103 | C | 1.71 | | H | | 102.43 | | |
| 104 | C | 3 | | G | | 103.84 | | |
| 105 | C | 0.7 | | G | | 96.82 | | |
| 106 | C | 0.7 | | H | | 105.27 | | |
| 107 | C | 0.7 | | G | | 100.02 | | |
| 108 | B | 0.7 | | G | | 102.19 | | |
| 109 | C | 3 | | G | | 103.29 | | |
| 110 | C | 3 | | G | | 103.21 | | |
| 111 | B | 2.06 | | G | | 99.76 | | |
| 112 | B | 1.82 | | F | | 103.29 | | |
| 113 | C | 0.7 | | J | | 102.5 | | |
| 114 | C | 0.7 | | F | | 123.2 | | |
| 115 | C | 0.7 | | H | | 115.6 | | |
| 116 | B | 0.72 | | F | | 122.7 | | |
| 117 | E | | | H | | 138.3 | | |
| 118 | E | | | F | | 99.9 | | |
| 119 | C | 0.7 | | G | | 143 | | |
| 120 | E | | | F | | 122.7 | | |
| 121 | A | 0.74 | | F | | 150.5 | | |

TABLE 5-continued

| | Characterization | | | | | | | |
|---|---|---|---|---|---|---|---|---|
| | Surface | | | | | Proliferation | | |
| | β-Cat FP | | Plasmon Resonance (Biacore ®) | Wnt Reporter | | % Viability non-Wnt | Wnt dependent cells | Endo cells |
| SEQ ID NO. | $K_D$ (nM) | Hill slope | $K_D$ (nM) | $EC_{50}$ (uM) | Hill Slope | responsive cells | $IC_{50}$ (uM) | $IC_{50}$ (uM) |
| 122 | A | 1.55 | | I | | 113.1 | | |
| 123 | A | 1.07 | | F | | 107.3 | | |
| 124 | E | | | G | | 102.5 | | |
| 125 | B | 0.7 | | I | | 113.1 | | |
| 126 | A | 0.99 | | F | | 110.9 | | |
| 127 | B | 1 | | G | | 119.5 | | |
| 128 | B | 2.15 | | G | | 131.9 | | |
| 129 | B | 0.87 | | F | | 134.3 | | |
| 130 | C | 0.72 | | I | | 98.28 | | |
| 131 | A | 1.27 | | G | | 93.14 | | |
| 132 | A | 0.7 | | G | | 102.36 | | |
| 133 | A | 3 | | J | | 95.4 | | |
| 134 | C | 1.47 | | J | | 97.94 | | |
| 135 | C | 0.7 | | G | | 106.68 | | |
| 136 | B | 0.9 | | J | | 106.12 | | |
| 137 | B | 0.81 | | H | | 93.87 | | |
| 138 | E | | | J | | 106.16 | | |
| 139 | E | | | J | | 99.52 | | |
| 140 | C | 0.7 | | H | | 101.73 | | |
| 141 | E | | | G | | 100.18 | | |
| 142 | A | 1.15 | | F | | 107.74 | | |
| 143 | E | | | G | | 104 | | |
| 144 | E | | | F | | 105.58 | | |
| 145 | C | 0.7 | | G | | 106.53 | | |
| 146 | E | | | J | | 99.14 | | |
| 147 | E | | | J | | 104.63 | | |
| 148 | B | 0.7 | | G | | 95.53 | | |
| 149 | B | 0.75 | | G | | 104.08 | | |
| 150 | E | | | F | | 99.81 | | |
| 151 | B | 0.7 | | H | | 106.91 | | |
| 152 | E | | | F | | 113.57 | | |
| 153 | E | | | F | | 103.83 | | |
| 154 | E | | | H | | 103.02 | | |
| 155 | E | | | J | | 96.98 | | |
| 156 | E | | | F | | 101.65 | | |
| 157 | E | | | F | | 99.91 | | |
| 158 | E | | | G | | 95.57 | | |
| 159 | E | | | F | | 106.56 | | |
| 160 | E | | | F | | 102.03 | | |
| 161 | E | | | H | | 103.41 | | |
| 162 | E | | | G | | 103.98 | | |
| 163 | E | | | F | | 100.5 | | |
| 164 | B | 0.7 | | F | | 100.47 | | |
| 165 | A | 2.99 | | F | | 101.99 | | |
| 166 | E | | | J | | 99.95 | | |
| 167 | C | 0.7 | | G | | 98.81 | | |
| 168 | C | 0.7 | | F | | 99.11 | | |
| 169 | C | 0.7 | | F | | 93.5 | | |
| 170 | C | 0.7 | | H | | 107.31 | | |
| 171 | C | 0.7 | | F | | 79.57 | | |
| 172 | C | 0.7 | | F | | 90.8 | | |
| 173 | C | 0.7 | | J | | 106.79 | | |
| 174 | C | 0.7 | | G | | 101.51 | | |
| 175 | D | 0.7 | | G | | 100.27 | | |
| 176 | D | 0.85 | | G | | 108.71 | | |
| 177 | E | ND | | G | | 98.64 | | |
| 178 | E | | | F | | 91.85 | | |
| 179 | C | 1.01 | | F | | 90.87 | | |
| 180 | E | | | F | | 102.99 | | |
| 181 | B | 1.15 | | J | | 89.16 | | |
| 182 | B | 1.06 | | I | | 95.34 | | |
| 183 | C | 0.7 | | F | | 96.97 | | |
| 184 | D | 0.7 | | F | | 95.25 | | |
| 185 | A | 1.32 | | I | | 87.81 | | |
| 186 | B | 1.07 | | J | | 96.4 | | |
| 187 | C | 0.7 | | G | | 90.26 | | |
| 188 | D | 0.7 | | F | | 97.63 | | |
| 189 | B | 1.69 | | F | | 99.47 | | |
| 190 | B | 1.92 | | F | | 99.61 | | |

TABLE 5-continued

| | Characterization | | | | | | | |
|---|---|---|---|---|---|---|---|---|
| | β-Cat FP | | Surface Plasmon Resonance (Biacore ®) | Wnt Reporter | | Proliferation | | |
| | | | | | | % Viability non-Wnt | Wnt dependent cells | Endo cells |
| SEQ ID NO. | $K_D$ (nM) | Hill slope | $K_D$ (nM) | $EC_{50}$ (uM) | Hill Slope | responsive cells | $IC_{50}$ (uM) | $IC_{50}$ (uM) |
| 191 | B | 1.3 | | G | | 99.06 | | |
| 192 | A | 1.33 | | F | | 102.96 | | |
| 193 | B | 2.34 | | F | | 96.63 | | |
| 194 | B | 3 | | F | | 105.72 | | |
| 195 | A | 3 | | F | | 104.92 | | |
| 196 | B | 2.58 | | F | | 105.28 | | |
| 197 | B | 1.52 | | F | | 89.79 | | |
| 198 | B | 2.18 | | F | | 81.4 | | |
| 199 | B | 0.7 | | F | | 89.79 | | |
| 200 | C | 0.7 | | F | | 81.4 | | |
| 201 | C | 0.7 | | I | | 60.11 | | |
| 202 | E | ND | | I | | 92.13 | | |
| 203 | E | ND | | G | | 97.96 | | |
| 204 | B | 0.74 | | F | | 108.33 | | |
| 205 | E | ND | | J | | 113.87 | | |
| 206 | E | ND | | H | | 98.66 | | |
| 207 | B | 0.7 | | F | | 106.86 | | |
| 208 | C | 0.69 | | G | | 93.36 | | |
| 209 | B | 0.93 | | F | | 90.98 | | |
| 210 | C | 0.6 | | F | | 96.39 | | |
| 211 | C | 0.67 | | F | | 93.86 | | |
| 212 | B | 1.05 | | F | | 99.28 | | |
| 213 | C | 0.7 | | F | | 112.16 | | |
| 214 | B | 0.7 | | F | | 102.16 | | |
| 215 | A | 1.69 | | J | | 106.03 | ND | >30 |
| 216 | B | 1.35 | | F | | 99.97 | | |
| 217 | A | 1.47 | | F | | 87.87 | | |
| 218 | A | 1.85 | | F | | 90.83 | | |
| 219 | B | 0.86 | | F | | 90.6 | | |
| 220 | B | 2.99 | | F | | 93.2 | ND | |
| 221 | A | 1.02 | | F | | 100.62 | ND | |
| 222 | C | 1.56 | | G | | 98.15 | | |
| 223 | A | 0.7 | | F | | 100.69 | ND | |
| 224 | A | 1.04 | | F | | 95.67 | | |
| 225 | B | 0.7 | | F | | 101.22 | | |
| 226 | C | 0.69 | | | | | | |
| 227 | C | 0.5 | | | | | | |
| 228 | E | 0.2 | | | | | | |
| 229 | C | 0.43 | | | | | | |
| 230 | A | 0.77 | | | | | | |
| 231 | C | 0.7 | | | | | | |
| 232 | C | 2.73 | | | | | | |
| 233 | A | 0.74 | | | | | | |
| 235 | E | ND | | | | | | |
| 237 | E | 0.72 | | | | | | |
| 238 | D | 0.7 | | | | | | |
| 239 | C | 0.7 | | | | | | |
| 240 | A | 1.44 | | | | | | |
| 241 | C | 0.7 | | | | | | |
| 243 | D | 0.7 | | | | | | |
| 244 | B | 1.9 | | | | | | |
| 245 | A | 1.28 | | | | | | |
| 246 | A | 3 | | | | | | |
| 247 | A | 2.34 | | | | | | |
| 248 | E | ND | | | | | | |
| 249 | B | 0.92 | | | | | | |
| 250 | C | 1.11 | | | | | | |
| 251 | E | ND | | | | | | |
| 252 | E | ND | | | | | | |
| 253 | E | ND | | | | | | |
| 254 | E | ND | | | | | | |
| 255 | E | ND | | | | | | |
| 260 | C | 1.53 | | | | | | |
| 261 | B | 3 | | G | | | 4 | 7.7 |
| 262 | B | 3 | | | | | 5 | 26.3 |
| 263 | B | 3 | | | | | | |
| 264 | C | 0.7 | | | | | | |
| 265 | C | 0.7 | | | | | | |
| 266 | A | 0.88 | 58.2 ± 78.3 | | | | | |

TABLE 5-continued

| | Characterization | | | | | | | |
|---|---|---|---|---|---|---|---|---|
| | | | Surface | | | Proliferation | | |
| | β-Cat FP | | Plasmon Resonance (Biacore ®) | Wnt Reporter | | % Viability non-Wnt responsive cells | Wnt dependent cells | Endo cells |
| SEQ ID NO. | $K_D$ (nM) | Hill slope | $K_D$ (nM) | $EC_{50}$ (uM) | Hill Slope | | $IC_{50}$ (uM) | $IC_{50}$ (uM) |
| 268 | E | | 299 ± 418 | | | | | |
| 270 | E | | 546 ± 503 | | | | | |
| 272 | C | 0.84 | | | | | | |
| 274 | A | 2.2 | | | | | | |
| 277 | E | 0.7 | | | | | | |
| 282/493 | A | 0.77 | | | | | | |
| 284 | C | 0.7 | | | | | | |
| 390 | | | | G | | | 4.7 | |
| 391 | | | | F | | | 4.8 | |
| 392 | | | | F | | | | |
| 393/500 | E | | | F | | | 1.7 | 5 |
| 394 | | | | G | | | | |
| 395 | | | | G | | | 6.8 | |
| 396 | | | | G | | | 2.9 | 15 |
| 397 | E | | | G | | | | |
| 398 | | | | G | | | | |
| 399 | | | | G | | | | |
| 400 | | | | G | | | | |
| 401 | B | 0.7 | | J | nd | | | |
| 402 | A | 0.7 | | J | nd | | | |
| 403 | A | 0.76 | | J | nd | | | |
| 404 | A | 0.79 | | J | nd | | | |
| 405 | A | 0.7 | | H | 0.8 | | 26.8 | |
| 406 | E | nd | | | | | | |
| 407 | E | nd | | | | | | |
| 408 | E | nd | | | | | | |
| 409 | E | nd | | | | | | |
| 410 | B | 1.6 | | J | nd | | | |
| 411 | C | 0.7 | | | | | | |
| 412 | C | 0.7 | | J | nd | | | |
| 413 | A | 0.7 | | J | nd | | | |
| 414 | A | 0.7 | | | | | | |
| 415 | A | 0.7 | | | | | | |
| 416 | A | 0.7 | | | | | | |
| 417 | A | 0.93 | | | | | | |
| 418 | E | 1.03 | | | | | | |
| 419 | A | 0.7 | | | | | | |
| 420 | B | 0.7 | | | | | | |
| 421 | A | 0.7 | | | | | | |
| 422 | B | 0.7 | | | | | | |
| 423 | B | 0.7 | | | | | | |
| 424 | A | 0.7 | | | | | | |
| 425 | A | 0.7 | | | | | | |
| 426 | A | 0.91 | | | | | | |
| 427 | A | 0.97 | | | | | | |
| 428 | A | 0.94 | | J | nd | | | |
| 429 | B | 0.7 | | | | | | |
| 430 | A | 1.75 | | H | nd | | | |
| 431 | A | 0.7 | | F | 3 | | | |
| 432 | A | 2.03 | | G | 2.2 | | 14.9 | 0.8 |
| 433 | B | 0.7 | | | | | | |
| 434 | A | 0.93 | | | | | | |
| 435 | A | 0.7 | | J | nd | | | |
| 436 | E | ND | | F | 2.3 | | | |
| 437 | A | 0.7 | | | | | | |
| 438 | A | 0.72 | | F | 2 | | | |
| 439 | A | 0.92 | | G | 2.8 | | | |
| 440 | A | 0.7 | | I | ND | | | |
| 441 | A | 1.86 | | J | ND | | | |
| 442 | A | 1.51 | | F | 2 | | | |
| 443 | A | 0.86 | | G | 3 | | | |
| 444 | A | 0.7 | | J | ND | | | |
| 445 | A | 0.7 | | I | ND | | | |
| 446 | A | 0.7 | | | | | | |
| 447 | A | 0.92 | | F | 3 | | | |
| 448 | A | 0.7 | | J | ND | | | |
| 449 | A | 0.89 | | J | ND | | | |
| 450 | B | 0.79 | | | | | | |
| 451 | C | 0.7 | | F | 1.9 | | | |

TABLE 5-continued

| | Characterization | | | | | | |
|---|---|---|---|---|---|---|---|
| | Surface | | | | Proliferation | | |
| | β-Cat FP | | Plasmon Resonance (Biacore ®) | Wnt Reporter | | % Viability non-Wnt responsive cells | Wnt dependent cells | Endo cells |
| SEQ ID NO. | $K_D$ (nM) | Hill slope | $K_D$ (nM) | $EC_{50}$ (uM) | Hill Slope | | $IC_{50}$ (uM) | $IC_{50}$ (uM) |
| 452 | B | 0.7 | | H | 1 | | | |
| 453 | C | 0.7 | | F | 3 | | | |
| 454 | C | 0.7 | | F | 3 | | | |
| 455 | A | 1.03 | | | | | | |
| 456 | | | | F | 2.2 | | | |
| 458 | B | 0.7 | | | | | | |
| 459 | A | 1.4 | | F | 3 | | | |
| 460 | A | 0.7 | | | | | | |
| 461 | A | 1.06 | | F | 3 | | | |
| 462 | A | 0.76 | | | | | | |
| 463 | A | 0.78 | | F | 3 | | | |
| 464 | B | 0.7 | | | | | | |
| 465 | B | 0.7 | | F | 3 | | | |
| 466 | A | 0.72 | | | | | | |
| 467 | A | 0.94 | | F | 3 | | | |
| 468 | A | 0.86 | | | | | | |
| 469 | A | 0.98 | | F | 0.8 | | | |
| 470 | A | 0.81 | | | | | | |
| 471 | A | 1.07 | | F | 3 | | | |
| 472 | A | 0.89 | | G | 3 | | | |
| 473 | A | 1.16 | | F | 1.1 | | | |
| 476 | | | | G | 2.6 | | | |
| 477 | | | | F | 3 | | | |
| 485 | | | | J | 3 | | | |
| 486 | | | | J | 1.4 | | | |
| 487 | | | | F | 2.4 | | | |
| 488 | | | | F | 0.1 | | | |
| 489 | | | | H | 0.8 | | | |
| 490 | | | | F | 0.9 | | | |

β-Catenin $K_D$ ranges:
A = 0-400 nm
B = >400 to 1000 nM
C = >1000 to 10,000 nM
D = >10,000 to 30,000 nM
E = >30,000 nM
Wnt Reporter $EC_{50}$ ranges:
F = >0 to 7.5 uM
G = >7.5 to 15 uM
H = >15 to 22.5 uM
I = >22.5 to 30 uM
J = >30 uM

We claim:

1. A peptide comprising an amino acid sequence having the formula $X_1—X_2—X_3—X_4—X_5—X_6—X_7—X_8—X_9—X_{10}—X_{11}—X_{12}—X_{13}—X_{14}—X_{15}—X_{16}$ (SEQ ID NO: 504), wherein:

$X_1$ is M;
$X_2$ is S;
$X_3$ is R;
$X_4$ is K or R;
$X_5$ is M;
$X_6$ is W;
$X_7$ is F;
$X_8$ is L;
$X_9$ is L;

$X_{10}$ is C;
$X_{11}$ is F;
$X_{12}$ is W; and
$X_{13}$ is G.

2. The peptide of claim 1, wherein the peptide binds to β-catenin.

3. The peptide of claim 2, wherein the peptide inhibits $W_{nt}$ pathway activity with an $EC_{50}$ of less than 50 μM.

4. The peptide of claim 1, wherein the peptide is a β-catenin inhibitor.

5. The peptide of claim 1, wherein the peptide is an inhibitor of β-catenin translocation to the nucleus.

6. The peptide of claim 1, wherein the peptide prevents β-catenin acting as a transcription factor to oncogenes, Matrix Metalloproteinase 9 (MMP9), or Chloride C3 Channel (ClC-3).

7. The peptide of claim 1, wherein the peptide prevents transformation, invasion, migration, fibrogenesis, or any combination thereof, of end endometriosis (EMS) cells.

8. The peptide of claim 1, wherein the peptide prevents β-catenin from binding to estrogen receptor (ESR1).

9. The peptide of claim 1, wherein the peptide does not decrease membrane activity of β-catenin.

10. The peptide of claim 1, wherein the peptide does not decrease β-catenin E-cadherin binding.

11. The peptide of claim 1, wherein the peptide prevents oncogenic transcription factor activity.

12. The peptide of claim 1, wherein the peptide is a circularized or bicyclic peptide.

13. The peptide of claim 12, wherein the peptide is circularized with an amide bond.

14. The peptide of claim 13, wherein the amide bond is head-to-tail between the N-terminus and the C-terminus.

15. The peptide of claim 12, wherein the peptide is circularized utilizing hydrocarbon stapling.

16. The peptide of claim 12, wherein the peptide is circularized utilizing click chemistry.

17. The peptide of claim 1, wherein the peptide comprises one or more non-natural amino acids.

18. The peptide of claim 17, wherein the one or more non-natural amino acids are N-methyl amino acids.

* * * * *